(12) United States Patent
Noda et al.

(10) Patent No.: US 10,870,861 B2
(45) Date of Patent: Dec. 22, 2020

(54) CREATION OF CHRYSANTHEMUM WITH BLUE FLOWER COLOR

(71) Applicant: SUNTORY HOLDINGS LIMITED, Osaka (JP)

(72) Inventors: Naonobu Noda, Tsukuba (JP); Ryutaro Aida, Tsukuba (JP); Satoshi Hongo, Tsukuba (JP); Sanae Sato, Tsukuba (JP); Yoshikazu Tanaka, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 15/740,944

(22) PCT Filed: Jun. 30, 2016

(86) PCT No.: PCT/JP2016/069536
§ 371 (c)(1),
(2) Date: Dec. 29, 2017

(87) PCT Pub. No.: WO2017/002945
PCT Pub. Date: Jan. 5, 2017

(65) Prior Publication Data
US 2019/0032066 A1    Jan. 31, 2019

(30) Foreign Application Priority Data
Jul. 1, 2015    (JP) ................................ 2015-133069

(51) Int. Cl.
| A01H 5/10 | (2018.01) |
| C12N 15/82 | (2006.01) |
| A01H 5/00 | (2018.01) |
| A01H 5/02 | (2018.01) |
| C07K 14/415 | (2006.01) |
| A01H 6/14 | (2018.01) |
| C12N 9/02 | (2006.01) |
| C12N 9/10 | (2006.01) |

(52) U.S. Cl.
CPC .............. *C12N 15/827* (2013.01); *A01H 5/00* (2013.01); *A01H 5/02* (2013.01); *A01H 6/1424* (2018.05); *C07K 14/415* (2013.01); *C12N 9/0073* (2013.01); *C12N 9/1051* (2013.01); *C12N 15/825* (2013.01); *C12Y 114/13088* (2013.01); *C12Y 204/01* (2013.01)

(58) Field of Classification Search
None
See application file for complete search history.

(56) References Cited

U.S. PATENT DOCUMENTS

| 6,596,927 B1 | 7/2003 | Mizutani et al. |
| 7,105,719 B1 | 9/2006 | Ashikari et al. |
| 2009/0288225 A1 | 11/2009 | Noda et al. |
| 2010/0287667 A1 | 11/2010 | Tanaka et al. |
| 2010/0287668 A1 | 11/2010 | Tanaka et al. |
| 2011/0055963 A1 | 3/2011 | Tanaka et al. |
| 2011/0219476 A1 | 9/2011 | Ono et al. |
| 2012/0096589 A1* | 4/2012 | Noda .................. C12N 9/0071 800/282 |
| 2012/0135469 A1 | 5/2012 | Ozeki et al. |
| 2014/0033369 A1 | 1/2014 | Tanaka et al. |
| 2015/0074855 A1 | 3/2015 | Tanaka et al. |
| 2017/0058269 A1 | 3/2017 | Tanaka et al. |

FOREIGN PATENT DOCUMENTS

| JP | 2005-095005 A * | 4/2005 |
| WO | WO-94/003606 A1 | 2/1994 |
| WO | WO-96/025500 A1 | 8/1996 |
| WO | WO-2000/044907 A1 | 8/2000 |
| WO | WO-2002/086110 A | 10/2002 |
| WO | WO-2006/046780 A1 | 5/2006 |
| WO | WO-2006/105598 A1 | 10/2006 |
| WO | WO-2007/046148 A1 | 4/2007 |
| WO | WO-2008/156211 A1 | 12/2008 |
| WO | WO-2008/156214 A1 | 12/2008 |
| WO | WO-2010/026666 A1 | 3/2010 |
| WO | WO-2010/069004 A1 | 6/2010 |
| WO | WO-2010/122849 A1 | 10/2010 |
| WO | WO-2011/016260 A1 | 2/2011 |
| WO | WO-2012/096307 A1 | 7/2012 |
| WO | WO-2013/157502 A1 | 10/2013 |
| WO | WO-2015/167016 A1 | 11/2015 |
| WO | WO-2017/002945 A1 | 1/2017 |

OTHER PUBLICATIONS

Fukuchi-Mizutani et al., 2003, Plant Physiology 132: 1652-1663.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Tanaka et al., 2009, Recent Progress of Flower Colour Modification by Biotechnology, Int. J. Mol. Sci. 10: 5350-5369.*
Andersen et al., 2006, The Anthocyanins, In: Flavonoids, Chemistry, Biochemistry and Applications, ed. Andersen and Markham, Taylor & Francis, pp. 471-537.*
Falginella et al., 2010, Expansion and subfunctionalisation of flavonoid 3',5'-hydroxylases in the grapevine lineage, BMC Genomics 11:562, 1-18.*

(Continued)

*Primary Examiner* — Bratislav Stankovic
(74) *Attorney, Agent, or Firm* — Faegre Drinker Biddle & Reath LLP

(57) ABSTRACT

Provided are transformed *chrysanthemum* plants having blue flower color, their self-fertilized progenies or cross-fertilized progenies thereof, a vegetative propagated plants thereof, and a part, a tissue or a cell of the plant body. Anthocyanin 3',5'-O-glucosyltransferase gene (CtA3'5'GT) derived from *Clitoria ternatea* and flavonoid 3',5'-hydroxylase gene derived from *Campanula* (CamF3'5'H) are coexpressed in *chrysanthemum* petals.

14 Claims, 6 Drawing Sheets
Specification includes a Sequence Listing.

(56) References Cited

OTHER PUBLICATIONS

Yoshiaki Kanno et al., "Chomame Yurai Anthocyanin 3',5'-O-Glucosyl-ki Ten'i Koso Idenshi o Donyu shita Keishitsu Tenkan Lobelia no Kaiseki," Japanese Society for Plant Cell and Molecular Biology Tsukuba Taikai Symposium Koen Yoshishu, 2006, p. 40, vol. 24 [non-English language].

Naonobu Noda et al., "Genetic Engineering of Novel Bluer-Colored Chrysanthemums Produced by Accumulation of Delphinidin-Based Anthocyanins," Plant Cell Physiology, 2013, pp. 1684-1695, vol. 54, No. 10.

Nobuhiro Sasaki et al., "Achivements and Perspectives in Biochemistry Concerning Anthocyanin Modification for Blue Flower Coloration," Plant Cell Physiology, 2015, pp. 28-40, vol. 56, No. 1.

Kumi Yoshida et al., "Blue flower color development by anthocyanins: from chemical structure to cell physiology," Natural Product Reports, 2009, pp. 884-915, vol. 26.

International Search Report dated Sep. 27, 2016 for PCT/JP2016/069536.

Kogawa, K., et al., "Purification and characterization of UDP-glucose: anthocyanin 3',5'-O-glucosyltransferase from *Clitoria ternatea*," Planta, 2007, 226:1501-1509.

Brazier-Hicks et al., "The C-Glycosylation of Flavonoids in Cereals*," The Journal of Biological Chemistry, vol. 284, No. 27, pp. 17926-17934, 2009.

Negishi et al., "Tonoplast- and Plasma Membrane-Localized Aquaporin-Family Transporters in Blue Hydrangea Sepals of Aluminum Hyperaccumulating Plant," PLOS One, vol. 7, Issue 8, pp. e43189-e43189, 2012.

Negishi et al., "Plasma membrane-localized Al-transporter from blue, hydrangea sepals is a member of the anion permease family," Genes to Cells, vol. 18, pp. 341-352, 2013.

Hirotani et al., "Cloning and expression of UDP-glucose: flavonoid 7-O-glucosyltransferase from hairy root cultures of *Scutellaria baicalensis*," Planta, vol. 210, pp. 1006-1013, 2000.

Kim et al., "Characterization of Flavonoid 7-O-Glucosyltransferase from *Arabidopsis thaliana*," Bioscience, Biotechnology, and Biochemistry, vol. 70, No. 6, pp. 1471-1477, 2006.

Saito et al., "A cyanidin glycoside giving scarlet coloration in plants of the Bromeliaceae," Phytochemistry 22:1735-1740, 1983.

Andersen et al., "The Anthocyanins," in *Flavonoids, Chemistry, Biochemistry and Applications*, Edited by Andersen, O.M. & Markham, K.R., Taylor & Francis, 2006, pp. 471-537.

Shimizu-Yumoto et al., "Slantingly cross loading sample system enables simultaneous performance of separation and mixture to detect molecular interactions on thin-layer chromatography," J. Chromatogr. A, 1245:183-189, 2012.

Noda N. et al., "Generation of blue chrysanthemums by anthocyanin B-ring hydroxylation and glycosylation and its coloration mechanism," Sci. Adv. 3:e1602785 (2017).

Saito et al., "Covalent anthocyanin-flavonol complexes from the violet-blue flowers of *Allium* 'Blue Perfume'," Phytochemistry 80:99-108, 2012.

\* cited by examiner

SEQUENCE LISTING

<160> NUMBER OF SEQ ID NOS: 38

<210> SEQ ID NO 1
<211> LENGTH: 1594
<212> TYPE: DNA
<213> ORGANISM: Clitoria ternatea
<220> FEATURE:
<221> NAME/KEY: CDS
<222> LOCATION: (7)..(1347)

<400> SEQUENCE: 1

```
aaccaa atg gaa aac aat aag cat gtc gta atc ttc cca ttt ccc ttt         48
       Met Glu Asn Asn Lys His Val Val Ile Phe Pro Phe Pro Phe
       1               5                   10 gga agc cac ctt cca cct ctc ttg aac ctc gtc ttc aaa ctc gct cac         96
Gly Ser His Leu Pro Pro Leu Leu Asn Leu Val Phe Lys Leu Ala His
15                  20                  25                  30 gcc gct cca aac act tca ttc tca ttc atc ggc aca cac act tcc aac        144
Ala Ala Pro Asn Thr Ser Phe Ser Phe Ile Gly Thr His Thr Ser Asn
                35                  40                  45 gca ttc ctt ttc act aaa cgc cac gtc cca gac aac atc agg gtc ttc        192
Ala Phe Leu Phe Thr Lys Arg His Val Pro Asp Asn Ile Arg Val Phe
            50                  55                  60 acc atc agc gat gga atc cca gag ggt tat gtg ccc ggc aac aac cca        240
Thr Ile Ser Asp Gly Ile Pro Glu Gly Tyr Val Pro Gly Asn Asn Pro
65                  70                  75 atc gta aaa ctc gat ttt ttc ctc tcc act ggt ccc gac aac ttg tgc        288
Ile Val Lys Leu Asp Phe Phe Leu Ser Thr Gly Pro Asp Asn Leu Cys
80                  85                  90 aag ggc att gaa ctt gcc gtt gca gag acc aaa cag agt gtc act tgc        336
Lys Gly Ile Glu Leu Ala Val Ala Glu Thr Lys Gln Ser Val Thr Cys
95                  100                 105                 110 atc att gcc gat gct ttt gta acc tct tct ctc ctt gtg gct cag acc        384
Ile Ile Ala Asp Ala Phe Val Thr Ser Ser Leu Leu Val Ala Gln Thr
                115                 120                 125 ctc aat gtt cct tgg att gtg ttt tgg ccc aat gtg tca tgc tca ctt        432
Leu Asn Val Pro Trp Ile Val Phe Trp Pro Asn Val Ser Cys Ser Leu
            130                 135                 140 tct ctt tac ttc agc att gat ttg ata aga gac aag tgt acg aat gat        480
Ser Leu Tyr Phe Ser Ile Asp Leu Ile Arg Asp Lys Cys Thr Asn Asp
            145                 150                 155 gct aaa aac gca agc ttg gat ttc ctt cct ggg ttg tcc aaa ttg cgc        528
Ala Lys Asn Ala Ser Leu Asp Phe Leu Pro Gly Leu Ser Lys Leu Arg
160                 165                 170
```

|     |     |
| --- | --- |
| gtt gag gat gtc cca cgg cca cag gcc att gtt ttg gat gga aag gag<br>Val Glu Asp Val Pro Arg Pro Gln Ala Ile Val Leu Asp Gly Lys Glu<br>175                      180                      185                      190 | 576 |
| aca ctg ttt gca agg acg ttg aat tcg ttg ggt acg gtg tta cct caa<br>Thr Leu Phe Ala Arg Thr Leu Asn Ser Leu Gly Thr Val Leu Pro Gln<br>                      195                      200                      205 | 624 |
| gct aag gcg gtg gtt gtg aat ttc ttt gca gaa tta gac cca cct tta<br>Ala Lys Ala Val Val Val Asn Phe Phe Ala Glu Leu Asp Pro Pro Leu<br>              210                      215                      220 | 672 |
| ttt gtt aag gat atg aga tcc aag ttg cag tct ttg ctc ttc gtt gat<br>Phe Val Lys Asp Met Arg Ser Lys Leu Gln Ser Leu Leu Phe Val Asp<br>225                      230                      235 | 720 |
| cca ctt cca tgc cca caa ttg cta ctc cct gag aca gat tca aat ggg<br>Pro Leu Pro Cys Pro Gln Leu Leu Leu Pro Glu Thr Asp Ser Asn Gly<br>        240                      245                      250 | 768 |
| tgc atg tcg tgg ttg gat tcc aag agt tct aga tcc gtg gct tat gtt<br>Cys Met Ser Trp Leu Asp Ser Lys Ser Ser Arg Ser Val Ala Tyr Val<br>255                      260                      265                      270 | 816 |
| tgt ttt gga acc gcg gtg agt cta ccg cca caa gaa gtt gta gag gtc<br>Cys Phe Gly Thr Ala Val Ser Leu Pro Pro Gln Glu Val Val Glu Val<br>                      275                      280                      285 | 864 |
| gca gag gca ttg gag gaa agt ggt ttt cca ttt ctt ttg gcc ctc agt<br>Ala Glu Ala Leu Glu Glu Ser Gly Phe Pro Phe Leu Leu Ala Leu Ser<br>              290                      295                      300 | 912 |
| gaa agt cta att ggt gtt ttg cca aaa ggg ttg gtt gag agg acc atg<br>Glu Ser Leu Ile Gly Val Leu Pro Lys Gly Leu Val Glu Arg Thr Met<br>305                      310                      315 | 960 |
| acc cgt ggg aaa gtg gtg tct tgg gca cca cag tct ctc gtt tta tcg<br>Thr Arg Gly Lys Val Val Ser Trp Ala Pro Gln Ser Leu Val Leu Ser<br>        320                      325                      330 | 1008 |
| cat ggt tct gtt gga gta ttt gtg act cac tgt gga gct aac tct gtg<br>His Gly Ser Val Gly Val Phe Val Thr His Cys Gly Ala Asn Ser Val<br>335                      340                      345                      350 | 1056 |
| act gag agt att tcc aat ggg gtt cct atg ata tgc agg ccc ttc ttt<br>Thr Glu Ser Ile Ser Asn Gly Val Pro Met Ile Cys Arg Pro Phe Phe<br>                      355                      360                      365 | 1104 |
| ggg gac caa gga ata gct gca cgg gtt ata cag gat att tgg gag att<br>Gly Asp Gln Gly Ile Ala Ala Arg Val Ile Gln Asp Ile Trp Glu Ile<br>              370                      375                      380 | 1152 |
| ggg gtg atc cta gaa ggt agg att ttt acc aaa aat ggg ttt gtg aaa<br>Gly Val Ile Leu Glu Gly Arg Ile Phe Thr Lys Asn Gly Phe Val Lys<br>385                      390                      395 | 1200 |
| aac ttg aat cta att ctg gtg cag gaa gaa ggg aag aag atc agg gac<br>Asn Leu Asn Leu Ile Leu Val Gln Glu Glu Gly Lys Lys Ile Arg Asp<br>        400                      405                      410 | 1248 |
| aat gct ctt aaa gtg aag cag att gtg caa gat gca gct ggg cca cat<br>Asn Ala Leu Lys Val Lys Gln Ile Val Gln Asp Ala Ala Gly Pro His<br>415                      420                      425                      430 | 1296 |
| gga caa gct gca gag gat ttc aac act ttg gtg gaa atg att tcc tct<br>Gly Gln Ala Ala Glu Asp Phe Asn Thr Leu Val Glu Met Ile Ser Ser<br>                      435                      440                      445 | 1344 |
| agc taaattatag gagaagataa ataatactag taaattgtgt tttgtaccaa<br>Ser | 1397 |
| ttaaatatgt gttgggagtt gttttatgaa agtgttttag gtatactttt tatgggaaaa | 1457 |
| aaattaaaaa gaaaacttct ccatgttagt agaagtatta aagtttatt ttcgaataaa | 1517 |
| tcggatcatc aagacattta aaacatgaaa tatttatgtt tttggtaaaa aaaaaaaaaa | 1577 |
| aaaaaaaaaa aaaaaaa | 1594 |

<210> SEQ ID NO 2
<211> LENGTH: 447
<212> TYPE: PRT
<213> ORGANISM: Clitoria ternatea

<400> SEQUENCE: 2

```
Met Glu Asn Asn Lys His Val Val Ile Phe Pro Phe Pro Phe Gly Ser
1               5                  10                  15

His Leu Pro Pro Leu Leu Asn Leu Val Phe Lys Leu Ala His Ala Ala
            20                  25                  30

Pro Asn Thr Ser Phe Ser Phe Ile Gly Thr His Thr Ser Asn Ala Phe
        35                  40                  45

Leu Phe Thr Lys Arg His Val Pro Asp Asn Ile Arg Val Phe Thr Ile
50                  55                  60

Ser Asp Gly Ile Pro Glu Gly Tyr Val Pro Gly Asn Asn Pro Ile Val
65                  70                  75                  80

Lys Leu Asp Phe Phe Leu Ser Thr Gly Pro Asp Asn Leu Cys Lys Gly
                85                  90                  95

Ile Glu Leu Ala Val Ala Glu Thr Lys Gln Ser Val Thr Cys Ile Ile
            100                 105                 110

Ala Asp Ala Phe Val Thr Ser Ser Leu Leu Val Ala Gln Thr Leu Asn
        115                 120                 125

Val Pro Trp Ile Val Phe Trp Pro Asn Val Ser Cys Ser Leu Ser Leu
130                 135                 140

Tyr Phe Ser Ile Asp Leu Ile Arg Asp Lys Cys Thr Asn Asp Ala Lys
145                 150                 155                 160

Asn Ala Ser Leu Asp Phe Leu Pro Gly Leu Ser Lys Leu Arg Val Glu
                165                 170                 175

Asp Val Pro Arg Pro Gln Ala Ile Val Leu Asp Gly Lys Glu Thr Leu
            180                 185                 190

Phe Ala Arg Thr Leu Asn Ser Leu Gly Thr Val Leu Pro Gln Ala Lys
        195                 200                 205

Ala Val Val Asn Phe Phe Ala Glu Leu Asp Pro Pro Leu Phe Val
210                 215                 220

Lys Asp Met Arg Ser Lys Leu Gln Ser Leu Leu Phe Val Asp Pro Leu
225                 230                 235                 240

Pro Cys Pro Gln Leu Leu Leu Pro Glu Thr Asp Ser Asn Gly Cys Met
                245                 250                 255

Ser Trp Leu Asp Ser Lys Ser Ser Arg Ser Val Ala Tyr Val Cys Phe
            260                 265                 270

Gly Thr Ala Val Ser Leu Pro Pro Gln Glu Val Val Glu Val Ala Glu
        275                 280                 285

Ala Leu Glu Glu Ser Gly Phe Pro Phe Leu Leu Ala Leu Ser Glu Ser
        290                 295                 300

Leu Ile Gly Val Leu Pro Lys Gly Leu Val Glu Arg Thr Met Thr Arg
305                 310                 315                 320

Gly Lys Val Val Ser Trp Ala Pro Gln Ser Leu Val Leu Ser His Gly
                325                 330                 335

Ser Val Gly Val Phe Val Thr His Cys Gly Ala Asn Ser Val Thr Glu
            340                 345                 350

Ser Ile Ser Asn Gly Val Pro Met Ile Cys Arg Pro Phe Phe Gly Asp
        355                 360                 365

Gln Gly Ile Ala Ala Arg Val Ile Gln Asp Ile Trp Glu Ile Gly Val
        370                 375                 380
```

```
Ile Leu Glu Gly Arg Ile Phe Thr Lys Asn Gly Phe Val Lys Asn Leu
385                 390                 395                 400

Asn Leu Ile Leu Val Gln Glu Gly Lys Lys Ile Arg Asp Asn Ala
            405                 410                 415

Leu Lys Val Lys Gln Ile Val Gln Asp Ala Ala Gly Pro His Gly Gln
        420                 425                 430

Ala Ala Glu Asp Phe Asn Thr Leu Val Glu Met Ile Ser Ser Ser
        435                 440                 445

<210> SEQ ID NO 3
<211> LENGTH: 1585
<212> TYPE: DNA
<213> ORGANISM: Campanula medium
<220> FEATURE:
<221> NAME/KEY: CDS
<222> LOCATION: (12)..(1574)

<400> SEQUENCE: 3
gtgaagccac c atg tct ata gac ata acc att ctc tta tgt gaa ctt gtt       50
            Met Ser Ile Asp Ile Thr Ile Leu Leu Cys Glu Leu Val
              1               5                  10 gct gca att tca ctc tac tta tta acc tac tat ttc att tgt ttc ctc       98
Ala Ala Ile Ser Leu Tyr Leu Leu Thr Tyr Tyr Phe Ile Cys Phe Leu
         15                  20                  25 ttc aaa ccc tct cat cat cac cac cac ctc cct ccc ggc cca acc gga      146
Phe Lys Pro Ser His His His His His Leu Pro Pro Gly Pro Thr Gly
 30                  35                  40                  45 tgg ccg atc att gga tcc ctt cct ctc tta ggc act atg cca cat gtt      194
Trp Pro Ile Ile Gly Ser Leu Pro Leu Leu Gly Thr Met Pro His Val
                 50                  55                  60 tcc tta gcc gac atg gcc gta aaa tac ggg cct ata atg tac cta aaa      242
Ser Leu Ala Asp Met Ala Val Lys Tyr Gly Pro Ile Met Tyr Leu Lys
             65                  70                  75 ctt ggt tca aag ggc acc gtc gtg gcc tca aat cca aaa gcc gcc cga      290
Leu Gly Ser Lys Gly Thr Val Val Ala Ser Asn Pro Lys Ala Ala Arg
         80                  85                  90 gca ttc ttg aaa tcc cat gat gcc aat ttt tct aac cgt ccg att gat      338
Ala Phe Leu Lys Ser His Asp Ala Asn Phe Ser Asn Arg Pro Ile Asp
     95                  100                 105 ggg ggg ccc acc tac ctc gcg tat aat gca caa gac atg gtt ttt gca      386
Gly Gly Pro Thr Tyr Leu Ala Tyr Asn Ala Gln Asp Met Val Phe Ala
110                 115                 120                 125 gaa tat ggc cca aaa tgg aag ctt ttg cga aag cta tgt agc ttg cac      434
Glu Tyr Gly Pro Lys Trp Lys Leu Leu Arg Lys Leu Cys Ser Leu His
                 130                 135                 140 atg tta ggc ccg aag gca ctc gag gat tgg gct cat gtc aga gtt tca      482
Met Leu Gly Pro Lys Ala Leu Glu Asp Trp Ala His Val Arg Val Ser
             145                 150                 155 gag gtc ggt cat atg ctc aaa gaa atg tac gag caa tcg agt aag tcc      530
Glu Val Gly His Met Leu Lys Glu Met Tyr Glu Gln Ser Ser Lys Ser
         160                 165                 170 gtg cca gtg gtg gtg cca gag atg tta act tat gcc atg gct aat atg      578
Val Pro Val Val Val Pro Glu Met Leu Thr Tyr Ala Met Ala Asn Met
175                 180                 185 att gga cga atc ata ctc agt cga cgc cct ttt gtt atc acg agc aaa      626
Ile Gly Arg Ile Ile Leu Ser Arg Arg Pro Phe Val Ile Thr Ser Lys
190                 195                 200                 205 tta gac tcg tct gct tct gct gct tct gtt agt gaa ttc caa tat atg      674
Leu Asp Ser Ser Ala Ser Ala Ala Ser Val Ser Glu Phe Gln Tyr Met
                 210                 215                 220
```

```
gtt atg gag ctc atg agg atg gca ggg ttg ttc aat att ggt gat ttc      722
Val Met Glu Leu Met Arg Met Ala Gly Leu Phe Asn Ile Gly Asp Phe
            225                 230                 235 ata cca tat att gcg tgg atg gat ttg caa ggc att caa cgc gat atg      770
Ile Pro Tyr Ile Ala Trp Met Asp Leu Gln Gly Ile Gln Arg Asp Met
            240                 245                 250 aag gtt ata cag caa aag ttt gat gtc ttg ttg aac aaa atg atc aag      818
Lys Val Ile Gln Gln Lys Phe Asp Val Leu Leu Asn Lys Met Ile Lys
            255                 260                 265 gaa cat aca gaa tcc gct cat gat cgt aaa gat aat cct gat ttt ctt      866
Glu His Thr Glu Ser Ala His Asp Arg Lys Asp Asn Pro Asp Phe Leu
270                 275                 280                 285 gat att ctt atg gcg gct acc caa gaa aac acg gag gga att cag ctt      914
Asp Ile Leu Met Ala Ala Thr Gln Glu Asn Thr Glu Gly Ile Gln Leu
                290                 295                 300 aat ctc gta aat gtt aag gcg ctt ctt ttg gat tta ttc acg gcg ggc      962
Asn Leu Val Asn Val Lys Ala Leu Leu Leu Asp Leu Phe Thr Ala Gly
                305                 310                 315 acg gat aca tcg tcg agt gtg atc gaa tgg gca cta gcc gaa atg ttg     1010
Thr Asp Thr Ser Ser Ser Val Ile Glu Trp Ala Leu Ala Glu Met Leu
            320                 325                 330 aac aat cga cag atc cta aac cgg gcc cac gaa gaa atg gac caa gtc     1058
Asn Asn Arg Gln Ile Leu Asn Arg Ala His Glu Glu Met Asp Gln Val
            335                 340                 345 att ggc aga aac aga aga cta gaa caa tct gac ata cca aac ttg cca     1106
Ile Gly Arg Asn Arg Arg Leu Glu Gln Ser Asp Ile Pro Asn Leu Pro
350                 355                 360                 365 tat ttc caa gcc ata tgc aaa gaa aca ttc cga aaa cac cct tcc acg     1154
Tyr Phe Gln Ala Ile Cys Lys Glu Thr Phe Arg Lys His Pro Ser Thr
                370                 375                 380 ccc tta aac ctc cca aga atc tca aca gaa gaa tgt gaa gtc gaa gga     1202
Pro Leu Asn Leu Pro Arg Ile Ser Thr Glu Glu Cys Glu Val Glu Gly
                385                 390                 395 ttt cgc ata ccc aaa aac act aga cta ata gtg aac ata tgg gca ata     1250
Phe Arg Ile Pro Lys Asn Thr Arg Leu Ile Val Asn Ile Trp Ala Ile
            400                 405                 410 ggg aga gac cct aaa gtg tgg gaa aat cca ttg gat ttt acc ccg gaa     1298
Gly Arg Asp Pro Lys Val Trp Glu Asn Pro Leu Asp Phe Thr Pro Glu
415                 420                 425 cga ttc ttg agt gaa aaa cac gcg aaa att gat ccg cga ggt aat cat     1346
Arg Phe Leu Ser Glu Lys His Ala Lys Ile Asp Pro Arg Gly Asn His
430                 435                 440                 445 ttt gag tta atc cca ttt ggg gcg gga cgg agg ata tgt gca ggg gct     1394
Phe Glu Leu Ile Pro Phe Gly Ala Gly Arg Arg Ile Cys Ala Gly Ala
                450                 455                 460 aga atg gga gcg gcc tcg gtc gag tac att tta ggt aca ttg gtg cac     1442
Arg Met Gly Ala Ala Ser Val Glu Tyr Ile Leu Gly Thr Leu Val His
            465                 470                 475 tca ttt gat tgg aaa ttg cct gat gga gtt gtg gaa gtt aat atg gaa     1490
Ser Phe Asp Trp Lys Leu Pro Asp Gly Val Val Glu Val Asn Met Glu
            480                 485                 490 gag agc ttt ggg ata gca ttg cag aaa aag atg cct ctt tct gct att     1538
Glu Ser Phe Gly Ile Ala Leu Gln Lys Lys Met Pro Leu Ser Ala Ile
            495                 500                 505 gtt act cca aga ttg cct cca agt gct tac act gtc taggcaaatg c        1585
Val Thr Pro Arg Leu Pro Pro Ser Ala Tyr Thr Val
510                 515                 520
```

<210> SEQ ID NO 4

```
<211> LENGTH: 521
<212> TYPE: PRT
<213> ORGANISM: Campanula medium

<400> SEQUENCE: 4

Met Ser Ile Asp Ile Thr Ile Leu Leu Cys Glu Leu Val Ala Ala Ile
1               5                   10                  15

Ser Leu Tyr Leu Leu Thr Tyr Tyr Phe Ile Cys Phe Leu Phe Lys Pro
            20                  25                  30

Ser His His His His Leu Pro Pro Gly Pro Thr Gly Trp Pro Ile
        35                  40                  45

Ile Gly Ser Leu Pro Leu Leu Gly Thr Met Pro His Val Ser Leu Ala
    50                  55                  60

Asp Met Ala Val Lys Tyr Gly Pro Ile Met Tyr Leu Lys Leu Gly Ser
65                  70                  75                  80

Lys Gly Thr Val Val Ala Ser Asn Pro Lys Ala Ala Arg Ala Phe Leu
                85                  90                  95

Lys Ser His Asp Ala Asn Phe Ser Asn Arg Pro Ile Asp Gly Gly Pro
            100                 105                 110

Thr Tyr Leu Ala Tyr Asn Ala Gln Asp Met Val Phe Ala Glu Tyr Gly
        115                 120                 125

Pro Lys Trp Lys Leu Leu Arg Lys Leu Cys Ser Leu His Met Leu Gly
    130                 135                 140

Pro Lys Ala Leu Glu Asp Trp Ala His Val Arg Val Ser Glu Val Gly
145                 150                 155                 160

His Met Leu Lys Glu Met Tyr Glu Gln Ser Ser Lys Ser Val Pro Val
                165                 170                 175

Val Val Pro Glu Met Leu Thr Tyr Ala Met Ala Asn Met Ile Gly Arg
            180                 185                 190

Ile Ile Leu Ser Arg Arg Pro Phe Val Ile Thr Ser Lys Leu Asp Ser
        195                 200                 205

Ser Ala Ser Ala Ala Ser Val Ser Glu Phe Gln Tyr Met Val Met Glu
    210                 215                 220

Leu Met Arg Met Ala Gly Leu Phe Asn Ile Gly Asp Phe Ile Pro Tyr
225                 230                 235                 240

Ile Ala Trp Met Asp Leu Gln Gly Ile Gln Arg Asp Met Lys Val Ile
                245                 250                 255

Gln Gln Lys Phe Asp Val Leu Leu Asn Lys Met Ile Lys Glu His Thr
            260                 265                 270

Glu Ser Ala His Asp Arg Lys Asp Asn Pro Asp Phe Leu Asp Ile Leu
        275                 280                 285

Met Ala Ala Thr Gln Glu Asn Thr Glu Gly Ile Gln Leu Asn Leu Val
    290                 295                 300

Asn Val Lys Ala Leu Leu Leu Asp Leu Phe Thr Ala Gly Thr Asp Thr
305                 310                 315                 320

Ser Ser Ser Val Ile Glu Trp Ala Leu Ala Glu Met Leu Asn Asn Arg
                325                 330                 335

Gln Ile Leu Asn Arg Ala His Glu Glu Met Asp Gln Val Ile Gly Arg
            340                 345                 350

Asn Arg Arg Leu Glu Gln Ser Asp Ile Pro Asn Leu Pro Tyr Phe Gln
        355                 360                 365

Ala Ile Cys Lys Glu Thr Phe Arg Lys His Pro Ser Thr Pro Leu Asn
    370                 375                 380

Leu Pro Arg Ile Ser Thr Glu Glu Cys Glu Val Glu Gly Phe Arg Ile
```

```
                385                 390                 395                 400
        Pro Lys Asn Thr Arg Leu Ile Val Asn Ile Trp Ala Ile Gly Arg Asp
                        405                 410                 415

Pro Lys Val Trp Glu Asn Pro Leu Asp Phe Thr Pro Glu Arg Phe Leu
                        420                 425                 430

Ser Glu Lys His Ala Lys Ile Asp Pro Arg Gly Asn His Phe Glu Leu
                        435                 440                 445

Ile Pro Phe Gly Ala Gly Arg Arg Ile Cys Ala Gly Ala Arg Met Gly
                450                 455                 460

Ala Ala Ser Val Glu Tyr Ile Leu Gly Thr Leu Val His Ser Phe Asp
        465                 470                 475                 480

Trp Lys Leu Pro Asp Gly Val Val Glu Val Asn Met Glu Glu Ser Phe
                        485                 490                 495

Gly Ile Ala Leu Gln Lys Lys Met Pro Leu Ser Ala Ile Val Thr Pro
                        500                 505                 510

Arg Leu Pro Pro Ser Ala Tyr Thr Val
                        515                 520

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Synthetic
      Forward Primer HANS-F3Hpro1k-Fd

<400> SEQUENCE: 5
ccaagcttgg cgcgccgcgg ccgcatttaa atttacaaaa ccatgtgcaa gaatg             55

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      Reverse Primer SNM-F3Hpro-Rv

<400> SEQUENCE: 6
actagtgcta gcacgcgttt tttattttttt cttcacacac ttg                         43

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      Forward Primer SSS-NOSter-Fd

<400> SEQUENCE: 7
gagctcacta gtgtcgacga tcgttcaaac atttggcaat aaag                         44

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      Reverse Primer ESP-NOSter-Rv

<400> SEQUENCE: 8
cgaattcagg cctgtttaaa cgatctagta acatagatga cac                          43
```

<210> SEQ ID NO 9
<211> LENGTH: 61
<212> TYPE: DNA
<213> ORGANISM: Artificial Sequence
<220> FEATURE:
<223> OTHER INFORMATION: Description of Artificial Sequence: Synthetic
      Forward Primer hFAStSw-proCmF3H-Fd

<400> SEQUENCE: 9
aagcttggcc ggcctaggcg cgccaggcct atttaaattt acaaaaccat gtgcaagaat    60
g                                                                   61

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      Forward Primer SSS-terHSP-Fd

<400> SEQUENCE: 10
gagctcacta gtgtcgacat atgaagatga agatgaaat                           39

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      Reverse Primer KESP-terHSP-Rv

<400> SEQUENCE: 11
ggtaccggtc cggaattcgt ttaaacgccc gggccttatc tttaatcata ttccatagtc    60
c                                                                   61

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      Forward Primer IrisDFR_ADH_ORF_Fd

<400> SEQUENCE: 12
caagaaaaat aaatgatgag ccccgttgtc                                     30

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Reverse Primer IrisDFR_NdeI Rv

<400> SEQUENCE: 13
catatgtacc tcccgttcgc ttc                                            23

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      Forward Primer XbaI-ADH-Fd

<400> SEQUENCE: 14
acgcgttcta gagtctattt aactcagtat tc        32

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer IrisDFR_ORF_ADH_Rv

<400> SEQUENCE: 15
ggggctcatc atttattttt cttgatttcc ttcac        35

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      Forward Primer DbDFR_ADH_ORF_Fd

<400> SEQUENCE: 16
caagaaaaat aaatgactgt agaaactgtt tgtg        34

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      Reverse Primer DbDFR_NcoI_Rv

<400> SEQUENCE: 17
ccatggtgta cttatagttg aatcc        25

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer DbDFR_ORF_ADH_Rv

<400> SEQUENCE: 18
ttctacagtc atttattttt cttgatttcc ttcac        35

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      Forward Primer CtDFR_ADH_ORF_Fd

<400> SEQUENCE: 19
caagaaaaat aaatggattc agcagctgaa gtg        33

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      Reverse Primer CtDFR_SphI_Rv

<400> SEQUENCE: 20
gcatgctctc attatgtcaa g        21

```
<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer CtDFR_ORF_ADH_Rv

<400> SEQUENCE: 21
tgctgaatcc atttattttt cttgatttcc ttcac                              35

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      Forward Primer CmF3'H_full_ORF_F

<400> SEQUENCE: 22
atgaacattt tacctttcgt attttatg                                      28

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      Reverse Primer CmF3'H_full_ORF_R

<400> SEQUENCE: 23
ttaaatactt tcatatacgt ggg                                           23

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      Forward Primer CmF3'H_3'-Fd for dsRNA

<400> SEQUENCE: 24
caccccgaac tcattcgtca tccac                                         25

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      Reverse Primer CmF3'H_3'-Rv for dsRNA

<400> SEQUENCE: 25
tcaatccata cgcttcttcc atg                                           23

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      Forward Primer ADH-3'5'GT-Fd

<400> SEQUENCE: 26
caagaaaaat aaatggaaaa caataagcat gtc                                33
```

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      Reverse Primer Hind-Ct3'5'GT-Rv

<400> SEQUENCE: 27
aagcttgcgt ttttagcatc attc                                          24

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer Ct3'5'GT-ADH-Rv

<400> SEQUENCE: 28
attgttttcc atttattttt cttgatttcc ttcac                              35

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      Forward Primer NheI-ADH-Fd2

<400> SEQUENCE: 29
gctagcgtct atttaactca gtattcagaa ac                                 32

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      Reverse Primer Ct3'5'GT-SacI-Rv

<400> SEQUENCE: 30
gagctcttag ctagaggaaa tcatttccac                                    30

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      Forward Primer ADH-CtHCAGT-Fd

<400> SEQUENCE: 31
caagaaaaat aaatggggtc tgaagcttcg tttc                               34

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      Reverse Primer StuI-CtHCAGT-Rv

<400> SEQUENCE: 32
aggcctcatg ttcacaaact tc                                            22

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer CtHCAGT-ADH-Rv

<400> SEQUENCE: 33
ttcagacccc atttattttt cttgatttcc ttcac                              35

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      Forward Primer ADH-CtAT1-Fd

<400> SEQUENCE: 34
caagaaaaat aaatggcagc cttcagttca ac                                 32

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      Reverse Primer Pst-CtAT1-Rv

<400> SEQUENCE: 35
ctgcagcatc tgttctagca taa                                           23

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      Reverse Primer CtAT1-ADH-Rv

<400> SEQUENCE: 36
gaaggctgcc atttattttt cttgatttcc ttcac                              35

<210> SEQ ID NO 37
<211> LENGTH: 250
<212> TYPE: DNA
<213> ORGANISM: Artificial Sequence
<220> FEATURE:
<223> OTHER INFORMATION: Description of Artificial Sequence: Synthetic
      AtHSP18.2 terminator sequence

<400> SEQUENCE: 37
atatgaagat gaagatgaaa tatttggtgt gtcaaataaa aagcttgtgt gcttaagttt    60
gtgttttttt cttggcttgt tgtgttatga atttgtggct ttttctaata ttaaatgaat   120
gtaagatctc attataatga ataaacaaat gtttctataa tccattgtga atgttttgtt   180
ggatctcttc tgcagcatat aactactgta tgtgctatgg tatggactat ggaatatgat   240
taaagataag                                                         250

<210> SEQ ID NO 38
<211> LENGTH: 516
<212> TYPE: DNA
<213> ORGANISM: Artificial Sequence
<220> FEATURE:
<223> OTHER INFORMATION: Description of Artificial Sequence: Synthetic Trigger sequence for F3'H RNAi

<400> SEQUENCE: 38

```
ccgaactcat tcgtcatcca caaatattaa aacaagcccg agaagagata gacgctgtag      60
ttggtcaaga ccggcttgta acagaattgg acttgagcca actaacatac ctccaggctc     120
ttgtgaaaga ggtgtttagg ctccaccctt caacgccact ctccttacca agaatatcat     180
ccgagagttg tgaggtcgat gggtattata tccctaaggg atccacactc ctcgttaacg     240
tgtgggccat tgcgcgagac ccaaaaatgt gggcggatcc tcttgaattt aggccttctc     300
ggtttttacc cggggagaa aagcccggtg ctgatgttag gggaaatgat tttgaagtta      360
taccatttgg ggcaggacga aggatttgtg cgggtatgag cctaggcttg agaatggtcc     420
agttgctcat tgcaacattg gtccaaactt ttgattggga actggctaac gggttagagc     480
cggagatgct caacatggaa gaagcgtatg gattga                               516
```

CREATION OF CHRYSANTHEMUM WITH BLUE FLOWER COLOR

CROSS REFERENCE TO RELATED APPLICATIONS

This application is the National Stage of International Application No. PCT/JP2016/069536 filed Jun. 30, 2016 and claims benefit of Japanese Application No. 2015-133069 filed on Jul. 1, 2015.

SEQUENCE LISTING

The instant application contains a sequence listing which has been submitted in ASCII format via EFS-Web and is hereby incorporated by reference in its entirety. Said ASCII copy, created on Sep. 6, 2018, is named 0472375039-00-US-572396 SL.txt and is 33,093 bytes in size.

TECHNICAL FIELD

The present invention relates to expression cassettes for coexpression of the *Clitoria*-derived anthocyanin 3',5'-O-glucosyltransferase gene (CtA3'5'GT) and *Campanula*-derived flavonoid 3',5'-hydroxylase gene (CamF3'5'H) in chrysanthemum petals, to vectors and transformed chrysanthemum plants containing the expression cassettes, or its inbred or outbred progenies, or their propagules, partial plant bodies (especially cut flowers), processed forms (especially processed cut flowers), tissues or cells, as well as to a method for creating a transformed chrysanthemum plant with a blue flower color.

BACKGROUND ART

*Chrysanthemum*, rose, carnation and lily are industrially important ornamental plants worldwide. *Chrysanthemum*, in particular, is used on a commercial scale in the worldwide ornamental plant industry that is second only to rose, and in Japan, it is the primary ornamental plant, constituting 40% of cut flower production and 30% of production output. With the major ornamental plants mentioned above, however, a problem has existed in that none of the hybridizable related species have wild varieties with blue flower color, and it has therefore been difficult to create varieties with blue flower color by conventional cross-breeding and mutation breeding. Creating completely new blue flower colors leads to new demand for even wider uses of ornamental plants, helps increase production and consumption. Ornamental plants with blue flower colors have therefore been created by genetic engineering methods, and in the case of carnations and roses, have appeared on the market. However, previous flower color modifications attempting to obtain blue flower color have been limited to purple (RHS color chart color hue group: Purple group) or violet (Purple-Violet group, Violet group), whereas it has not been possible to create blue ornamental plants having violet-blue (Violet-Blue group) or blue (Blue group) flower colors. Blue ornamental plants, therefore, are currently limited to Gentian, Delphinium and Oxypetalum, such that there remains a demand to develop techniques for regulating blue expression that would allow creation of ornamental plants with true blue flower colors.

F3'5'H is known as a gene that has been introduced for achieving flower color modification to obtain blue flowers (PTL 1). Introduction of F3'5'H alone, or together with a construct that inhibits endogenous expression of F3'H or DFR, can modify flower color toward blue by converting the anthocyanins of petals to the delphinidin type (FIG. 1). When CamF3'5'H is introduced into *chrysanthemum* (NPL 1 and PTL 2), it is known to alter color to violet (RHS color chart: Violet group 83) or violet (Violet group 88), which has a hue angle of approximately 315° (PTL 3 and NPL 2). It is also known that chrysanthemums obtained by expression of pansy F3'5'H (PTL 1) and inhibition of endogenous F3'H exhibits colors that are purple (Purple-Violet group N82) or violet (Violet group 84) (PTL 4 and NPL 3). Moreover, when A3'5'OMT (PTL 5) and CamF3'5'H are coexpressed to synthesize and accumulate malvidin anthocyanin, more bluer chrysanthemums are obtained that exhibits a hue angle of 305° to 315° (violet)(NPL 4). It has been reported that it is possible to produce transformants with purple or violet flowers from carnation (NPL 5), rose (PTL 6, NPL 6), lily (PTL 7), dahlia (NPL 7) and *Phalaenopsis Orchid* (PTL 8, PTL 9).

While purple or violet flower colors can be created by conventional techniques for producing blue colors using F3'5'H or A3'5'OMT, it has not been possible to create transformants with true blue flower colors that are in the Violet-Blue group or Blue group, exhibiting hue angles of 230° to 290°. Various blue expression mechanisms have also been elucidated (NPL 8), with the reported associated genes including genes that govern: polyacylation of anthocyanins by aromatic organic acids that promote intramolecular association (FIG. 2) (PTL 10, PTL 11, PTL 12, PTL 13, PTL 14, NPL 9), synthesis of anthocyanins and copigments that promote intermolecular association (PTL 15, PTL 16, PTL 17), adjustment of intravacuolar pH (PTL 18, PTL 19), transport of metal ions to vacuoles (PTL 20, NPL 10) and synthesis of metal complex-forming flavones (PTL 21); however, no successful examples exist of obtaining blue colors in the ornamental plants into which these have been transferred. Polyacylation with aromatic organic acids also takes place on the glycosyl-residues of anthocyanins, and a *Clitoria*-derived anthocyanin 3',5'-O-glucosyltransferase gene (CtA3'5'GT) has been reported that governs addition of the glucosyl-residues (PTL 22). Alteration of flower color to blue as a result of transferring the gene into mauve *lobelia* that accumulates delphinidin 3-glucoside has also been reported, and approximately 70% of the anthocyanins accumulated in the petals have the 3' and 5' glucosyl groups modified with aromatic acyl groups, due to the function of endogenous 3'-acyltransferase (3'AT) and 5'AT in *lobelia*. As accumulation of polyacylated anthocyanins is a factor in alteration of *lobelia* flower color to blue, this indicates that creation of blue flower by transformation of CtA3'S'GT gene requires coexpression of aromatic acyltransferase genes such as Ct3'AT (NPL 11). It has in fact been shown that alteration to blue is not achieved if CtA3'S'GT alone is transferred into *chrysanthemum* (Reference Examples 1 and 2).

Thus, multiple genes must be expressed and performed to construct the mechanism of blue color expression, but since functioning in transformed plants is never guaranteed, flowers with true blue colors cannot be created simply by elucidating the blue expression mechanisms and reporting the responsible genes.

CITATION LIST

Patent Literature

[PTL 1] International Patent Publication No. WO2004/020637

[PTL 2] International Patent Publication No. WO2013/157502
[PTL 3] International Patent Publication No. WO2010/122849
[PTL 4] International Patent Publication No. WO2009/062253
[PTL 5] International Patent Publication No. WO2003/062428
[PTL 6] International Patent Publication No. WO2005/017147
[PTL 7] International Patent Publication No. WO2012/036290
[PTL 8] Japanese Patent Publication No. 5285304
[PTL 9] International Patent Publication No. WO2008/136434
[PTL 10] Japanese Patent Publication No. 4853853
[PTL 11] Japanese Patent Publication No. 4982782
[PTL 12] International Patent Publication No. WO1996/025500
[PTL 13] International Patent Publication No. WO2006/046780
[PTL 14] International Patent Publication No. WO2011/016260
[PTL 15] International Patent Publication No. WO2008/156211
[PTL 16] International Patent Publication No. WO2008/156214
[PTL 17] International Patent Publication No. WO2008/156206
[PTL 18] International Patent Publication No. WO2001/14560
[PTL 19] Japanese Patent Publication No. 507282
[PTL 20] Japanese Patent Publication No. 4958247
[PTL 21] International Patent Publication No. WO2012/096307
[PTL 22] Japanese Patent Publication No. 4418865

Non-Patent Literature

[NPL 1] Biosci. Biotechnol. Biochem. (2003) 67:161
[NPL 2] Plant Cell Physiol (2013) 54:1684
[NPL 3] Plant Cell Physiol (2013) 54:1696
[NPL 4] ICP2014:251
[NPL 5] Phytochemistry (2003) 63:15
[NPL 6] Plant Cell Physiol (2007) 48:1589
[NPL 7] Noukou to Engei (2012), October, p. 42, Agricultural Technology Digest Appendix No. 15, 330, 1, 192
[NPL 8] Nat Prod Rep (2009) 26:857
[NPL 9] Plant Cell Physiol (2015) 56:28
[NPL 10] Plos one (2012) 7:e43189
[NPL 11] Japanese Society for Plant Cell and Molecular Biology, Tsukuba Convention—Symposium Lecture Abstracts (2006) p. 40

SUMMARY OF INVENTION

Technical Problem

The problem to be solved by the present invention is to provide transformed *chrysanthemum* plants with blue flower color, or its inbred or outbred progenies, or their propagules, partial plant bodies, tissues or cells.

Solution to Problem

As a result of much diligent research and experimentation conducted with the aim of solving the aforementioned problem, the present inventors have completed this invention upon finding that when the *Clitoria*-derived anthocyanin 3',5'-O-glucosyltransferase gene (CtA3'5'GT) and the *Campanula*-derived flavonoid 3',5'-hydroxylase gene (CamF3'5'H) are coexpressed in *chrysanthemum* petals, it is possible to obtain transformed *chrysanthemum* plants having a previously unobtainable blue flower color (RHS color chart, 5th Edition: Violet-Blue group/Blue group and/or hue angle: 230° to 290°).

Specifically, the present invention provides the following.
[1] An expression cassette comprising:
a first polynucleotide selected from the group consisting of the following (1-a) to (1-e):
(1-a) a polynucleotide comprising the nucleotide sequence listed as SEQ ID NO: 1;
(1-b) a polynucleotide that hybridizes with a polynucleotide comprising the nucleotide sequence complementary to the nucleotide sequence listed as SEQ ID NO: 1 under stringent conditions, the polynucleotide encoding a protein with activity of transferring sugars to the 3'- and 5'-hydroxyl groups of anthocyanins;
(1-c) a polynucleotide encoding a protein comprising the amino acid sequence listed as SEQ ID NO: 2;
(1-d) a polynucleotide encoding an amino acid sequence which is the amino acid sequence listed as SEQ ID NO: 2 with a deletion, substitution, insertion and/or addition of one or more amino acids, and encoding a protein with activity of transferring sugars to the 3'and 5'-hydroxyl groups of anthocyanins; and
(1-e) a polynucleotide encoding an amino acid sequence with at least 90% identity with the amino acid sequence listed as SEQ ID NO: 2, and encoding a protein with activity of transferring sugars to the 3'- and 5'-hydroxyl groups of anthocyanins, and
a second polynucleotide selected from the group consisting of the following (2-a) to (2-e):
(2-a) a polynucleotide comprising the nucleotide sequence listed as SEQ ID NO: 3;
(2-b) a polynucleotide that hybridizes with a polynucleotide comprising the nucleotide sequence complementary to the nucleotide sequence listed as SEQ ID NO: 3 under stringent conditions, the polynucleotide encoding a protein with activity of hydroxylating the 3'- and 5'-positions of flavonoids;
(2-c) a polynucleotide encoding a protein comprising the amino acid sequence listed as SEQ ID NO: 4;
(2-d) a polynucleotide encoding an amino acid sequence which is the amino acid sequence listed as SEQ ID NO: 4 with a deletion, substitution, insertion and/or addition of one or more amino acids, and encoding a protein with activity of hydroxylating the 3'- and 5'-positions of flavonoids; and
(2-e) a polynucleotide encoding an amino acid sequence with at least 90% identity with the amino acid sequence listed as SEQ ID NO: 4, and encoding a protein with activity of hydroxylating the 3'- and 5'-positions of flavonoids.
[2] The expression cassette according to [1], further including a first promoter and first terminator functionally linked to the first polynucleotide, and a second promoter and second terminator functionally linked to the second polynucleotide.
[3] The expression cassette according to [2], wherein the first promoter is *Chrysanthemum* F3H promoter, and the first terminator is *Arabidopsis* HSP terminator or *Agrobacterium* nos terminator.
[4] The expression cassette according to [2] or [3], wherein the second promoter is *Chrysanthemum* F3H promoter, and the second terminator is *Arabidopsis* HSP terminator or *Agrobacterium* nos terminator.

[5] A vector including an expression cassette according to any one of [1] to [4].

[6] A transformed *chrysanthemum* plant including an expression cassette according to any one of [1] to [4], or its inbred or outbred progenies, or their propagules, partial plant bodies, tissue or cells.

[7] A transformed *chrysanthemum* plant, or its inbred or outbred progenies, or their propagules, partial plant bodies, tissue or cells according to [6], in which the *Clitoria*-derived anthocyanin 3',5'-O-glucosyltransferase gene (CtA3'S'GT) and *Campanula*-derived flavonoid 3',5'-hydroxylase gene (CamF3'5'H) are coexpressed in the *chrysanthemum* petals.

[8] A transformed *chrysanthemum* plant, or its inbred or outbred progenies, or their propagules, partial plant bodies, tissue or cells according to [6] or [7], containing delphinidin 3-(6"-malonyl)glucoside-3'5'-diglucoside (ternatin C5) and/or delphinidin 3,3',5'-triglucoside (preternatin C5).

[9] Cut flowers of transformed *chrysanthemum* plants or its inbred or outbred progenies according to [6] to [8], or a processed form created from the cut flowers.

[10] A method for creating transformed *chrysanthemum* plants with a blue flower color, the method comprising a step of introducing:

a first polynucleotide selected from the group consisting of the following (1-a) to (1-e):

(1-a) a polynucleotide comprising the nucleotide sequence listed as SEQ ID NO: 1;

(1-b) a polynucleotide that hybridizes with a polynucleotide comprising the nucleotide sequence complementary to the nucleotide sequence listed as SEQ ID NO: 1 under stringent conditions, the polynucleotide encoding a protein with activity of transferring sugars to the 3'- and 5'-hydroxyl groups of anthocyanins;

(1-c) a polynucleotide encoding a protein comprising the amino acid sequence listed as SEQ ID NO: 2;

(1-d) a polynucleotide encoding an amino acid sequence which is the amino acid sequence listed as SEQ ID NO: 2 with a deletion, substitution, insertion and/or addition of one or more amino acids, and encoding a protein with activity of transferring sugars to the 3'and 5'-hydroxyl groups of anthocyanins; and (1-e) a polynucleotide encoding an amino acid sequence with at least 90% identity with the amino acid sequence listed as SEQ ID NO: 2, and encoding a protein with activity of transferring sugars to the 3'- and 5'-hydroxyl groups of anthocyanins, and/or a second polynucleotide selected from the group consisting of the following (2-a) to (2-e):

(2-a) a polynucleotide comprising the nucleotide sequence listed as SEQ ID NO: 3;

(2-b) a polynucleotide that hybridizes with a polynucleotide comprising the nucleotide sequence complementary to the nucleotide sequence listed as SEQ ID NO: 3 under stringent conditions, the polynucleotide encoding a protein with activity of hydroxylating the 3'- and 5'-positions of flavonoids;

(2-c) a polynucleotide encoding a protein comprising the amino acid sequence listed as SEQ ID NO: 4;

(2-d) a polynucleotide encoding an amino acid sequence which is the amino acid sequence listed as SEQ ID NO: 4 with a deletion, substitution, insertion and/or addition of one or more amino acids, and encoding a protein with activity of hydroxylating the 3'- and 5'-positions of flavonoids; and (2-e) a polynucleotide encoding an amino acid sequence with at least 90% identity with the amino acid sequence listed as SEQ ID NO: 4, and encoding a protein with activity of hydroxylating the 3'- and 5'-positions of flavonoids, into a host.

[11] The method according to [10], which is carried out by transforming a host with an expression cassette according to any one of [1] to [4] or a vector according to [5].

[12] The method according to [11], wherein the blue flower color is in the Blue group or Violet-Blue group of the RHS color chart, and/or has a hue angle of 230° to 290° in the CIEL*a*b* color system.

[13] A transformed *chrysanthemum* plant created by the method according to any one of [10] to [12], or its inbred or outbred progenies, or their propagules, partial plant bodies, tissue or cells.

[14] Cut flowers of transformed *chrysanthemum* plants or its inbred or outbred progenies according to [13], or a processed form created from the cut flowers.

Advantageous Effects of Invention

As a result of analyzing the petal anthocyanins of *chrysanthemum* transformants with blue flower traits obtained according to the invention, the major newly synthesized anthocyanin was found to be delphinidin 3-(6"-malonyl) glucoside-3'5'-diglucoside (ternatin C5), and the trace anthocyanins were found to be delphinidin 3,3',5'-triglucoside (preternatin C5), delphinidin 3-(3",6"-dimalonyl)glucoside-3'5'-diglucoside, delphinidin 3-(6"-malonyl)glucoside-3'-glucoside and cyanidin 3-(6"-malonyl)glucoside-3'-glucoside, whereas there was no detection of anthocyanins polyacylated with aromatic organic acids that produce blue color by intramolecular association. In other words, it is possible according to the invention to impart a blue flower color trait to *chrysanthemum* by simple hydroxylation and glycosylation at the 3'-position and 5'-position of anthocyanins. The present invention is based on a technology for regulating expression of blue color that is completely different from the theory and technology of the prior art, and that does not require the polyacylation by aromatic acyl groups that has been necessary in the past to express blue color.

Figure 1:
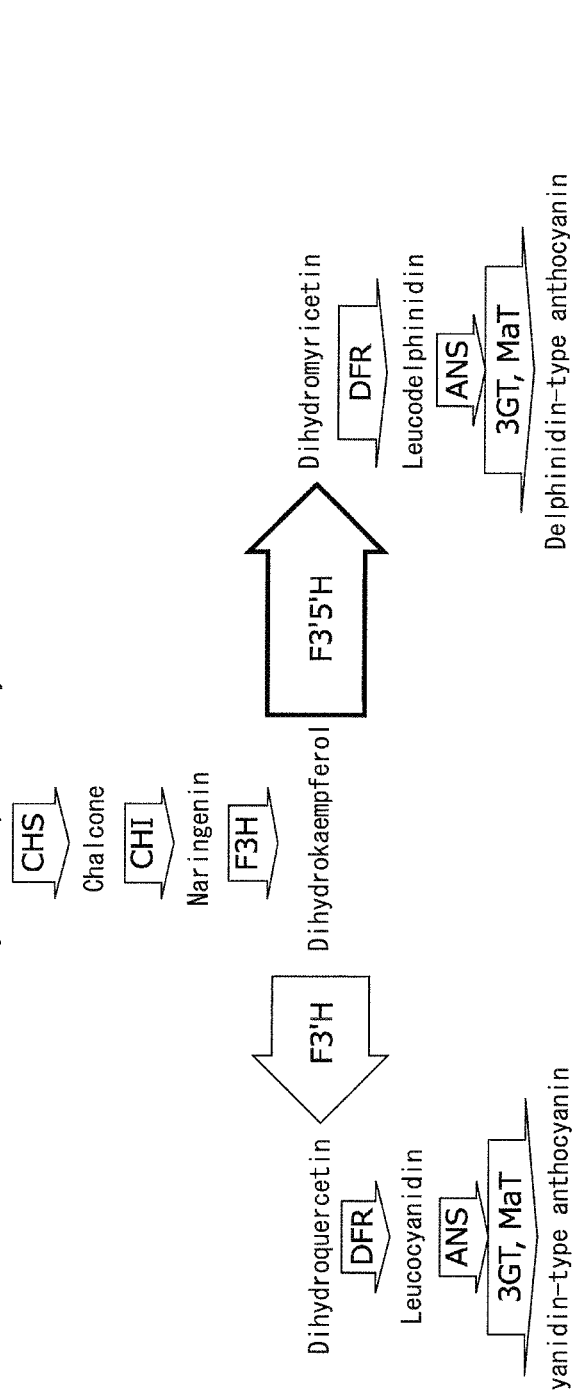
FIG. 1 shows delphinidin glycoside synthesized in *chrysanthemum* petals by F3'5'H introduction.
Figure 1:
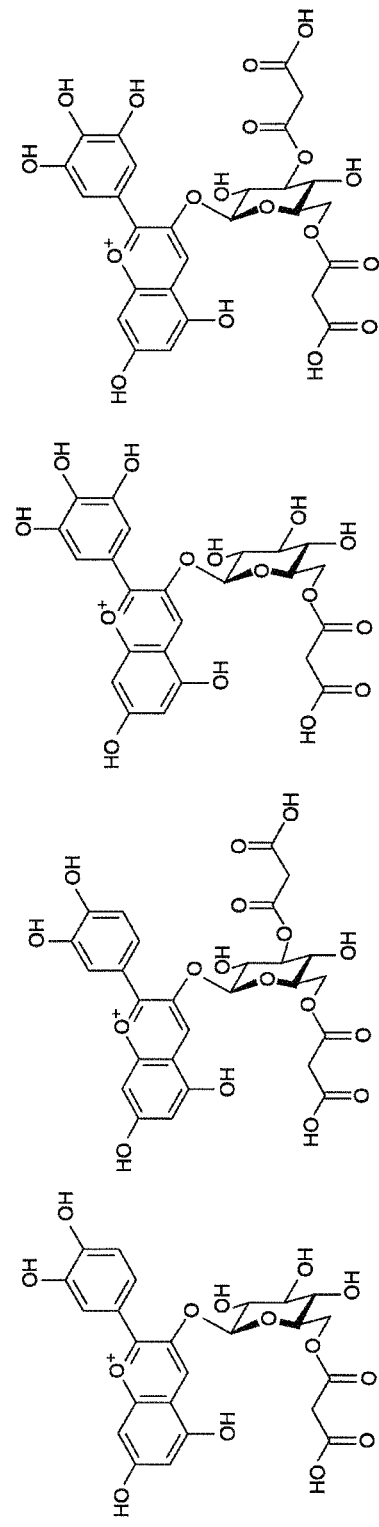

The present invention relates to an expression cassette comprising:

a first polynucleotide selected from the group consisting of the following (1-a) to (1-e):

(1-a) a polynucleotide comprising the nucleotide sequence listed as SEQ ID NO: 1;

(1-b) a polynucleotide that hybridizes with a polynucleotide comprising the nucleotide sequence complementary to the nucleotide sequence listed as SEQ ID NO: 1 under stringent conditions, the polynucleotide encoding a protein with activity of transferring sugars to the 3'- and 5'-hydroxyl groups of anthocyanins;

(1-c) a polynucleotide encoding a protein comprising the amino acid sequence listed as SEQ ID NO: 2;

(1-d) a polynucleotide encoding an amino acid sequence which is the amino acid sequence listed as SEQ ID NO: 2 with a deletion, substitution, insertion and/or addition of one or more amino acids, and encoding a protein with activity of transferring sugars to the 3'and 5'-hydroxyl groups of anthocyanins; and (1-e) a polynucleotide encoding an amino acid sequence with at least 90% identity with the amino acid sequence listed as SEQ ID NO: 2, and encoding a protein with activity of transferring sugars to the 3'- and 5'-hydroxyl groups of anthocyanins, and a second polynucleotide selected from the group consisting of the following (2-a) to (2-e):

(2-a) a polynucleotide comprising the nucleotide sequence listed as SEQ ID NO: 3;

(2-b) a polynucleotide that hybridizes with a polynucleotide comprising the nucleotide sequence complementary to the nucleotide sequence listed as SEQ ID NO: 3 under stringent conditions, the polynucleotide encoding a protein with activity of hydroxylating the 3'- and 5'-positions of flavonoids;

(2-c) a polynucleotide encoding a protein comprising the amino acid sequence listed as SEQ ID NO: 4;

(2-d) a polynucleotide encoding an amino acid sequence which is the amino acid sequence listed as SEQ ID NO: 4 with a deletion, substitution, insertion and/or addition of one or more amino acids, and encoding a protein with activity of hydroxylating the 3'- and 5'-positions of flavonoids; and (2-e) a polynucleotide encoding an amino acid sequence with at least 90% identity with the amino acid sequence listed as SEQ ID NO: 4, and encoding a protein with activity of hydroxylating the 3'- and 5'-positions of flavonoids.

Throughout the present specification, the term "polynucleotide" refers to DNA or RNA, and in the expression cassette of the invention, the first polynucleotide encodes *Clitoria*-derived anthocyanin 3',5'-O-glucosyltransferase or its analog, and the second polynucleotide encodes *Campanula*-derived flavonoid 3',5'-hydroxylase or its analog. Here, "encodes" means that it allows expression of the protein of interest in a state in which it exhibits its activity. Also, the term "encodes" includes both encoding a structural sequence (exon) that is a continuous section of the protein of interest, and encoding via an intervening sequence (intron).

Anthocyanin 3',5'-O-glucosyltransferase is an enzyme that catalyzes the reaction of successive transfer of sugars to the hydroxyl groups at the 3'- and 5'-positions of anthocyanin, and it is found in blue flower petals of *Clitoria*. *Clitoria* petals are thought to exhibit their blue color due to accumulation of polyacylated delphinidins, which have the hydroxyl groups at both the 3'- and 5'-positions of the anthocyanin glycosylated, and have also undergone further modification by aromatic acyl groups. Flavonoid 3',5'-hydroxylase is an enzyme that hydroxylates the 3'- and 5'-positions of flavonoids, and it has been found in *Campanula* blue flower petals. It is thought that large amounts of delphinidin-type anthocyanins accumulate in petals in which F3'5'H is expressed, thus allowing mauve, purple, violet and blue colors to be exhibited. However, the *chrysanthemum* plant has neither a gene coding for anthocyanin 3',5'-O-glucosyltransferase nor a gene coding for flavonoid 3',5'-hydroxylase. Furthermore, because *chrysanthemum* has higher polyploidy, specifically hexaploidy, and a large genome size, its transformation efficiency is low and silencing (inactivation) of the transferred genes also often occurs, such that is not easy to obtain a gene recombinant *chrysanthemum* exhibiting stable expression by transfer of these genes. Moreover, blueness is not produced in the petals even when CtA3'5'GT or CamF3'5'H has been successfully transferred, and therefore no transformed *chrysanthemum* plants with blue flower color are known at the current time.

As used herein, the term "stringent conditions" refers to conditions that allow specific binding between a polynucleotide or oligonucleotide and genomic DNA in a selective and detectable manner. Stringent conditions are defined by an appropriate combination of salt concentration, organic solvent (for example, formamide), temperature and other known conditions. Specifically, stringency is increased by reducing the salt concentration, increasing the organic solvent concentration or raising the hybridization temperature. Stringency is also affected by the rinsing conditions after hybridization. The rinsing conditions are defined by the salt concentration and temperature, and stringency of rinsing is increased by reducing the salt concentration and raising the temperature. Therefore, the term "stringent conditions" means conditions such that specific hybridization takes place only between nucleotide sequences with high identity, such as a degree of "identity" between the nucleotide sequences of about 80% or greater, preferably about 90% or greater, more preferably about 95% or greater, even more preferably 97% or greater and most preferably 98% or greater, on average. The "stringent conditions" may, for example, a temperature of 60° C. to 68° C., a sodium concentration of 150 to 900 mM and preferably 600 to 900 mM, and a pH of 6 to 8, with specific examples including hybridization under conditions of 5×SSC (750 mM NaCl, 75 mM trisodium citrate), 1% SDS, 5×Denhardt solution, 50% formaldehyde, 42° C., and rinsing under conditions of 0.1×SSC (15 mM NaCl, 1.5 mM trisodium citrate), 0.1% SDS, 55° C.

The hybridization may be carried out by a method that is publicly known in the field or a similar method, such as the method described in Current protocols in molecular biology (edited by Frederick M. Ausubel et al., 1987). When a commercially available library is to be used, it may be carried out according to the method described in the accompanying directions for use. The gene selected by such hybridization may be naturally derived, such as plant-derived or non-plant-derived. The gene selected by the hybridization may be cDNA, genomic DNA or chemically synthesized DNA.

The phrase "amino acid sequence with a deletion, substitution, insertion and/or addition of one or more amino acids" means an amino acid sequence having a deletion, substitution, insertion and/or addition of any number of amino acids which may be 1 to 20, preferably 1 to 5 and more preferably 1 to 3. Site-specific mutagenesis is a useful genetic engineering method as it allows introduction of specific mutations into specified sites, and it may be carried out by the method described in Molecular Cloning: A Laboratory Manual, 2$^{nd}$ Ed., Cold Spring Harbor Laboratory Press, Cold Spring Harbor, N.Y., 1989. By expressing the mutant DNA using a suitable expression system, it is possible to obtain a protein comprising an amino acid sequence with a deletion, substitution, insertion and/or addition of one or several amino acids.

A polynucleotide can be obtained by a method that is publicly known to those skilled in the art, such as a method of chemical synthesis using the phosphoramidite method, or a nucleic acid amplification method using a plant nucleic acid specimen as template, and primers designed based on the nucleotide sequence of the target gene.

Throughout the present specification, the term "identity" means, for polypeptide sequences (or amino acid sequences) or polynucleotide sequences (or nucleotide sequences), the quantity (number) of amino acid residues or nucleotides composing them that can be determined to be identical between the two chains, in the sense of mutual agreement between them, meaning the degree of sequence correlation between two polypeptide sequences or two polynucleotide sequences, and this "identity" can be easily calculated. Numerous methods are known for measuring identity between two polynucleotide sequences or polypeptide sequences, and the term "identity" is well known to those skilled in the art (for example, see Lesk, A. M. (Ed.), Computational Molecular Biology, Oxford University Press, New York, (1988); Smith, D. W. (Ed.), Biocomputing: Informatics and Genome Projects, Academic Press, New York, (1993); Gribin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991) and elsewhere).

Also, the numerical values for "identity" used in the present specification, unless otherwise specified, may be the numerical values calculated using an identity search program known to those skilled in the art, but they are preferably numerical values calculated using the ClustalW program of MacVector Application (version 9.5, Oxford Molecular Ltd., Oxford, England). According to the invention, the degree of "identity" between amino acid sequences is, for example, about 80% or greater, preferably about 90% or greater, more preferably about 95% or greater, even more preferably about 97% or greater and most preferably about 98% or greater.

A gene with a natural nucleotide sequence can be obtained by analysis using a DNA sequencer, for example. Also, a polynucleotide encoding an enzyme having a modified amino acid sequence can be synthesized using common site-specific mutagenesis or PCR, based on a polynucleotide having the natural nucleotide sequence. For example, a polynucleotide fragment to be modified may be obtained by restriction enzyme treatment of natural cDNA or genomic DNA, and used as template for site-specific mutagenesis or PCR using primers with the desired mutation, to obtain a polynucleotide fragment having the desired modification. The polynucleotide fragment having the mutation may then be linked with a DNA fragment encoding another portion of the target enzyme.

Alternatively, in order to obtain a polynucleotide encoding an enzyme comprising a shortened amino acid sequence, for example, an amino acid sequence that is longer than the target amino acid sequence, such as a polynucleotide encoding the full length amino acid sequence, may be cut with a selected restriction enzyme, and if the resulting polynucleotide fragment does not encode the entire target amino acid sequence, a DNA fragment comprising the missing portion of the sequence may be synthesized and linked with it.

By expressing the obtained polynucleotide using a gene expression system in *Escherichia coli* or yeast and measuring the enzyme activity, it is possible to confirm that the obtained polynucleotide encodes a protein with the desired activity. By then expressing the polynucleotide, it is possible to obtain a protein with the desired activity as a polynucleotide product. Alternatively, a protein with activity of transferring sugars to the hydroxyl groups at the 3'- and 5'-positions of anthocyanins can be obtained using an antibody for a polypeptide comprising the amino acid sequence listed as SEQ ID NO: 2, and such an antibody may also be used for cloning of a polynucleotide encoding a protein with activity of transferring sugars to the 3'- and 5'-hydroxyl groups of anthocyanins, that has been derived from another organism. Likewise, a protein with activity of hydroxylating the 3'- and 5'-positions of flavonoids can be obtained using an antibody for a polypeptide comprising the amino acid sequence listed as SEQ ID NO: 4, and such an antibody may also be used for cloning of a polynucleotide encoding a protein with activity of hydroxylating the 3'- and 5'-positions of flavonoids, that has been derived from another organism.

As used herein, "expression cassette" means a polynucleotide fragment optionally having a promoter and terminator linked to the polynucleotide. The expression cassette of the invention may further include a first promoter and/or first terminator functionally linked to a first polynucleotide encoding *Clitoria*-derived anthocyanin 3',5'-O-glucosyltransferase or an analog thereof, and a second promoter and/or second terminator functionally linked to a second polynucleotide encoding *Campanula*-derived flavonoid 3',5'-hydroxylase or an analog thereof.

The promoters and terminators to be used in the expression cassette of the invention are not particularly restricted so long as they can cause coexpression of the *Clitoria*-derived anthocyanin 3',5'-O-glucosyltransferase gene (CtA3'5'GT) and *Campanula*-derived flavonoid 3',5'-hydroxylase gene (CamF3'5'H) in *chrysanthemum* petals, but the first promoter is preferably *Chrysanthemum* F3H promoter and especially *Chrysanthemum* F3H1k or *Chrysanthemum* F3H500, the first terminator is preferably *Arabidopsis* HSP terminator or *Agrobacterium* nos terminator, the second promoter is preferably *Chrysanthemum* F3H promoter, and the second terminator is preferably *Arabidopsis* HSP terminator or *Agrobacterium* nos terminator.

The present invention relates to a (recombinant) vector, and especially an expression vector, including the aforementioned expression cassette, and to *chrysanthemum* plants transformed by the vector.

The present invention further relates to a transformed *chrysanthemum* plant obtained by transferring into a host a first polynucleotide encoding a protein with activity of transferring sugars to the 3'- and 5'-hydroxyl groups of anthocyanins and/or a second polynucleotide encoding a protein with activity of hydroxylating the 3'- and 5'-positions of flavonoids, as exogenous polynucleotides, or to its inbred or outbred progenies, or their propagules, partial plant bodies, tissues or cells. Transfer of the polynucleotides can be achieved by transformation of a host with an expression cassette or vector of the invention. Alternatively, when either the *Clitoria*-derived anthocyanin 3',5'-O-glucosyl-transferase gene (CtA3'5'GT) or *Campanula*-derived flavonoid 3',5'-hydroxylase gene (CamF3'5'H) is being expressed in the host, it is sufficient to transfer only the first polynucleotide or second polynucleotide into the host.

In order to transfer a polynucleotide into a plant and express the polynucleotide in a constitutive or tissue-specific manner, any method publicly known to those skilled in the art under current technical standards, such as the *Agrobacterium* method, binary vector method, electroporation method, PEG method or particle gun method, may be used.

Throughout the present specification, the term "*chrysanthemum* plant" (also simply "*chrysanthemum*") means a plant of the genus *Chrysanthemum* of the Asteraceae family. The genus *Chrysanthemum* includes *C. japonense*, *C. zawadskii* var. *latilobum*, *C. indicum* var. *procumbens*, *C. zawadskii* and *C. pacificum*, which are commonly known as wild chrysanthemums. It also includes diversely cross-bred varieties such as spray *chrysanthemum*, ogiku and kogiku, which are obtained by hybridization between wild varieties and commonly known as *Chrysanthemum morifolium* or cultivated chrysanthemums (*Chrysanthemum morifolium*; previously: *Dendranthema grandiflora*, *Chrysanthemum grandiflorum*)). According to the invention, there are no particular restrictions on the types of *chrysanthemum* plants that may be used as hosts, and various *chrysanthemum* varieties and lines that have been selected and bred for various dressing purposes, such as spray mums, disbud mums and pot mums, or various *chrysanthemum* varieties and lines that have different flowers, such as anemone mums, decorative mums, pompon mums and daisy mums (single blooms) may be used. The examples described below exhibit blue flower colors in the Blue group or Violet-Blue group according to the RHS Color Chart, 5th Edition (Royal Horticultural Society), or with a CIEL*a*b* color system hue angle of 230° to 290° as obtained by measurement with a Chroma Meter or color shade spectrometer, being exhibited in hosts of diverse varieties and lines, such as Sei Shawl (S39), Taihei, T27, Sei Arabella (T34), T37, Candela Tierra, T10, T24, T44, and T57 (average hue angle: ~55° to 0° (360°) to ~337°; RHS color chart: 49C-D Red group to Red-Purple group to 75B-C Purple group).

The major anthocyanins in *Chrysanthemum* plants used as hosts that exhibit flower colors in the Red group, Red-Purple group and Purple group are cyanidin 3-(6"-malonyl)glucoside and cyanidin 3-(3",6"-dimalonyl)glucoside. The major anthocyanin of transformed *chrysanthemum* obtained by transfer and functioning of the *Campanula* F3'5'H gene is delphinidin 3-(6"-malonyl)glucoside, with trace amounts of delphinidin 3-(3",6"-dimalonyl)glucoside. Cyanidin 3-(6"-malonyl)glucoside and cyanidin 3-(3",6"-dimalonyl)glucoside both have a visible absorption maximum wavelength of 518 nm, while that of delphinidin 3-(6"-malonyl)glucoside is 527 nm. Transformed *chrysanthemum* that includes mainly delphinidin 3-(6"-malonyl)glucoside exhibits a purple to violet color, due to this shift toward the long wavelength end. On the other hand, it has been demonstrated that blue *chrysanthemum*, created by expressing both the *Campanula* F3'5'H gene and the *Clitoria* A3'5'GT gene in *chrysanthemum* petals, includes delphinidin 3-(6"-malonyl)glucoside-3',5'-diglucoside (ternatin C5) as the major pigment, while also including as trace pigments delphinidin 3,3',5'-triglucoside (preternatin C5), delphinidin 3-(3",6"-dimalonyl)glucoside-3'5'-diglucoside and delphinidin 3-(6"-malonyl)glucoside-3'-glucoside, which are demalonylated forms of ternatin C5, and cyanidin 3-(6"-malonyl)glucoside-3'-glucoside. Delphinidin 3-(6"-malonyl)glucoside-3',5'-diglucoside (ternatin C5), which is the major anthocyanin of blue *chrysanthemum*, has a visible absorption maximum wavelength of 512 nm, which is shifted further toward the short wavelength end than cyanidin 3-(6"-malonyl)glucoside, the major anthocyanin in the original red and pink colors. This means that delphinidin 3-(6"-malonyl)glucoside-3',5'-diglucoside (ternatin C5), though being redder than the original pigment, renders the petals of *chrysanthemum* blue. Thus, while it is believed that the petals are expressing blue color due to the interaction between delphinidin 3-(6"-malonyl)glucoside-3',5'-diglucoside (ternatin C5) and the endogenous copigment substances in *chrysanthemum*, as of the current time, no examples have been reported of blue color expression by red anthocyanins in which both the 3'- and 5'-hydroxyl groups of the anthocyanin B-ring have been glycosylated, such as delphinidin 3-(6"-malonyl)glucoside-3',5'-diglucoside (ternatin C5), and the present invention is based on a technique for regulating expression of blue color that is completely different from the theory and technology of the prior art, and that does not require the polyacylation by aromatic acyl groups that has been necessary in the past to express blue color.

The present invention still further relates to cut flowers of transformed *chrysanthemum* plants obtained as described above or its inbred or outbred progenies, or a processed form created from the cut flowers (especially processed cut flowers). The processed cut flowers referred to here include pressed flowers formed using cut flowers, or preserved flowers, dry flowers or resin sealed products, with no limitation to these.

The present invention will now be explained in greater detail by examples.

The molecular biological methods used were based on Molecular Cloning (Sambrook and Russell, 2001), unless otherwise specified. Absence of errors in the DNA sequences of the amplified PCR products and the plasmids obtained by cloning was confirmed based on the nucleotide sequences.

EXAMPLES

Example 1: Introduction of pB423 into *Chrysanthemum* Variety "Taipei" (Coexpression of *Clitoria* A3'5'GT Gene Under the Control of *Chrysanthemum* F3H Promoter 1k and *Agrobacterium* Nos Terminator and *Campanula* F3'5'H Gene Under the Control of *Chrysanthemum* F3H Promoter 1k and *Arabidopsis* HSP Terminator)

[1] Vector Assembly

PCR was conducted using pBluescript SK-gF3H9 (Kanno et al. (2001), J. Japan. Soc. Hort. Sci. 70 (vol. 2) 193) as template, and HANS-F3Hpro1k-Fd (5'-CCAAGCTTGGCGCGCCGCGGCCGCATTTAAAT<u>TTACAAAACCATGT</u>

<u>GCAAGAATG</u>-3';

underline indicates the sequence annealing with DNA containing the F3H promoter region; SEQ ID NO: 5) and SNM-F3Hpro-Rv (5'-ACTAGTGCTAGCACGCGT <u>TTTTTATTTTTCTTCACACACTTG</u>-3';

underline indicates the sequence annealing with DNA containing the F3H promoter region; SEQ ID NO: 6) as primers, to amplify a DNA fragment containing CmF3H promoter 1k having HindIII, AscI, NotI and SwaI restriction enzyme sites added to the 5'-end and SpeI and NheI restriction enzyme sites added to the 3'-end, and the fragment was then used for TA cloning in pGEM-T easy (Promega) and digested with HindIII and SpeI to obtain a DNA fragment.

PCR was conducted using pBI221 as template and SSS-NOSter-Fd (5'-GAGCTCACTAGTGTCGAC

GATCGTTCAAACATTTGGCAATAAAG-3';

underline indicates the sequence annealing with DNA containing the NOS terminator region; SEQ ID NO: 7) and ESP-NOSter-Rv (5'-CGAATTCAGGCCTGTTTAAAC

GATCTAGTAACATAGATGACAC-3';

underline indicates the sequence annealing with DNA containing the NOS terminator region; SEQ ID NO: 8) as primers, to amplify a DNA fragment containing the *Agrobacterium* nos terminator having SacI, EcoICRI (Ecl136II), SpeI and SalI restriction enzyme sites added to the 5'-end and PmeI, SrfI and EcoRI restriction enzyme sites added to the 3'-end, and the fragment was then used for TA cloning in pCR2.1 (Invitrogen) and digested with SacI and EcoRI to obtain a DNA fragment containing *Agrobacterium* nos terminator.

The restriction enzyme site-added CmF3H promoter 1k DNA fragment and NOS terminator DNA fragment were inserted in place of the HindIII-XbaI region containing the CaMV 35S promoter and the SacI-EcoRI region containing the NOS terminator from pBI221, and upon digestion with HindIII and EcoRI, the obtained HANS-CmF3Hp1k:GUS: NOSt-PSE cassette was linked with a plasmid fragment obtained by digestion of pSPORT2 (Invitrogen) with HindIII and EcoRI, to obtain pMCE5 as an entry vector for coupling of the gene expression cassette in a continuous manner with the binary vector.

Plasmid pMCE5-2 was constructed, wherein the 5'-end restriction enzyme site of the promoter of the entry vector pMCE5 for linkage of the gene expression cassette in a continuous manner with the binary vector, was modified to HindIII, FseI, AscI, StuI, SwaI, and the terminator was switched from the *Agrobacterium* nos terminator to the *Arabidopsis* Heat Shock Protein (HSP) 18.2 terminator (AtHSPter, Plant Cell Physiol. 51(2): 328-332 (2010); SEQ ID NO: 37). The EcoICRI, SacI, SpeI and SalI restriction enzyme sites were added to the 5'-end and SrfI, SmaI, PmeI, EcoRI, KpnI to the 3'-end of AtHSPter.

PCR was conducted using pBluescript SK-gF3H9 as template and hFAStSw-proCmF3H-Fd (5'-AAGCTTGGCCGGCCTAGGCGCGCCAGGCCTATTTAAATTTACAAAA

CCATGTGCAAGAATG-3';

underline indicates the sequence annealing with DNA of the F3H promoter region; SEQ ID NO: 9) and SNM-F3Hpro-Rv (5'-ACTAGTGCTAGCACGCGT

TTTTTATTTTTTCTTCACACACTTG-3';

underline indicates the sequence annealing with DNA of the F3H promoter region; SEQ ID NO: 6) as primers, and the amplified DNA fragment was cloned in pCR-BluntII-TOPO (Life Technologies) to obtain pCR-FASS-CmF3Hpro1k. The FASS-CmF3Hpro1k DNA fragment obtained by digestion of this plasmid with HindIII and NheI and the plasmid DNA fragment obtained by digestion of pMCE5 with HindIII and SpeI were linked to obtain pMCE5-FASS.

PCR was conducted using pCR-HSP as template and SSS-terHSP-Fd (5'-GAGCTCACTAGTGTCGACATATGAAGATGAAGATGAAAT-3';

underline indicates DNA sequence annealing t AtHSPter; SEQ ID NO: 10) and KESP-terHSP-Rv (5'-GGTACCGGTCCGGAATTCGTTTAAACGCCCGGGCCTTATCTTTAA

TCATATTCCATAGTCC-3';

underline indicates DNA sequence annealing to AtHSPter; SEQ ID NO: 11) as primers, and the amplified DNA fragment was cloned in pCR-BluntII-TOPO (Life Technologies) to obtain pCR-SSS-AtHSPter-PSEK. An AtHSPter DNA fragment obtained by digesting this plasmid with KpnI and SacI was linked with a vector DNA fragment obtained by digesting pMCE5-FASS with SacI and KpnI, to obtain pMCE5-2.

A plasmid DNA fragment obtained by digesting pMCE5-2 with NheI and EcoICRI was linked with an approximately 1.7 kb DNA fragment obtained by blunting the ends of a KpnI digestion product of pCR ADHNF-*Campanula* F3'5'H (Japanese Patent No. 5697040), and then digesting with XbaI, to obtain pMCE5-2 ADHNF-CamF3'S'H. An expression cassette DNA fragment obtained by digesting this plasmid with AscI and PmeI was linked with a binary vector DNA fragment obtained by digesting pB249 obtained in Reference Example 2 with AscI and SwaI, to obtain pB423 (pBCtA3'5'GT+CamF3'5'H).

[2] Obtaining Transformants and Measuring Flower Color

Using pB423-transformed *Agrobacterium* EHA105 (Hood, E. E. et al. (1993) New *Agrobacterium* helper plasmids for gene transfer to plants. Transgenic Res. 2, 208-218, provided by Dr. Elizabeth E. Hood), the pink medium-sized *chrysanthemum* variety "Taihei" (sampled genetic resource maintained by aseptic culture at the NARO Institute of Floricultural Science) was transformed to obtain 46 transformant lines. As a result of color measurement with a spectroscopic colorimeter (CD100, Yokogawa Electric Corp.) and an RHS color chart, alteration of flower color toward blue was found in 26 lines (57%). Measurement with the spectroscopic colorimeter was conducted on a minimum of 3 petals, and the average was calculated. The hue angle (Hue°) was calculated as $\arctan(b^*/a^*)$, and the chroma ($C^*$ value) was calculated as $(a^2+b^2)^{1/2}$. In 22 lines (48% of the total), blue with a hue angle of ≤290° was exhibited, and in 22 lines (48% of the total), flower color in the Violet-Blue group of the RHS color chart was exhibited. Plasmid pB423 expressing this CamF3'5'H under the control of *Chrysanthemum* F3H promoter and *Arabidopsis* HSP terminator and also expressing *Clitoria* A3'5'GT under the control of *Chrysanthemum* F3H promoter is the simplest gene transfer construct, and blue *chrysanthemum* was obtained at a high proportion of 48%. Also, by using *Arabidopsis* HSP terminator as the terminator for the *Campanula*-derived F3'5'H gene, blue *chrysanthemum* was created at a higher proportion than when using *Agrobacterium* nos terminator (Examples 4, 12-18).

Figure 3:
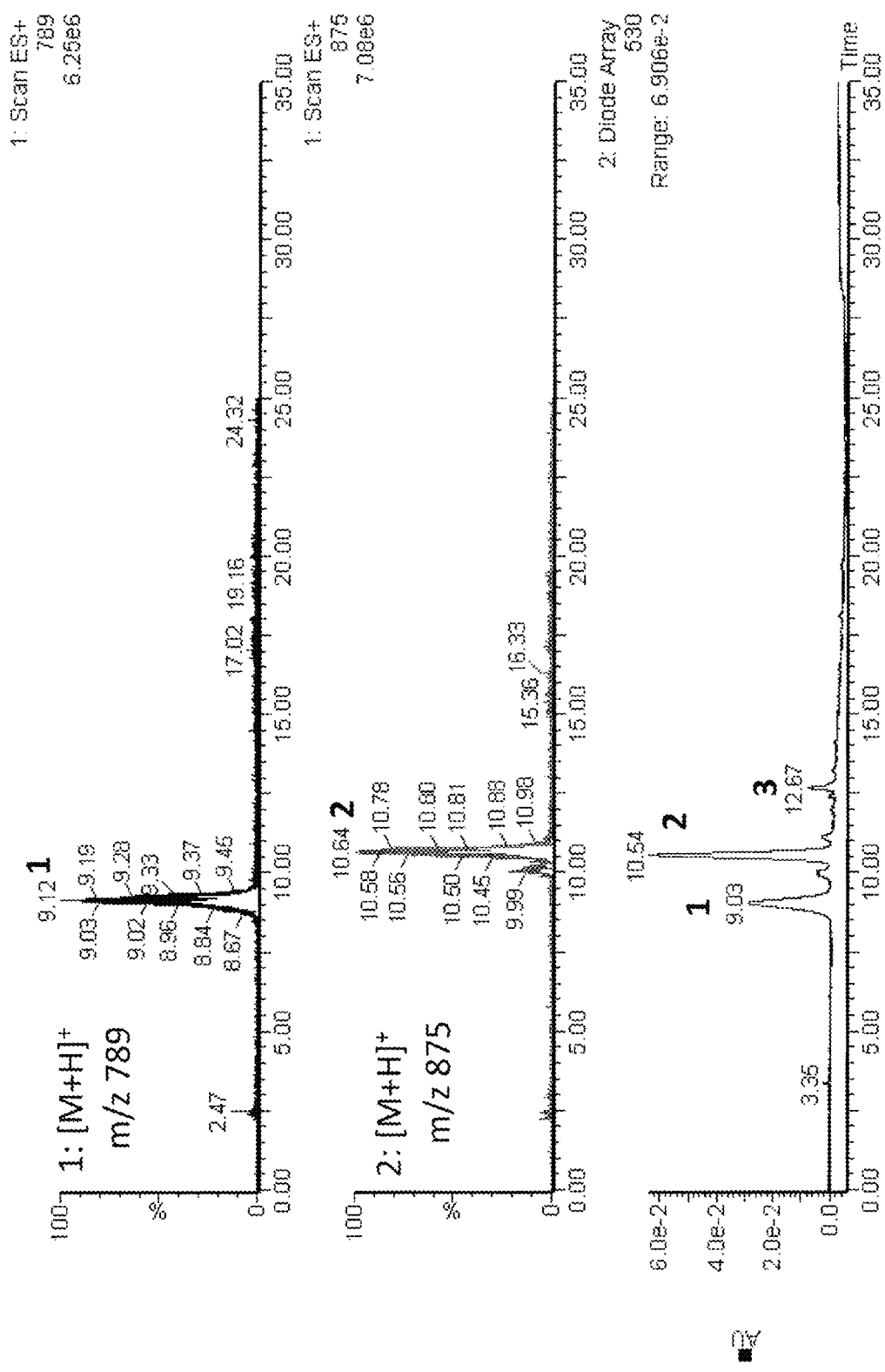
FIG. 3 shows HPLC-MS analysis results for the major anthocyanins in blue *chrysanthemum* petals.
Figure 4:
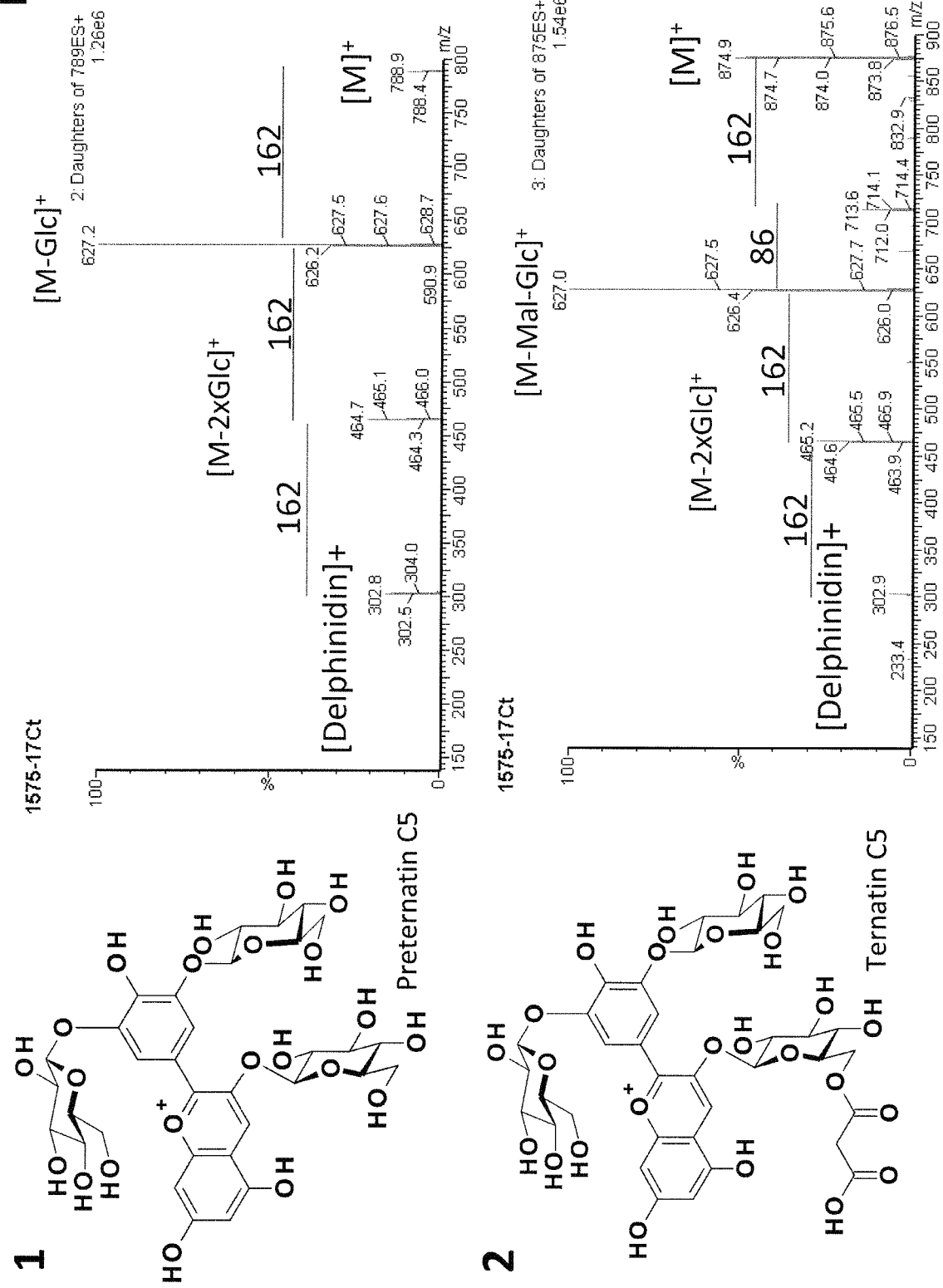
FIG. 4 shows the chemical structure and LC-MS/MS analysis results for the major anthocyanins in blue *chrysanthemum* petals.

The anthocyanins in the *chrysanthemum* variety "Taihei" which had been imparted with a blue trait were analyzed by liquid chromatography/mass spectrometry (ACQUITY UPLC/tandem quadrupole MS ACQUITY TQD, Japan Waters, K.K.). Solvent A was 1% formic acid-containing distilled water, and solvent B was 1% formic acid-containing acetonitrile. Gradient elution was performed with the solvent flow rate at 0.1 ml/min, and solvent B at from 0% to 5% for 0-5 minutes and at from 5% to 35% for 5-20 minutes, and subsequently maintained at 35% for 20-25 minutes. The column used was an ACQUITY UPLC BEH C18 1.7 μm (2.1 i.d.×100 mm; Japan Waters, K.K.) connected to a VanGuard guard column (Japan Waters, K.K.), and analysis was performed with a column temperature of 35° C. As a result of analysis of the spectral data obtained by a photodiode array at 530 nm, peaks for anthocyanin were observed at retention times of approximately 9 minutes (peak 1), 10.5 minutes (peak 2) and 12.7 minutes (peak 3) (FIG. 3). The masses ([M+H]$^+$) were m/z 875 for the predominant peak 2, m/z 789 for peak 1 and m/z 697 for peak 3. Moreover, the results of absorption spectrometry of each peak, in comparison with a sample prepared from *Clitoria*, and LC-MS/MS analysis (FIG. 4) showed that peak 1 was delphinidin 3,3',5'-triglucoside (preternatin C5), peak 2 was delphinidin 3-(6"-malonyl)glucoside-3',5'-diglucoside (ternatin C5) and peak 3 was cyanidin 3-(6"-malonyl)glucoside-3'-glucoside, and that modification to the desired anthocyanin structure had been achieved by expression of the transferred genes *Campanula* F3'S'H and *Clitoria* A3'S'GT. The chrysanthemums expressed blue color by accumulation of the major pigments delphinidin 3-(6"-malonyl)glucoside-3',5'-diglucoside (ternatin C5) and delphinidin 3,3',5'-triglucoside (preternatin C5).

Accumulation of the newly synthesized anthocyanins delphinidin 3-(6"-malonyl)glucoside-3',5'-diglucoside (ternatin C5), delphinidin 3,3',5'-triglucoside (preternatin C5) and cyanidin 3-(6"-malonyl)glucoside-3'-glucoside was detected by thin-layer chromatography (TLC). After spotting a 10% acetic acid petal extract at a location 1.5 cm below a TLC Cellulose Glass Plate (10×20 cm, Millipore) and air-drying, development was carried out to a location 7 cm from the origin, in a developing tank containing BAW developing solvent (butanol:acetic acid:water=4:1:2 (v/v/v)). After development, the plate was dried and detection was performed under a fluorescent lamp and UV light (CSN-15AC, Cosmo Bio Co., Ltd., 254/360 nm). The Rf value of each anthocyanin was as follows. Delphinidin 3-(6"-malonyl)glucoside-3',5'-diglucoside (ternatin C5): 0.15, delphinidin 3,3',5'-triglucoside (preternatin C5): 0.11, cyanidin 3-(6"-malonyl)glucoside-3'-glucoside: 0.30.

The measured values for the transformants confirmed to have modification of flower color toward blue are shown below in Table 1.

TABLE 1

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| Ohira wild type * | 79.5 | 9.7 | -2.0 | 356.6 | 11.1 | 65B, N74C, 75B | Red-Purple/ Purple |
| | | | | Ohira transformants | | | |
| 1728-05 | 74.0 | 8.6 | -6.6 | 322.4 | 10.8 | N82C-D | Purple-Violet |
| 1728-06 | 60.8 | 3.4 | -19.6 | 279.9 | 19.9 | 97A | Violet-Blue |
| 1728-07 | 57.4 | 4.1 | -20.7 | 281.3 | 21.1 | 96B | Violet-Blue |
| 1728-10 | 61.3 | 6.9 | -20.7 | 288.4 | 21.9 | 94B | Violet-Blue |
| 1728-12 | 63.3 | 3.6 | -19.9 | 280.3 | 20.3 | 95C | Violet-Blue |
| 1728-13 | 61.1 | 5.4 | -18.9 | 285.9 | 19.7 | 94C-D | Violet-Blue |
| 1728-17 | 68.3 | 1.1 | -13.1 | 274.9 | 13.1 | 96D | Violet-Blue |
| 1728-21 | 63.4 | 3.8 | -20.7 | 280.3 | 21.0 | 97A | Violet-Blue |
| 1728-23 | 69.6 | 3.5 | -13.1 | 284.9 | 13.6 | 92B-C | Violet-Blue |
| 1728-27 | 65.4 | 2.9 | -13.8 | 281.7 | 14.1 | 96C-D | Violet-Blue |
| 1728-28 | 59.9 | 4.2 | -18.6 | 282.8 | 19.1 | 96C-D | Violet-Blue |
| 1728-29 | 73.3 | 3.1 | -7.6 | 292.6 | 8.2 | 85C-D | Violet |
| 1728-30 | 66.4 | 4.5 | -13.8 | 287.9 | 14.5 | 94C-D | Violet-Blue |
| 1728-31 | 63.8 | 2.8 | -17.8 | 279.0 | 18.0 | 97A-B | Violet-Blue |
| 1728-32 | 43.0 | 7.7 | -28.8 | 285.0 | 29.8 | 95C | Violet-Blue |
| 1728-33 | 59.5 | 4.1 | -18.4 | 282.5 | 18.8 | 96C-D | Violet-Blue |
| 1728-35 | 71.7 | -0.1 | -11.3 | 269.5 | 11.3 | 97A | Violet-Blue |
| 1728-36 | 63.8 | 1.3 | -19.5 | 273.9 | 19.6 | 97A | Violet-Blue |
| 1728-37 | 64.7 | 7.5 | -15.4 | 295.8 | 17.1 | 97B-C | Violet Blue |
| 1728-38 | 65.9 | 3.0 | -15.4 | 280.8 | 15.7 | 97A-B | Violet-Blue |
| 1728-43 | 72.7 | 4.3 | -9.6 | 294.1 | 10.5 | 91B | Violet-Blue |
| 2027-01 | 69.9 | 1.5 | -14.1 | 276.1 | 14.2 | 97A/100C | Violet-Blue/ Blue |
| 2027-09 | 70.9 | 3.5 | -14.8 | 283.2 | 15.2 | 96D | Violet-Blue |
| 2027-10 | 73.8 | 3.0 | -10.4 | 285.8 | 10.8 | NA | NA |
| 2027-11 | 66.7 | 4.2 | -17.0 | 283.7 | 17.5 | 96C | Violet-Blue |
| 2027-12 | 72.7 | 1.8 | -12.2 | 278.2 | 12.3 | NA | NA |

NA: Not analyzable or measurable
* Mean value (n = 23)

Example 2: Introduction of pB423 into
Chrysanthemum Variety "Sei Arabella" (Line No.
T34) (Coexpression of Clitoria A3'5'GT Gene
Under the Control of Chrysanthemum F3H
Promoter 1k and Agrobacterium Nos Terminator
and Campanula F3'5'H Gene Under the Control of
Chrysanthemum F3H Promoter 1k and Arabidopsis
HSP Terminator)

[1] Vector Assembly

Plasmid pB423 (pBCtA3'5'GT+CamF3'5'H) was created according to Example 1.

[2] Obtaining Transformants and Measuring Flower Color

A salmon-pink colored medium-sized decorative *chrysanthemum* variety "Sei Arabella" (Inochio Seikoen; Line No. T34) was transformed using pB423-transferred *Agrobacterium* EHA105 (provided by Dr. Elizabeth E. Hood), and 47 transformant lines were obtained. As a result of color measurement with a spectroscopic colorimeter (CD100, Yokogawa Electric Corp.) and an RHS color chart, alteration of flower color toward blue was confirmed in 34 lines (72%). Accumulation of delphinidin 3-(6"-malonyl)glucoside-3',5'-diglucoside (ternatin C5) and delphinidin 3,3',5'-triglucoside (preternatin C5) as the major anthocyanins was confirmed in 27 of the lines. The flower colors in these lines were modified to colors of the Blue group or Violet-Blue group in the RHS color chart. Blue chrysanthemums were obtained at a high proportion of 72% with "Sei Arabella", similar to "Taipei". The measured values for the transformants confirmed to have modification of flower color toward blue are shown below in Table 2.

TABLE 2

|  | CIEL*a*b* color system | | | | | RHS color chart | |
| --- | --- | --- | --- | --- | --- | --- | --- |
| Line No. | L | A | B | Hue angle (hue °) | Chroma (C) | Chart No. | Color group |
| Sei Arabella wild type | 77.7 | 15.0 | −1.4 | 354.6 | 15.1 | 73A-B | Red-Purple |
| Sei Arabella transformants | | | | | | | |
| 1916-01 | 65.3 | 2.3 | −14.3 | 279.1 | 14.5 | 97A | Violet-Blue |
| 1916-02 | 52.4 | 2.6 | −21.4 | 276.9 | 21.5 | 95C, 97A | Violet-Blue |
| 1916-03 | 62.2 | 15.1 | −13.5 | 318.3 | 20.3 | 84A | Violet |
| 1916-04 | 46.6 | 5.9 | −25.9 | 282.8 | 26.6 | 95C | Violet-Blue |
| 1916-05 | 55.0 | 5.1 | −18.3 | 285.4 | 19.0 | 92B | Violet-Blue |
| 1916-06 | 67.3 | 3.4 | −11.5 | 286.6 | 12.0 | 92B-C | Violet-Blue |
| 1916-10 | 45.4 | 32.3 | −22.9 | 324.7 | 39.6 | N81A-B | Purple-Violet |
| 1916-12 | 56.9 | 5.9 | −17.3 | 289.0 | 18.3 | 94B | Violet-Blue |
| 1916-15 | 57.8 | 1.9 | −16.7 | 276.6 | 16.8 | 97A-B | Violet-Blue |
| 1916-16 | 44.9 | 30.6 | −23.2 | 322.9 | 38.4 | N81B-C | Purple-Violet |
| 1916-17 | 57.6 | 3.0 | −22.9 | 277.5 | 23.1 | 96D | Violet-Blue |
| 1916-18 | 66.6 | 1.5 | −7.3 | 281.6 | 7.4 | 85B | Violet |
| 1916-19 | 60.7 | 4.2 | −19.6 | 282.1 | 20.0 | 95O | Violet-Blue |
| 1916-20 | 51.9 | 3.4 | −21.3 | 279.2 | 21.6 | 95C-D | Violet-Blue |
| 1916-21 | 72.2 | 3.0 | −7.5 | 291.7 | 8.1 | 91C | Violet-Blue |
| 1916-22 | 56.8 | 2.0 | −18.7 | 276.1 | 18.8 | 95C-D | Violet-Blue |
| 1916-23 | 52.7 | 4.4 | −23.8 | 280.6 | 24.3 | 100B-C | Blue |
| 1916-24 | 69.3 | 1.7 | −9.7 | 280.1 | 9.9 | 92C | Violet-Blue |
| 1916-26 | 59.9 | 1.5 | −15.8 | 275.5 | 15.9 | 96D | Violet-Blue |
| 1916-27 | 50.9 | 2.8 | −23.2 | 276.8 | 23.4 | 96D | Violet-Blue |
| 1988-02 | 78.3 | −2.6 | −0.2 | 274.0 | 2.6 | 95D | Violet-Blue |
| 1988-01 | 64.3 | 13.6 | −11.3 | 320.1 | 17.7 | 84A | Violet |
| 2072-02 | 72.2 | −0.8 | −7.6 | 263.9 | 7.7 | NA | NA |
| 2072-04 | 62.5 | −1.8 | −16.1 | 263.6 | 16.2 | NA | NA |
| 2072-05 | 75.1 | −1.2 | −8.8 | 442.3 | 8.9 | NA | NA |
| 2072-06 | 68.0 | −0.5 | −12.8 | 267.6 | 12.8 | NA | NA |
| 2072-10 | 65.3 | 13.8 | −6.6 | 334.6 | 15.3 | NA | NA |
| 2072-14 | 57.3 | 1.9 | −22.1 | 274.9 | 22.2 | NA | NA |
| 2072-17 | 61.7 | −0.3 | −16.0 | 268.9 | 16.0 | NA | NA |
| 2072-18 | 68.8 | 2.1 | −7.7 | 285.4 | 8.0 | NA | NA |
| 2072-25 | 66.0 | 0.1 | −12.2 | 270.6 | 12.2 | NA | NA |
| 2072-26 | 58.4 | 0.2 | −17.9 | 270.8 | 17.9 | NA | NA |
| 2072-29 | 71.2 | 5.5 | −6.2 | 311.2 | 8.3 | NA | NA |
| 2072-30 | 67.8 | 0.2 | −10.9 | 271.0 | 10.9 | NA | NA |

NA: Not analyzable or measurable

Example 3: Introduction of pB423 into Chrysanthemum Line "T37" (Coexpression of Clitoria A3'5'GT Gene Under the Control of Chrysanthemum F3H Promoter 1k and Agrobacterium Nos Terminator and Campanula F3'5'H Gene Under the Control of Chrysanthemum F3H Promoter 1k and Arabidopsis HSP Terminator)

[1] Vector Assembly

Plasmid pB423 (pBCtA3'5'GT+CamF3'5'H) was created according to Example 1.

[2] Obtaining Transformants and Measuring Flower Color

A pink-colored small-sized pompon chrysanthemum line "T37" (sampled breeding line provided by Inochio Seikoen) was transformed using pB423-transferred Agrobacterium EHA105 (provided by Dr. Elizabeth E. Hood), and 97 transformant lines were obtained. As a result of color measurement with a spectroscopic colorimeter (CD100, Yokogawa Electric Corp.) and an RHS color chart, alteration of flower color toward blue was confirmed in 58 lines (60%). Accumulation of delphinidin 3-(6''-malonyl)glucoside-3',5'-diglucoside (ternatin C5) and delphinidin 3,3',5'-triglucoside (preternatin C5) as the major anthocyanins was confirmed using 9 of the lines. Their flower colors were modified to the Violet-Blue group. Blue chrysanthemums were obtained at a high proportion of 60% with "T37", similar to "Taipei" and "Sei Arabella". The measured values for the transformants confirmed to have modification of flower color toward blue are shown below in Table 3.

TABLE 3

| | CIEL*a*b* color system | | | | | RHS color chart | |
|---|---|---|---|---|---|---|---|
| Line No. | L | A | B | Hue angle (hue °) | Chroma (C) | Chart No. | Color group |
| T37 wild type | 48.9 | 38.9 | −14.1 | 340.1 | 41.4 | N74B | Red-Purple |
| T37 transformants | | | | | | | |
| 1921-01 | 47.9 | 9.8 | −19.3 | 297.0 | 21.7 | 94B-C | Violet Blue |
| 1921-02 | 45.7 | 10.3 | −22.1 | 295.1 | 24.4 | 93C-D | Violet-Blue |
| 1921-03 | 50.8 | 8.5 | −22.5 | 290.8 | 24.1 | 96B | Violet-Blue |
| 1921-04 | 58.4 | 3.7 | −17.8 | 281.7 | 18.1 | 96C | Violet-Blue |
| 1921-05 | 44.8 | 6.1 | −22.9 | 285.0 | 23.7 | 96B-C | Violet Blue |
| 1921-06 | 55.4 | 5.4 | −16.4 | 288.4 | 17.3 | 93C-D | Violet-Blue |
| 1939-01 | 51.1 | 20.9 | −16.6 | 321.5 | 26.7 | N81B | Purple-Violet |
| 1939-02 | 50.0 | 5.6 | −21.3 | 284.8 | 22.0 | 96B | Violet-Blue |
| 1939-03 | 42.3 | 8.1 | −24.4 | 288.3 | 25.7 | 96B | Violet-Blue |
| 1939-04 | 50.7 | 6.8 | −23.2 | 286.2 | 24.2 | 96B | Violet-Blue |
| 1972-03 | 57.4 | 5.5 | −18.1 | 287.0 | 18.9 | 96C-D | Violet-Blue |
| 1972-05 | 86.7 | −0.1 | 2.0 | 93.5 | 2.0 | 91D | Violet-Blue |
| 1989-01 | 61.7 | 19.1 | −12.9 | 325.9 | 23.1 | 84A | Violet |
| 1989-02 | 64.1 | 4.9 | −13.1 | 290.4 | 14.0 | 92C | Violet-Blue |
| 1990-05 | 56.8 | 4.8 | −16.8 | 286.0 | 17.5 | 96D | Violet-Blue |
| 2013-03 | 56.3 | 6.2 | −18.9 | 288.1 | 19.9 | 96D | Violet-Blue |
| 2013-04 | 63.7 | 4.1 | −14.2 | 286.2 | 14.8 | 96D | Violet-Blue |
| 2013-06 | 69.4 | 1.5 | −12.1 | 276.9 | 12.1 | 97A | Violet-Blue |
| 2013-07 | 68.3 | 1.0 | −11.4 | 275.2 | 11.5 | 96C | Violet-Blue |
| 2013-08 | 65.1 | 0.1 | −12.1 | 270.3 | 12.1 | 96C | Violet-Blue |
| 2018-01 | 67.2 | 3.9 | −11.1 | 289.2 | 11.8 | 94D | Violet-Blue |
| 2018-02 | 70.6 | 5.5 | −9.8 | 299.4 | 11.2 | 91B | Violet-Blue |
| 2018-03 | 72.7 | 4.6 | −9.1 | 296.9 | 10.2 | 91C | Violet-Blue |
| 2018-04 | 69.6 | 6.5 | −9.9 | 303.1 | 11.8 | 85A-B | Violet |
| 2018-05 | 73.8 | 6.4 | −7.3 | 310.9 | 9.7 | 85B-C | Violet |
| 2018-06 | 57.5 | 2.2 | −17.4 | 277.1 | 17.5 | 96B | Violet-Blue |
| 2018-08 | 63.2 | 4.7 | −10.8 | 293.5 | 11.8 | 91B | Violet-Blue |
| 2018-09 | 71.3 | 2.3 | −10.1 | 282.8 | 10.4 | 93D | Violet-Blue |
| 2018-10 | 64.2 | 3.3 | −14.9 | 282.5 | 15.3 | 92B | Violet-Blue |
| 2018-11 | 64.5 | 3.4 | −15.6 | 282.3 | 16.0 | 96D | Violet-Blue |
| 2018-12 | 62.9 | 4.8 | −11.9 | 292.1 | 12.8 | 91A-B | Violet-Blue |
| 2018-13 | 72.9 | 7.4 | −3.3 | 335.8 | 8.1 | 84B-C | Violet |
| 2018-14 | 59.1 | 7.8 | −13.1 | 300.6 | 15.3 | 92B-C | Violet-Blue |
| 2018-15 | 67.6 | 3.6 | −8.7 | 292.8 | 9.4 | 92C | Violet-Blue |
| 2036-02 | 52.5 | 8.7 | −20.0 | 293.4 | 21.8 | NA | NA |
| 2036-05 | 64.4 | 5.3 | −4.1 | 322.8 | 6.7 | 92C | Violet-Blue |
| 2036-06 | 75.2 | 5.3 | −7.7 | 304.5 | 9.4 | 85C | Violet |
| 2036-11 | 60.2 | 4.2 | −17.7 | 283.4 | 18.2 | 97AB | Violet-Blue |
| 2036-14 | 50.1 | 8.6 | −20.5 | 292.7 | 22.2 | NA | NA |
| 2036-15 | 70.1 | 3.6 | −12.5 | 286.0 | 13.0 | 94D | Violet-Blue |
| 2036-19 | 61.3 | 5.1 | −16.5 | 287.1 | 17.3 | NA | NA |
| 2036-20 | 67.3 | 3.9 | −12.8 | 286.9 | 13.4 | 96D | Violet-Blue |
| 2036-24 | 66.1 | 3.3 | −14.3 | 283.0 | 14.7 | 96D | Violet-Blue |
| 2036-27 | 70.3 | 2.8 | −11.2 | 284.2 | 11.5 | 92CD | Violet-Blue |
| 2036-32 | 68.0 | 7.0 | −11.5 | 301.3 | 13.4 | N88C | Violet |
| 2036-33 | 63.8 | 4.8 | −15.5 | 287.2 | 16.2 | 93D | Violet-Blue |
| 2036-36 | 61.0 | 6.5 | −17.2 | 290.6 | 18.4 | 94C-D | Violet-Blue |
| 2047-02 | 65.3 | 7.9 | −11.1 | 305.5 | 13.6 | 85A | Violet |
| 2047-03 | 58.2 | 5.0 | −19.3 | 284.6 | 19.9 | 96C-D | Violet-Blue |
| 2047-04 | 62.8 | 3.6 | −14.7 | 283.8 | 15.1 | NA | NA |
| 2047-05 | 51.2 | 11.8 | −20.9 | 299.5 | 24.0 | 92A-90C | Violet-Blue |

TABLE 3-continued

| | CIEL*a*b* color system | | | | | RHS color chart | |
|---|---|---|---|---|---|---|---|
| Line No. | L | A | B | Hue angle (hue °) | Chroma (C) | Chart No. | Color group |
| 2047-07 | 54.0 | 13.2 | -15.9 | 309.7 | 20.7 | 90C-92A | Violet-Blue |
| 2047-08 | 63.9 | 5.9 | -13.6 | 293.3 | 14.8 | 94C-D | Violet-Blue |
| 2047-09 | 57.1 | 5.1 | -20.8 | 283.6 | 21.4 | 97A | Violet-Blue |
| 2047-10 | 54.3 | 7.4 | -22.5 | 288.1 | 23.7 | 96C-D | Violet-Blue |
| 2047-11 | 60.8 | 9.5 | -16.2 | 300.4 | 18.8 | 90D | Violet-Blue |
| 2047-12 | 59.0 | 5.8 | -15.8 | 290.2 | 16.8 | 94C | Violet-Blue |
| 2047-15 | 63.9 | 13.5 | -11.3 | 320.1 | 17.6 | 76A | Purple |

NA: Not analyzable or measurable

Example 4: Introduction of pB425 into Chrysanthemum Variety "Taipei" (Coexpression of Clitoria A3'5'GT Gene Under the Control of Chrysanthemum F3H Promoter 1k and Arabidopsis HSP Terminator and Campanula F3'5'H Gene Under the Control of Chrysanthemum F3H Promoter 1k and Agrobacterium Nos Terminator)

[1] Vector Assembly

Campanula F3'5'H-expressing binary vector pB315 (pB-Cam2) was constructed for linkage of multiple gene inhibition/expression cassettes, a Chrysanthemum F3'H inhibition cassette, and CtAGS, CtA3'5'GT and DFR expression cassettes. A binary vector DNA fragment obtained by digesting pBI121-FASS-CmF3H1k with SpeI and EcoICRI was linked with an approximately 1.7 kb DNA fragment obtained by digesting a KpnI digestion product of pCR ADHNF-Campanula F3'5'H (Japanese Patent No. 5697040) with XbaI after blunting the ends, to obtain pB315 (pBI121-FASS-CmF3Hpro1k:NtADH-5'UTR-Campanula F3'S'H:NOSter; pBCam2).

A DNA fragment obtained by digesting pBSII-ADH-CtA3'S'GT obtained in Reference Example 1 with NheI and EcoICRI was linked with a vector fragment obtained by digesting pMCE5-2 (FASS-CmF3Hp-AtHSPt) with NheI and EcoICRI, to obtain pMCE5-2 ADHNF-CtA3'5'GT. A CmF3Hp1k:ADHNF-CtA3'5'GT:AtHSPt cassette obtained by digesting pMCE5-2 ADHNF-CtA3'5'GT with FseI and PmeI was linked with a binary vector DNA fragment obtained by digesting pB315 with FseI and SwaI, to obtain pB425 (pBCam2+CtA3'5'GT).

[2] Obtaining Transformants and Measuring Flower Color

Plasmid pB425-transferred Agrobacterium (provided by Dr. Elizabeth E. Hood) was used for transformation of the pink medium-sized chrysanthemum variety "Taipei" (sampled genetic resource maintained by aseptic culture at the NARO Institute of Floricultural Science), and 42 transformant lines were obtained. As a result of color measurement with a spectroscopic colorimeter (CD100, Yokogawa Electric Corp.) and an RHS color chart, alteration of flower color toward blue was found in 23 lines (55%). Blue color with a hue angle of ≤290° was exhibited in 11 of the lines (26% of the total). In 12 lines (29% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. Thus, blue chrysanthemum can be created by expression of two genes, the Clitoria-derived A3'5'GT gene and the Campanula-derived F3'S'H gene. The measured values for the transformants confirmed to have modification of flower color toward blue are shown below in Table 4.

TABLE 4

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | -2.0 | 356.6 | 11.1 | 65B, N74C, 75B | Red-Purple/ Purple |
| Ohira transformants | | | | | | | |
| 1729-08 | 72.9 | 3.2 | -10.8 | 286.3 | 11.3 | 94B | Violet-Blue |
| 1729-09 | 76.7 | 3.2 | -6.1 | 297.3 | 6.9 | 85C | Violet |
| 1729-11 | 76.6 | 6.1 | -6.8 | 311.8 | 9.1 | 94D | Violet-Blue |
| 1729-12 | 65.2 | 4.7 | -19.7 | 283.5 | 20.3 | 97B | Violet-Blue |
| 1729-14 | 77.7 | 1.1 | -6.9 | 279.0 | 7.0 | 97B-C | Violet-Blue |
| 1729-17 | 79.2 | 1.0 | -3.4 | 285.9 | 3.5 | 94D | Violet-Blue |
| 1729-18 | 69.5 | 5.2 | -11.3 | 294.6 | 12.5 | 85B | Violet |
| 1729-19 | 75.9 | 2.9 | 1.4 | 361.4 | 3.2 | 92D | Violet-Blue |
| 1729-24 | 61.9 | 4.2 | -19.9 | 282.0 | 20.3 | 97A/96D | Violet-Blue |

TABLE 4-continued

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| 1729-25 | 76.9 | 0.6 | −3.1 | 280.3 | 3.2 | 85C-D | Violet |
| 1729-26 | 83.2 | 1.6 | 2.0 | 411.5 | 2.5 | 85D | Violet |
| 1729-27 | 66.0 | 4.1 | −17.2 | 283.5 | 17.6 | 96D | Violet-Blue |
| 1729-28 | 75.4 | 3.5 | −6.3 | 298.9 | 7.1 | 85C | Violet |
| 1729-29 | 77.6 | 8.1 | −3.9 | 334.1 | 9.0 | N80D | Purple-Violet |
| 1729-33 | 79.5 | 2.8 | −2.3 | 321.5 | 3.6 | NA | NA |
| 1729-37 | 71.9 | 2.6 | −4.3 | 301.0 | 5.0 | 85C | Violet |
| 1729-38 | 81.8 | 3.6 | −2.8 | 322.3 | 4.6 | NA | NA |
| 1729-39 | 69.1 | 0.8 | −9.3 | 275.2 | 9.3 | 95D | Violet-Blue |
| 1729-40 | 72.0 | −0.2 | −9.3 | 269.1 | 9.3 | 97A-B | Violet-Blue |
| 1729-41 | 65.7 | 2.7 | −14.7 | 280.4 | 15.0 | 96C-D | Violet-Blue |
| 1729-44 | 68.6 | 5.5 | −7.8 | 305.1 | 9.5 | 85A-B | Violet |
| 1729-45 | 66.9 | 4.6 | −13.8 | 288.4 | 14.5 | 92A-B | Violet-Blue |
| 1729-46 | 72.7 | 6.3 | −8.3 | 306.9 | 10.4 | 85A | Violet |

\* Mean value (n = 23)
NA: Not analyzable or measurable

Example 5: Introduction of pB433 into *Chrysanthemum* Variety "Taihei" (Coexpression of *Clitoria* A3'5'GT Gene Under the Control of *Chrysanthemum* F3H Promoter 1k and *Agrobacterium* Nos Terminator and *Campanula* F3'5'H Gene and Dutch Iris DFR Gene Under the Control of *Chrysanthemum* F3H Promoter 1k and *Arabidopsis* HSP Terminator)

[1] Vector Assembly

A DNA fragment amplified by PCR using plasmid pSPB909 containing the DFR gene derived from Dutch iris (*Iris hollandica*) perianth lobe (Plant Cell Physiol 48 (2007) 1589, AB332098) as template, and IrisDFR_ADH_ORF_Fd (5'-CAAGAAAAATAA<u>ATGATGAGCCCCGTTGTC</u>-3', underline indicates sequence annealing with IhDFR; SEQ ID NO: 12) and IrisDFR_NdeI Rv (5'-CATATGTACCTCCCGTTCGCTTC-3'; SEQ ID NO: 13) as primers, and a DNA fragment amplified by PCR using pBI221 ADH-221 as template and XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and IrisDFR_ORF_ADH_Rv (5'-GGGGCTCATCAT<u>TTATTTTTCTTGATTTCCTTCAC</u>-3';

underline indicates sequence annealing with NtADH-5'UTR 94 bp; SEQ ID NO: 15) as primers, were combined and used as template, with XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and IrisDFR_NdeI Rv (5'-CATATGTACCTCCCGTTCGCTTC-3'; SEQ ID NO: 13) as primers, for PCR to amplify a DNA fragment comprising tobacco ADH-5'UTR 94 bp directly linked to the start codon of the Dutch iris DFR gene, and the fragment was cloned in pCR-bluntII-TOPO to obtain pCR-ADHNF-IhDFR-5'. A DNA fragment obtained by digesting this plasmid with SalI and EcoRV and a plasmid DNA fragment obtained by digesting pSPB909 with SalI and EcoRV were linked to obtain pUC E12-35Sp:ADHNF-IrisDFR:D8t. A DNA fragment obtained by blunting the ends of the XhoI digestion product of this plasmid and then digesting with NheI, and a plasmid DNA fragment obtained by digesting pMCE5-2 with NheI and EcoICRI, were linked to obtain pMCE5-2 ADHNF-IhDFR. An expression cassette obtained by digesting pMCE5-2-ADHNF-IhDFR with AscI and PmeI was linked with a pB423 binary vector DNA fragment obtained by digesting with AscI and SwaI, to obtain pB433 (pBCtA3'5'GT+CamF3'5'H+IhDFR).

[2] Obtaining Transformants and Measuring Flower Color

Plasmid pB433-transferred *Agrobacterium* EHA105 (provided by Dr. Elizabeth E. Hood) was used for transformation of the pink medium-sized *chrysanthemum* variety "Taipei" (sampled genetic resource maintained by aseptic culture at the NARO Institute of Floricultural Science), and 55 transformant lines were obtained. As a result of color measurement with a spectroscopic colorimeter (CD100, Yokogawa Electric Corp.) and an RHS color chart, of the 39 lines (71%) in which alteration of flower color toward blue was found, 31 lines (56% of the total) exhibited blue color with a hue angle of ≤290°. In 33 lines (60% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. By using *Arabidopsis* HSP terminator as the terminator for the *Campanula*-derived F3'5'H gene, blue *chrysanthemum* was created at a higher proportion than when using *Agrobacterium* nos terminator (Examples 4, 12-18). The measured values for the transformants confirmed to have modification of flower color toward blue are shown below in Table 5.

TABLE 5

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/Purple |
| | | | | Ohira transformants | | | |
| 1737-01 | 53.2 | 6.8 | −23.9 | 285.9 | 24.8 | 96A-B | Violet-Blue |
| 1737-03 | 63.6 | 5.8 | −18.6 | 287.4 | 19.5 | 94B-C | Violet-Blue |
| 1737-04 | 57.4 | 3.9 | −19.9 | 281.1 | 20.3 | 96B-C | Violet-Blue |
| 1737-05 | 62.1 | 5.0 | −20.6 | 283.6 | 21.2 | 96B-C | Violet-Blue |
| 1737-06 | 80.2 | 3.9 | −5.1 | 307.4 | 6.4 | 85B-C | Violet |
| 1737-07 | 53.6 | 7.4 | −27.4 | 285.0 | 28.3 | 96B-C | Violet-Blue |
| 1737-08 | 49.7 | 8.4 | −28.7 | 286.4 | 29.9 | 96B-C | Violet-Blue |
| 1737-10 | 64.8 | 10.4 | −15.1 | 304.4 | 18.3 | 90C | Violet-Blue |
| 1737-11 | 63.7 | 4.6 | −17.8 | 284.6 | 18.4 | 96C-D | Violet-Blue |
| 1737-12 | 58.8 | 3.9 | −19.4 | 281.3 | 19.8 | 96B | Violet-Blue |
| 1737-13 | 62.7 | 5.8 | −18.0 | 287.7 | 18.9 | NA | NA |
| 1737-17 | 70.4 | 3.3 | −14.8 | 282.5 | 15.2 | 96C-D | Violet-Blue |
| 1737-18 | 72.3 | 4.0 | −11.2 | 289.6 | 11.9 | 92A-B | Violet-Blue |
| 1737-19 | 53.2 | 7.9 | −30.3 | 284.7 | 31.3 | 96B | Violet-Blue |
| 1737-24 | 62.5 | 3.3 | −19.7 | 279.5 | 20.0 | 95C | Violet-Blue |
| 1737-25 | 66.5 | 3.3 | −17.2 | 280.9 | 17.5 | 96C-D | Violet-Blue |
| 1737-26 | 57.4 | 3.2 | −20.0 | 279.1 | 20.3 | 95C | Violet-Blue |
| 1737-28 | 61.2 | 4.1 | −22.1 | 280.6 | 22.4 | 95C | Violet-Blue |
| 1737-29 | 55.7 | 7.5 | −22.6 | 288.3 | 23.8 | 96A-B | Violet-Blue |
| 1737-30 | 65.5 | 1.3 | −17.4 | 274.3 | 17.4 | 97A-B | Violet-Blue |
| 1737-36 | 59.4 | 6.0 | −22.5 | 284.9 | 23.2 | 96B | Violet-Blue |
| 1737-38 | 61.3 | 8.1 | −23.0 | 289.3 | 24.3 | 94B | Violet-Blue |
| 1737-41 | 61.0 | 5.5 | −20.8 | 284.7 | 21.5 | 96B | Violet-Blue |
| 1737-42 | 61.7 | 4.8 | −18.3 | 284.6 | 18.9 | 94B | Violet-Blue |
| 1737-44 | 63.6 | 9.0 | −19.1 | 295.2 | 21.1 | 93C | Violet-Blue |
| 1737-45 | 66.5 | 1.2 | −10.9 | 276.4 | 10.9 | 97A-B | Violet-Blue |
| 1737-47 | 59.9 | 4.5 | −20.0 | 282.6 | 20.5 | 96D | Violet-Blue |
| 1737-48 | 59.6 | 6.8 | −20.1 | 288.7 | 21.2 | 96B-C | Violet-Blue |
| 1737-50 | 79.5 | 3.4 | −4.5 | 307.3 | 5.6 | 85C-D | Violet |
| 1737-51 | 59.9 | 5.3 | −6.8 | 308.1 | 8.6 | 96D | Violet-Blue |
| 1737-53 | 36.9 | 11.1 | −36.0 | 287.1 | 37.7 | 95B-C | Violet-Blue |
| 1737-54 | 78.5 | 3.1 | −5.0 | 302.3 | 5.9 | N82D | Violet |
| 1737-55 | 72.1 | 3.9 | −5.2 | 306.7 | 6.5 | N88C | Violet |
| 1737-56 | 57.2 | 5.6 | −23.3 | 283.4 | 24.0 | 95B-C | Violet-Blue |
| 1737-57 | 81.8 | 1.1 | −3.8 | 285.9 | 3.9 | 91CD | Violet-Blue |
| 1737-58 | 58.9 | 4.8 | −20.0 | 283.6 | 20.5 | 95C | Violet-Blue |
| 1737-59 | 50.2 | 8.3 | −28.1 | 286.5 | 29.3 | 96B | Violet-Blue |
| 1737-61 | 71.1 | 6.3 | −13.6 | 295.0 | 15.0 | N88C | Violet |
| 1737-62 | 53.7 | 4.4 | −22.2 | 281.3 | 22.6 | 95C | Violet-Blue |

* Mean value (n = 23)
NA: Not analyzable or measurable

Example 6: Introduction of pB434 into Chrysanthemum Variety "Taipei" (Coexpression of Clitoria A3'5'GT Gene Under the Control of Chrysanthemum F3H Promoter 1k and Agrobacterium Nos Terminator and Campanula F3'5'H Gene and Delphinium DFR Gene Under the Control of Chrysanthemum F3H Promoter 1k and Arabidopsis HSP Terminator)

[1] Vector Assembly

A DNA fragment amplified by PCR using plasmid pDbDFR4-8 (GenBank accession no. AB221083) containing a DFR gene derived from the sepal of Delphinium (Delphinium×belladonna, "Volkerfrieden") as template and DbDFR_ADH_ORF_Fd (5'-CAAGAAAAATAA<u>ATGACTGTAGAAACTGTTTGTG</u>-3';

underline indicates sequence annealing with DbDFR; SEQ ID NO: 16) and DbDFR_NcoI_Rv (5'-CCATGGTGTACT-TATAGTTGAATCC-3'; SEQ ID NO: 17) as primers, and a DNA fragment amplified by PCR using pBI221 ADH-221 as template and XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and DbDFR_ORF_ADH_Rv (5'-TTCTACAGTCAT<u>TTATTTTTCTTGATTTCCTTCAC</u>-3';

underline indicates sequence annealing with NtADH-5'UTR 94 bp; SEQ ID NO: 18) as primers, were combined and used as template for PCR using XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and DbDFR_NcoI_Rv (5'-CCATGGTGTACTTATAGTTGAATCC-3'; underline indicates sequence annealing with NtADH-5'UTR 94 bp; SEQ ID NO: 17) as primers and PrimeStar (Takara Bio, Inc.) as DNA polymerase, to obtain a DNA fragment comprising tobacco ADH-5'UTR 94 bp directly linked to the start codon of the *Delphinium* DFR gene. After conducting reaction to add dA to the blunt ended amplification product, it was used for TA cloning in pCR2.1 (Invitrogen) to obtain pCR-ADHNF-DbDFR-5'. A fragment obtained by digesting this plasmid with SmaI and NcoI was linked with a plasmid DNA fragment obtained by digesting pDbDFR4-8 with SmaI and NcoI, to obtain pBS-ADHNF-DbDFR. A DNA fragment obtained by blunting the ends of the XhoI digestion product of this plasmid and then digesting with SpeI, and a plasmid DNA fragment obtained by digesting pMCE5-2 with NheI and EcoICRI, were linked to obtain pMCE5-2 ADHNF-DbDFR. An expression cassette obtained by digesting pMCE5-2 ADHNF-DbDFR with AscI and PmeI was linked with a pB423 binary vector DNA fragment obtained by digesting with AscI and SwaI, to obtain pB434 (pBCtA3'5'GT+CamF3'5'H+DbDFR).

[2] Obtaining Transformants and Measuring Flower Color

Plasmid pB434-transferred *Agrobacterium* EHA105 (provided by Dr. Elizabeth E. Hood) was used for transformation of the pink medium-sized *chrysanthemum* variety "Taipei" (sampled genetic resource maintained by aseptic culture at the NARO Institute of Floricultural Science), and 12 transformant lines were obtained. As a result of color measurement with a spectroscopic colorimeter (CD100, Yokogawa Electric Corp.) and an RHS color chart, of the 8 lines (67%) in which alteration of flower color toward blue was found, 8 lines (67% of the total) exhibited blue color with a hue angle of ≤290°. Seven lines (58% of the total) exhibited flower color in the Violet-Blue group of the RHS color chart. In the lines with the blue flower trait, accumulation of the major anthocyanins delphinidin 3-(6''-malonyl)glucoside-3',5'-diglucoside (ternatin C5) and delphinidin 3,3',5'-triglucoside (preternatin C5) was confirmed. By using *Arabidopsis* HSP terminator as the terminator for the *Campanula*-derived F3'5'H gene, blue *chrysanthemum* was created at a higher proportion than when using *Agrobacterium* nos terminator (Examples 4, 12-18). The measured values for the transformants confirmed to have modification of flower color toward blue are shown below in Table 6.

Example 7: Introduction of pB435 into *Chrysanthemum* Variety "Taihei" (Coexpression of *Clitoria* A3'5'GT Gene Under the Control of *Chrysanthemum* F3H Promoter 1k and *Agrobacterium* Nos Terminator and *Campanula* F3'5'H Gene and *Clitoria* DFR Gene Under the Control of *Chrysanthemum* F3H Promoter 1k and *Arabidopsis* HSP Terminator)

[1] Vector Assembly

A DNA fragment amplified by PCR using plasmid pBSCtDFR20 (GenBank accession no. AB185901) containing a DFR gene derived from petals of *Clitoria* (*Clitoria ternatea* "Double Blue") as template, and CtDFR_ADH_ORF_Fd (5'-CAAGAAAAATAAATGGATTCAGCAGCTGAAGTG-3';

underline indicates sequence annealing with CtDFR; SEQ ID NO: 19) and CtDFR_SphI_Rv (5'-GCATGCTCTCATTATGTCAAG-3'; SEQ ID NO: 20) as primers, and a DNA fragment amplified by PCR using pBI221 ADH-221 as template and XbaI-ADH-Fd (5'-ACGCGTTCTAGAGTCTATTTAACTCAGTATTC-3';

underline indicates sequence annealing with NtADH-5'UTR 94 bp; SEQ ID NO: 14) and CtDFR_ORF_ADH_Rv (5'-TGCTGAATCCATTTATTTTTCTTGATTTCCTTCAC-3';

underline indicates sequence annealing with NtADH-5'UTR 94 bp; SEQ ID NO: 21) as primers, were combined and used as template for PCR using XbaI-ADH-Fd (5'-ACGCGTTCTAGAGTCTATTTAACTCAGTATTC-3';

underline indicates sequence annealing with NtADH-5'UTR 94 bp; SEQ ID NO: 14) and CtDFR_SphI_Rv (5'-GCATGCTCTCATTATGTCAAG-3'; SEQ ID NO: 20) as primers, and PrimeStar (Takara Bio, Inc.) as DNA polymerase, to obtain a DNA fragment comprising tobacco ADH-5'UTR 94 bp directly linked to the start codon of

TABLE 6

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/Purple |
| Ohira transformants | | | | | | | |
| 1744-02 | 62.8 | 2.3 | −14.7 | 278.7 | 14.9 | NA | NA |
| 1744-03 | 62.7 | 2.6 | −12.9 | 281.4 | 13.1 | 96D | Violet-Blue |
| 1744-07 | 65.9 | 0.2 | −15.4 | 270.8 | 15.4 | 97A-B | Violet-Blue |
| 1744-08 | 56.6 | 5.9 | −25.7 | 282.9 | 26.4 | 96B | Violet-Blue |
| 1744-09 | 55.3 | 7.8 | −22.4 | 289.2 | 23.7 | 94B | Violet-Blue |
| 1744-14 | 66.1 | 3.4 | −14.9 | 282.7 | 15.3 | 92A-B | Violet-Blue |
| 1744-19 | 62.9 | 1.9 | −16.8 | 276.3 | 16.9 | 97A | Violet-Blue |
| 1753-03 | 65.1 | 2.7 | −18.4 | 278.3 | 18.6 | 97A | Violet-Blue |

* Mean value (n = 23)
NA: Not analyzable or measurable

Clitoria DFR gene. After conducting reaction to add dA to the blunt ended amplification product, it was used for TA cloning in pCR2.1 (Invitrogen) to obtain pCR-ADHNF-CtDFR-5'. A fragment obtained by digesting this plasmid with XbaI and SphI was linked with a plasmid DNA fragment obtained by digesting pBSCtDFR20 with XbaI and SphI, to obtain pBS-ADHNF-CtDFR. A DNA fragment (090616-2) obtained by blunting the ends of the XhoI digestion product of this plasmid and then digesting with XbaI, and a plasmid DNA fragment obtained by digesting pMCE5-2 with NheI and EcoICRI, were linked to obtain pMCE5-2 ADHNF-CtDFR. An expression cassette obtained by digesting pMCE5-2 ADHNF-CtDFR with AscI and PmeI was linked with a pB423 binary vector DNA fragment obtained by digesting with AscI and SwaI, to obtain pB435 (pBCtA3'5'GT+CamF3'5'H+CtDFR).

[2] Obtaining Transformants and Measuring Flower Color

Plasmid pB435-transferred *Agrobacterium* EHA105 (provided by Dr. Elizabeth E. Hood) was used for transformation of the pink medium-sized *chrysanthemum* variety "Taihei" (sampled genetic resource maintained by aseptic culture at the NARO Institute of Floricultural Science), and 34 transformant lines were obtained. As a result of color measurement with a spectroscopic colorimeter (CD100, Yokogawa Electric Corp.) and an RHS color chart, alteration of flower color toward blue was found in 28 lines (82%). Blue with a hue angle of ≤290° was exhibited by 23 lines (68% of the total), and 22 lines (65% of the total) exhibited flower color in the Blue group or Violet-Blue group by measurement with the RHS color chart. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. By using *Arabidopsis* HSP terminator as the terminator for the *Campanula*-derived F3'5'H gene, blue *chrysanthemum* was created at a higher proportion than when using *Agrobacterium* nos terminator (Examples 4, 12-18). The measured values for the transformants confirmed to have modification of flower color toward blue are shown below in Table 7.

TABLE 7

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/Purple |
| Ohira transformants | | | | | | | |
| 1745-01 | 61.7 | 1.4 | −18.9 | 274.2 | 18.9 | 95B-C | Violet-Blue |
| 1745-02 | 67.1 | 2.0 | −15.3 | 277.4 | 15.5 | 97A-B | Violet-Blue |
| 1745-03 | 49.5 | 7.1 | −29.6 | 283.6 | 30.4 | 99B-C | Blue |
| 1745-04 | 52.1 | 7.8 | −28.7 | 285.2 | 29.8 | 96B-C | Violet-Blue |
| 1745-06 | 52.0 | 5.2 | −25.1 | 281.7 | 25.6 | 95C | Violet-Blue |
| 1745-07 | 58.3 | 4.9 | −22.3 | 282.5 | 22.8 | 96B-C | Violet-Blue |
| 1745-09 | 63.6 | 7.1 | −16.9 | 292.7 | 18.4 | N88B | Violet |
| 1745-10 | 57.3 | 6.8 | −26.9 | 284.1 | 27.8 | 95C | Violet-Blue |
| 1745-11 | 61.0 | 4.7 | −22.6 | 281.9 | 23.1 | 95C | Violet-Blue |
| 1745-12 | 48.4 | 20.0 | −22.1 | 312.2 | 29.8 | N87A-B | Violet |
| 1745-13 | 67.7 | 8.7 | −14.1 | 301.7 | 16.6 | 90C-D | Violet-Blue |
| 1745-14 | 48.3 | 7.1 | −27.2 | 284.6 | 28.1 | 96C | Violet-Blue |
| 1745-15 | 52.4 | 7.9 | −27.2 | 286.1 | 28.3 | 96A-B | Violet-Blue |
| 1745-16 | 64.7 | 3.1 | −17.5 | 279.9 | 17.8 | 96B-C | Violet-Blue |
| 1745-19 | 65.5 | 4.8 | −16.3 | 286.4 | 17.0 | 92B | Violet-Blue |
| 1745-20 | 59.2 | 4.8 | −21.5 | 282.5 | 22.1 | 96B-C | Violet-Blue |
| 1745-22 | NA | NA | NA | NA | NA | 85A-B | Violet |
| 1745-23 | 59.0 | 6.4 | −20.3 | 287.5 | 21.3 | 92A | Violet-Blue |
| 1745-28 | 65.5 | 3.0 | −9.6 | 287.3 | 10.1 | 85B | Violet |
| 1745-29 | 60.4 | 3.9 | −20.1 | 281.0 | 20.5 | 95C | Violet-Blue |
| 1754-01 | 59.6 | 4.7 | −19.8 | 283.5 | 20.4 | 96B-C | Violet-Blue |
| 1754-02 | 66.8 | 6.5 | −11.0 | 300.7 | 12.8 | N88C | Violet |
| 1754-03 | 58.9 | 3.6 | −19.2 | 280.6 | 19.6 | 96C-D | Violet-Blue |
| 1754-05 | 57.7 | 3.7 | −19.3 | 280.8 | 19.7 | 96C | Violet-Blue |
| 1754-06 | 64.8 | 1.8 | −14.9 | 277.0 | 15.0 | 96C | Violet-Blue |
| 1754-09 | 51.0 | 5.0 | −21.2 | 283.2 | 21.8 | 96B | Violet-Blue |
| 1754-10 | 71.3 | 2.1 | −10.5 | 281.1 | 10.7 | NA | NA |
| 1754-11 | 55.4 | 3.5 | −19.7 | 280.1 | 20.0 | 96C-D | Violet-Blue |

* Mean value (n = 23)
NA: Not analyzable or measurable

Example 8: Introduction of pB428 into *Chrysanthemum* Variety "Sei Shawl" (Sampled Variety Provided by Inochio Seikoen; Line No. S39) (Inhibition of *Chrysanthemum* Endogenous F3'H Gene Under the Control of *Chrysanthemum* F3H Promoter 1k and *Agrobacterium* Nos Terminator, and Coexpression of *Campanula* F3'5'H Gene and *Clitoria* A3'5'GT Gene Under the Control of *Chrysanthemum* F3H Promoter 1k and *Arabidopsis* HSP Terminator)

[1] Vector Assembly

*Chrysanthemum* F3'H ORF amplified by PCR using cDNA derived from *chrysanthemum* "Arietta" ray florets as template, CmF3'H_full_ORF_F (5'-ATGAACATTT-TACCTTTCGTATTTTATG-3'; SEQ ID NO: 22) and CmF3'H_full_ORF_R (5'-TTAAATACTTT- CATATACGTGGG-3'; SEQ ID NO: 23) as primers and LA Taq as DNA polymerase, was used for TA cloning in pCR2.1 to obtain pCR2.1-CmF3'H-ORF 1. A DNA fragment (SEQ ID NO: 38) serving as an RNAi trigger, amplified by PCR using the aforementioned plasmid as template and CmF3'H_3'-Fd for dsRNA (5'-CACCCCGAACTCAT-TCGTCATCCAC-3'; SEQ ID NO: 24) and CmF3'H 3'-Rv for dsRNA (5'-TCAATCCATACGCTTCTTCCATG-3'; SEQ ID NO: 25) as primers, was linked with pENTR-D/TOPO (Invitrogen) to obtain pENTR-CmF3'H-C. LR reaction was performed with pENTR-CmF3'H-C and pANDA35K to obtain pANDA- CmF3'H-C IR. An approximately 2.5 kb DNA fragment obtained by digesting this plasmid with XbaI and EcoICRI was linked with a binary vector DNA fragment obtained by digesting pB1121-FASS-CmF3H1k with SpeI and EcoICRI, to obtain pB319 (pBF3'H-Ci).

A plasmid DNA fragment obtained by digesting pMCE5-2 with NheI and EcoICRI was linked with an approximately 1.7 kb DNA fragment obtained by blunting the ends of a KpnI digestion product of pCR ADHNF-Campanula F3'S'H (Japanese Patent No. 5697040), and then digesting with XbaI, to obtain pMCE5-2 ADHNF-CamF3'S'H. An expression cassette obtained by digesting this plasmid with FseI and PmeI was linked with a binary vector fragment of pB319 obtained by digestion with FseI and SwaI, to obtain pB332 (pBF3'H-Ci+CamF3'5'H).

A binary vector DNA fragment obtained by digesting pB332 (pBF3'H-Ci+CamF3'5'H) with FseI and SwaI was linked with a CmF3Hp1k:ADHNF-CtA3'5'GT:AtHSPt cassette obtained by digesting pMCE5-2 ADHNF-CtA3'5'GT with FseI and PmeI, to obtain pB428 (pBF3'H-Ci+CamF3'5'H+CtA3'5'GT).

Figure 5:
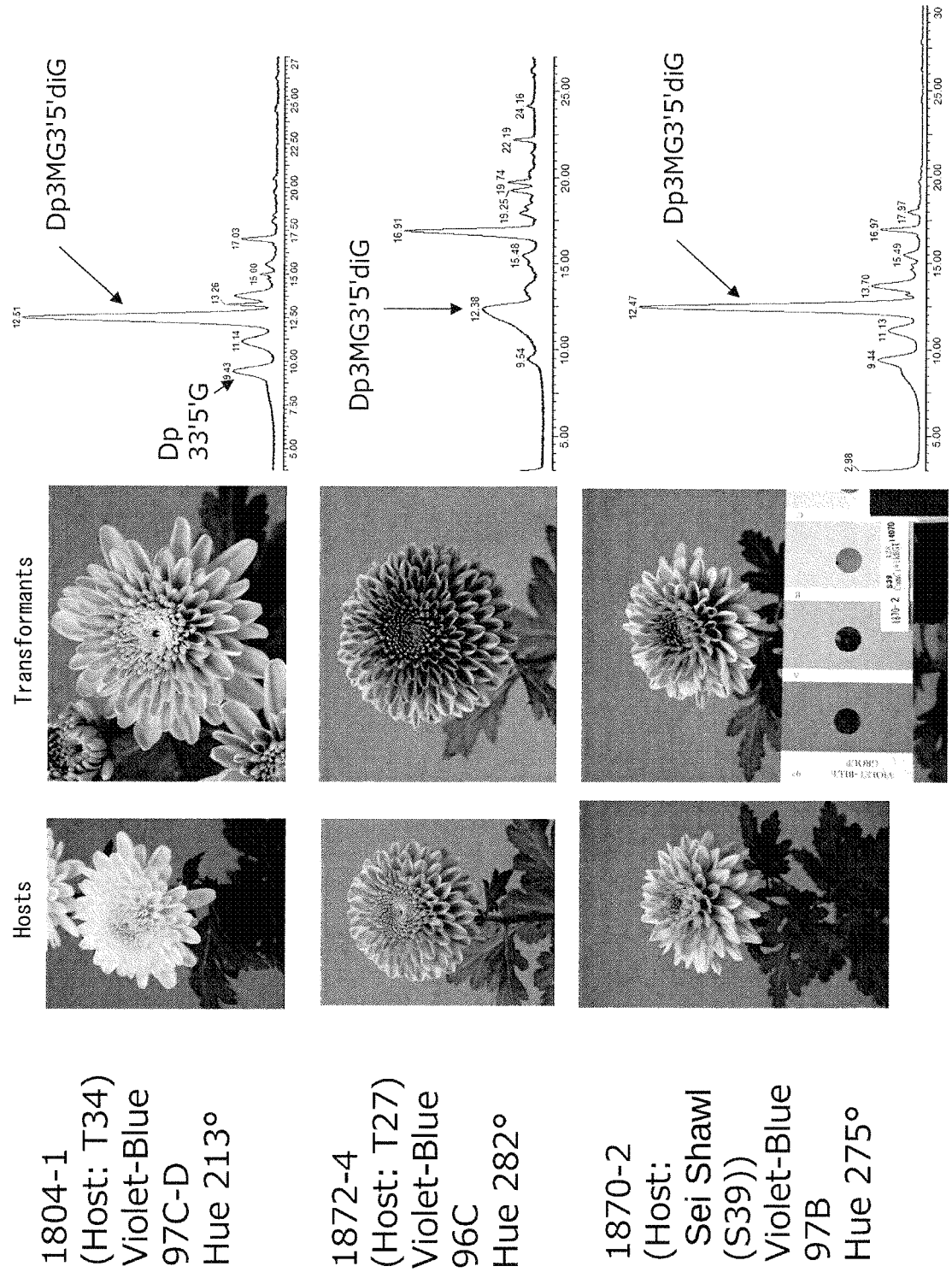
FIG. 5 shows photographs of flower color blueing of *chrysanthemum* into which CamF3'5'H and CtA3'5'GT were transformed, and HPLC analysis results for the major anthocyanins in the blue *chrysanthemum* petals.

The pink-colored large-sized decorative chrysanthemum variety "Sei Shawl" (variety provided by Inochio Seikoen; Line No. S39) was transformed using pB428-transferred Agrobacterium EHA105 (provided by Dr. Elizabeth E. Hood), and 10 transformant lines were obtained. As a result of color measurement with a spectroscopic colorimeter (CD100, Yokogawa Electric Corp.) and an RHS color chart, alteration of flower color toward blue was confirmed in 6 lines (60%), while in 3 lines (30% of the total), accumulation of delphinidin 3-(6"-malonyl)glucoside-3',5'-diglucoside (ternatin C5) and delphinidin 3,3',5'-triglucoside (preternatin C5) was confirmed, and the flower color was modified to the Blue group or Violet-Blue group (FIG. 5). By using Arabidopsis HSP terminator as the terminator for the Campanula-derived F3'5'H gene, blue chrysanthemum was created at a higher proportion than when using Agrobacterium nos terminator (Examples 4, 12-18). The measured values for the transformants confirmed to have modification of flower color toward blue are shown below in Table 8.

TABLE 8

| | CIEL*a*b* color system | | | | RHS color chart | |
|---|---|---|---|---|---|---|
| | | | | Hue | | |
| Line No. | L | A | B | angle (hue °) | Chroma (C) | Chart No. | Color group |
| S39 wild type | 70.6 | 24.0 | -4.8 | 348.6 | 24.5 | 73B | Red-Purple |
| S39 transformants | | | | | | | |
| 1870-01 | 66.1 | 4.3 | -12.7 | 288.8 | 13.4 | 93C | Violet-Blue |
| 1870-02 | 75.7 | 0.7 | -9.5 | 274.5 | 9.5 | 100D | Blue |

TABLE 8-continued

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| 1891-01 | 66.3 | 6.6 | -12.3 | 298.1 | 14.0 | 85B | Violet |
| 1891-02 | 58.8 | 4.8 | -19.1 | 284.0 | 19.7 | 96D | Violet-Blue |
| 1891-03 | 69.1 | 10.6 | -6.7 | 327.7 | 12.6 | N82C | Purple-Violet |
| 1891-04 | 66.1 | 14.6 | -10.5 | 324.1 | 18.0 | N81C | Purple-Violet |

Example 9: Introduction of pB428 into Chrysanthemum Line "T27" (Inhibition of Chrysanthemum Endogenous F3'H Gene Under the Control of Chrysanthemum F3H Promoter 1k and Agrobacterium Nos Terminator, and Coexpression of Campanula F3'5'H Gene and Clitoria A3'5'GT Gene Under the Control of Chrysanthemum F3H Promoter 1k and Arabidopsis HSP Terminator)

[1] Vector Assembly
Plasmid pB428 (pBF3'H-Ci+CamF3'5'H+CtA3'5'GT) was constructed according to Example 8.

[2] Obtaining Transformants and Measuring Flower Color
A pink-colored small-sized pompon chrysanthemum line "T27" (sampled breeding line provided by Inochio Seikoen) was transformed using pB428-transferred Agrobacterium EHA105 (provided by Dr. Elizabeth E. Hood), and 10 transformant lines were obtained. As a result of color measurement with a spectroscopic colorimeter (CD100, Yokogawa Electric Corp.) and an RHS color chart, alteration of flower color toward blue was confirmed in 6 lines (60%). Accumulation of delphinidin 3-(6"-malonyl)glucoside-3',5'-diglucoside (ternatin C5) and delphinidin 3,3',5'-triglucoside (preternatin C5) as the major anthocyanins was confirmed in 4 of the lines (40% of the total) (FIG. 5). Their flower colors in these lines were modified to the Violet-Blue group. By using Arabidopsis HSP terminator as the terminator for the Campanula-derived F3'5'H gene, blue chrysanthemum was created at a higher proportion than when using Agrobacterium nos terminator (Examples 4, 12-18). The measured values for the transformants confirmed to have modification of flower color toward blue are shown below in Table 9.

TABLE 9

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| T27 wild type | 74.2 | 14.7 | -3.3 | 347.5 | 15.1 | N74C | Red-Purple |
| T27 transformants | | | | | | | |
| 1805-01 | 76.2 | 1.9 | -1.2 | 327.6 | 2.2 | 85D | Violet |
| 1805-02 | 80.5 | -2.0 | 6.0 | 108.9 | 6.3 | 85D | Violet |
| 1872-01 | 65.2 | 5.3 | -12.8 | 292.6 | 13.8 | 94D | Violet-Blue |
| 1872-03 | 69.8 | 2.7 | -10.6 | 284.4 | 10.9 | 94D | Violet-Blue |
| 1872-04 | 67.6 | 2.5 | -12.1 | 281.6 | 12.4 | 96C | Violet-Blue |
| 1872-05 | 56.2 | 5.9 | -22.0 | 284.9 | 22.8 | 96C | Violet-Blue |

Example 10: Introduction of pB428 into
Chrysanthemum Variety "Sei Arabella" (Line No.
T34) (Inhibition of Chrysanthemum Endogenous
F3'H Gene Under the Control of Chrysanthemum
F3H Promoter 1k and Agrobacterium Nos
Terminator, and Coexpression of Campanula F3'5'H
Gene and Clitoria A3'5'GT Gene Under the Control
of Chrysanthemum F3H Promoter 1k and
Arabidopsis HSP Terminator)

[1] Vector Assembly

Plasmid pB428 (pBF3'H-Ci+CamF3'5'H+CtA3'5'GT) was constructed according to Example 8.

[2] Obtaining Transformants and Measuring Flower Color

A salmon-pink colored medium-sized decorative *chrysanthemum* variety "Sei Arabella" (Inochio Seikoen; Line No. T34) was transformed using pB428-transferred *Agrobacterium* EHA105 (provided by Dr. Elizabeth E. Hood), and 3 transformant lines were obtained. As a result of color measurement with a spectroscopic colorimeter (CD100, Yokogawa Electric Corp.) and an RHS color chart, alteration of flower color toward blue was confirmed in 3 lines (100%). Accumulation of delphinidin 3-(6-malonyl)glucoside 3',5'-diglucoside (ternatin C5) and delphinidin 3,3',5'-triglucoside (preternatin C5) as the major anthocyanins was confirmed in 2 of the lines (67% of the total) (FIG. 5). Their flower colors in these lines were modified to the Violet-Blue group. By using *Arabidopsis* HSP terminator as the terminator for the *Campanula*-derived F3'5'H gene, blue *chrysanthemum* was created at a higher proportion than when using *Agrobacterium* nos terminator (Examples 4, 12-18). The measured values for the transformants confirmed to have modification of flower color toward blue are shown below in Table 10.

TABLE 10

| | CIEL*a*b* color system | | | | | RHS color chart | |
| --- | --- | --- | --- | --- | --- | --- | --- |
| | | | | Hue | | | |
| Line No. | L | A | B | angle (hue °) | Chroma (C) | Chart No. | Color group |
| Sei Arabella wild type | 84.3 | 0.4 | 8.0 | 87.4 | 8.0 | 49C | Red |
| Sei Arabella transformants | | | | | | | |
| 1804-01 | 70.9 | −2.7 | −4.4 | 238.4 | 5.2 | 97C | Violet-Blue |
| 1804-02 | 72.1 | 7.5 | −6.9 | 317.5 | 10.2 | N82D | Purple-Violet |
| 1804-03 | 53.5 | −2.8 | 2.3 | 140.7 | 3.7 | 97D | Violet-Blue |

Example 11: Introduction of pB428 into
Chrysanthemum Line "T57" (Inhibition of
Chrysanthemum Endogenous F3'H Gene Under the
Control of Chrysanthemum F3H Promoter 1k and
Agrobacterium Nos Terminator, and Coexpression
of Campanula F3'5'H Gene and Clitoria A3'5'GT
Gene Under the Control of Chrysanthemum F3H
Promoter 1k and Arabidopsis HSP Terminator)

[1] Vector Assembly

Plasmid pB428 (pBF3'H-Ci+CamF3'5'H+CtA3'5'GT) was constructed according to Example 8.

[2] Obtaining Transformants and Measuring Flower Color

The salmon-pink colored medium-sized decorative *chrysanthemum* line "T57" (sampled breeding line provided by Inochio Seikoen) was transformed using pB428-transferred *Agrobacterium* EHA105 (provided by Dr. Elizabeth E. Hood), and 1 transformant line was obtained. As a result of color measurement with a spectroscopic colorimeter (CD100, Yokogawa Electric Corp.) and an RHS color chart, alteration of flower color toward blue was confirmed, and accumulation of delphinidin 3-(6-malonyl)glucoside 3',5'-diglucoside (ternatin C5) and delphinidin 3,3',5'-triglucoside (preternatin C5), as the major anthocyanins, was confirmed. The flower color of this line was modified to the Violet-Blue group, and the measured values are shown in Table 11 below.

TABLE 11

| | CIEL*a*b* color system | | | | | RHS color chart | |
| --- | --- | --- | --- | --- | --- | --- | --- |
| | | | | Hue | | | |
| Line No. | L | A | B | angle (hue °) | Chroma (C) | Chart No. | Color group |
| T57 wild type | 61.5 | 31.6 | −13.3 | 337.1 | 34.2 | 74B-C | Red-Purple |
| T57 transformants | | | | | | | |
| 1890-01 | 56.5 | 7.3 | −22.5 | 288.0 | 23.6 | 94A | Violet-Blue |

Example 12: Introduction of pB436 into
Chrysanthemum Variety "Taihei" (Coexpression of
Campanula F3's'H Gene Under the Control of
Chrysanthemum F3H Promoter 1k and
Agrobacterium Nos Terminator, and the Clitoria
A3's'GT Gene and Dutch Iris DFR Gene Under the
Control of Chrysanthemum F3H Promoter 1k and
Arabidopsis HSP Terminator)

[1] Vector Assembly

An expression cassette obtained by digesting pMCE5-2 ADHNF-IhDFR obtained in Example 5 with AscI and PmeI was linked with a pB425 binary vector DNA fragment obtained by digestion with AscI and SwaI, to obtain pB436 (pBCam2+CtA3'5'GT+IhDFR).

[2] Obtaining Transformants and Measuring Flower Color

Plasmid pB436-transferred *Agrobacterium* EHA105 (provided by Dr. Elizabeth E. Hood) was used for transformation of the pink medium-sized *chrysanthemum* variety "Taihei" (sampled genetic resource maintained by aseptic culture at the NARO Institute of Floricultural Science), and 57 transformant lines were obtained. As a result of color measurement with a spectroscopic colorimeter (CD100, Yokogawa Electric Corp.) and an RHS color chart, alteration of flower color toward blue was found in 32 lines (56%). In 16 lines (28% of the total), blue color with a hue angle of ≤290° was exhibited, and in 14 lines (25% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 12.

TABLE 12

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| Ohira wild type * | 79.5 | 9.7 | −2.0 | 356.6 | 11.1 | 65B, N74C, 75B | Red-Purple/Purple |
| | | | | Ohira transformants | | | |
| 1733-01 | 81.0 | 7.1 | −0.8 | 353.9 | 7.1 | 84B | Violet |
| 1738-02 | 76.6 | 1.8 | −5.9 | 287.2 | 6.2 | 96D | Violet-Blue |
| 1738-03 | 74.3 | 6.0 | −9.2 | 303.3 | 11.0 | N82D | Purple-Violet |
| 1738-05 | 70.6 | 3.7 | −12.5 | 286.3 | 13.0 | 93D | Violet-Blue |
| 1738-06 | 77.5 | 4.1 | −6.3 | 302.8 | 7.5 | 85B | Violet |
| 1738-08 | 69.5 | 2.7 | −11.8 | 282.9 | 12.1 | 91C | Violet-Blue |
| 1738-09 | 68.1 | 2.9 | −15.4 | 280.7 | 15.7 | 96C-D | Violet-Blue |
| 1738-11 | 78.8 | 0.6 | −3.3 | 280.0 | 3.4 | 96D | Violet-Blue |
| 1738-12 | 69.1 | 4.9 | −12.0 | 292.1 | 12.9 | 91B | Violet-Blue |
| 1738-15 | 77.4 | 3.8 | −6.4 | 300.9 | 7.5 | 85A-B | Violet |
| 1738-16 | 70.5 | 5.8 | −11.6 | 296.4 | 13.0 | N88C-D | Violet |
| 1738-21 | 53.2 | 4.8 | −24.6 | 280.9 | 25.1 | 95C | Violet-Blue |
| 1738-23 | 81.3 | 2.1 | −2.6 | 309.6 | 3.4 | N88C-D | Violet |
| 1738-24 | 71.2 | 3.1 | −11.6 | 284.9 | 12.0 | 91B-C | Violet-Blue |
| 1738-25 | 77.0 | 2.8 | −7.9 | 289.3 | 8.4 | 85B | Violet |
| 1738-27 | 81.1 | 2.3 | −3.9 | 300.7 | 4.5 | 85D | Violet |
| 1738-28 | 60.9 | 3.3 | −20.7 | 279.0 | 20.9 | 97A | Violet-Blue |
| 1738-30 | 58.4 | 5.9 | −16.9 | 289.2 | 17.9 | 94B | Violet-Blue |
| 1738-31 | 77.6 | 1.9 | −5.5 | 288.8 | 5.8 | NA | NA |
| 1738-32 | 70.0 | 4.9 | −9.3 | 297.6 | 10.5 | N88C-D | Violet |
| 1738-33 | 70.8 | 6.1 | −11.3 | 298.5 | 12.9 | 85B | Violet |
| 1738-35 | 71.2 | 5.9 | −10.5 | 299.2 | 12.0 | 85B | Violet |
| 1738-38 | 68.4 | 2.0 | −8.9 | 282.8 | 9.1 | NA | NA |
| 1738-41 | 71.6 | 2.1 | −9.8 | 282.0 | 10.0 | 95D | Violet-Blue |
| 1738-52 | 74.8 | 4.1 | −7.7 | 298.0 | 8.7 | 85B | Violet |
| 1738-53 | 75.3 | 5.7 | −7.4 | 307.5 | 9.4 | 85B-C | Violet |
| 1738-54 | 77.3 | 4.4 | −5.2 | 310.1 | 6.8 | 85B | Violet |
| 1738-57 | 73.0 | 4.6 | −8.6 | 298.4 | 9.7 | 85B | Violet |
| 1738-58 | 67.8 | 1.5 | −12.5 | 277.0 | 12.6 | 95D | Violet-Blue |
| 1738-60 | 76.9 | 0.2 | −7.6 | 271.3 | 7.6 | 97C | Violet-Blue |
| 1738-62 | 65.9 | 1.5 | −13.2 | 276.6 | 13.3 | 96C-D | Violet-Blue |
| 1738-63 | 77.4 | 3.1 | −5.8 | 298.1 | 6.6 | 85B | Violet |

* Mean value (n = 23)
NA: Not analyzable or measurable

Example 13: Introduction of pB437 into *Chrysanthemum* Variety "Taipei" (Coexpression of *Campanula* F3'5'H Gene Under the Control of *Chrysanthemum* F3H Promoter 1k and *Agrobacterium* Nos Terminator, and *Clitoria* A3'5'GT Gene and *Delphinium* DFR Gene Under the Control of *Chrysanthemum* F3H Promoter 1k and *Arabidopsis* HSP Terminator)

[1] Vector Assembly

An expression cassette obtained by digesting pMCE5-2 ADHNF-DbDFR obtained in Example 6 with AscI and PmeI was linked with a pB425 binary vector DNA fragment obtained by digestion with AscI and SwaI, to obtain pB437 (pBCam2+CtA3'5'GT+DbDFR).

[2] Obtaining Transformants and Measuring Flower Color

Plasmid pB437-transferred *Agrobacterium* EHA105 (provided by Dr. Elizabeth E. Hood) was used for transformation of the pink medium-sized *chrysanthemum* variety "Taihei" (sampled genetic resource maintained by aseptic culture at the NARO Institute of Floricultural Science), and 38 transformant lines were obtained. As a result of color measurement with a spectroscopic colorimeter (CD100, Yokogawa Electric Corp.) and an RHS color chart, alteration of flower color toward blue was found in 21 lines (55%). In 9 lines (24% of the total), blue color with a hue angle of ≤290° was exhibited, and in 8 lines (21% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 13.

TABLE 13

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| Ohira wild type * | 79.5 | 9.7 | −2.0 | 356.6 | 11.1 | 65B, N74C, 75B | Red-Purple/Purple |
| Ohira transformants | | | | | | | |
| 1746-03 | 68.8 | 7.0 | −12.8 | 298.8 | 14.6 | N88C | Violet |
| 1746-08 | 76.4 | 1.3 | −4.9 | 284.7 | 5.1 | NA | NA |
| 1746-10 | 79.5 | 3.2 | −5.2 | 302.0 | 6.1 | 85C | Violet |
| 1746-11 | 70.6 | 4.0 | −9.0 | 294.0 | 9.9 | N82D | Purple-Violet |
| 1746-12 | 76.2 | −0.3 | −5.9 | 267.1 | 5.9 | 92C-D | Violet-Blue |
| 1746-13 | 76.0 | 1.7 | −6.4 | 285.0 | 6.7 | 92C-D | Violet-Blue |
| 1746-23 | 67.6 | 3.2 | −9.8 | 287.9 | 10.3 | 85B | Violet |
| 1746-25 | 76.7 | 2.8 | −4.7 | 300.7 | 5.5 | 85C | Violet |
| 1746-28 | 73.5 | 3.0 | −5.1 | 300.1 | 5.9 | 85A-B | Violet |
| 1746-30 | NA | NA | NA | NA | NA | N82D | Purple-Violet |
| 1746-31 | 71.2 | 3.8 | −10.5 | 289.8 | 11.1 | 92B | Violet-Blue |
| 1746-32 | 73.9 | 2.6 | −6.1 | 293.4 | 6.6 | 91B | Violet-Blue |
| 1746-34 | 72.1 | 3.1 | −10.6 | 286.5 | 11.1 | 91B | Violet-Blue |
| 1746-35 | 72.4 | 2.5 | −9.4 | 284.7 | 9.7 | 92B | Violet-Blue |
| 1746-36 | 72.5 | 7.5 | −11.2 | 303.7 | 13.5 | 85A | Violet |
| 1746-37 | 74.5 | 11.2 | −7.6 | 325.8 | 13.5 | N80C | Purple-Violet |
| 1746-38 | 64.8 | 4.7 | −15.1 | 287.4 | 15.8 | 94B | Violet-Blue |
| 1762-03 | 69.9 | 2.4 | −11.2 | 282.0 | 11.5 | 91B-C | Violet-Blue |
| 1762-06 | 74.2 | 7.6 | −5.5 | 324.2 | 9.3 | N80D | Purple-Violet |
| 1762-11 | 78.9 | 1.6 | −2.8 | 299.2 | 3.2 | 85D | Violet |
| 1762-17 | 77.8 | 5.4 | −5.6 | 313.9 | 7.8 | N88D | Violet |

* Mean value (n = 23)
NA: Not analyzable or measurable

Example 14: Introduction of pB438 into *Chrysanthemum* Variety "Taihei" (Coexpression of *Campanula* F3'5'H Gene Under the Control of *Chrysanthemum* F3H Promoter 1k and *Agrobacterium* Nos Terminator, and the *Clitoria* A3's'GT Gene and *Clitoria* DFR Gene Under the Control of *Chrysanthemum* F3H Promoter 1k and *Arabidopsis* HSP Terminator)

[1] Vector Assembly

An expression cassette obtained by digesting pMCE5-2 ADHNF-CtDFR obtained in Example 7 with AscI and PmeI was linked with a pB425 binary vector DNA fragment obtained by digestion with AscI and SwaI, to obtain pB438 (pBCam2+CtA3'5'GT+CtDFR).

[2] Obtaining Transformants and Measuring Flower Color

Plasmid pB438-transferred *Agrobacterium* EHA105 (provided by Dr. Elizabeth E. Hood) was used for transformation of the pink medium-sized *chrysanthemum* variety "Taipei" (sampled genetic resource maintained by aseptic culture at the NARO Institute of Floricultural Science), and 55 transformant lines were obtained. As a result of color measurement with a spectroscopic colorimeter (CD100, Yokogawa Electric Corp.) and an RHS color chart, alteration of flower color toward blue was found in 34 lines (62%). Blue color with a hue angle of ≤290° was exhibited in 13 of the lines (24% of the total). In 18 lines (33% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 14.

TABLE 14

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| Ohira wild type * | 79.5 | 9.7 | −2.0 | 356.6 | 11.1 | 65B, N74C, 75B | Red-Purple/Purple |
| Ohira transformants | | | | | | | |
| 1747-01 | 71.8 | 7.2 | −8.6 | 309.6 | 11.2 | N82D | Purple-Violet |
| 1747-02 | 69.5 | 2.0 | −11.2 | 280.1 | 11.4 | 96D | Violet-Blue |
| 1747-04 | 64.2 | 2.2 | −14.9 | 278.6 | 15.1 | 96D | Violet-Blue |
| 1747-05 | 71.8 | 2.5 | −13.6 | 280.5 | 13.8 | 96D | Violet-Blue |
| 1747-07 | 80.1 | 0.8 | −4.2 | 280.4 | 4.3 | 91B-C | Violet-Blue |
| 1747-08 | 71.1 | 7.4 | −9.0 | 309.4 | 11.7 | N82C | Purple-Violet |

TABLE 14-continued

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| 1747-09 | 78.0 | 7.6 | −2.9 | 339.2 | 8.2 | N80D | Purple-Violet |
| 1747-11 | 74.8 | 11.9 | −7.6 | 327.5 | 14.1 | N80D | Purple-Violet |
| 1747-13 | 71.9 | 4.7 | −9.3 | 296.5 | 10.4 | 91A-B | Violet-Blue |
| 1747-14 | 69.2 | 8.0 | −12.1 | 303.5 | 14.5 | N88C | Violet |
| 1747-15 | 65.2 | 4.1 | −16.7 | 283.8 | 17.2 | 96C-D | Violet-Blue |
| 1747-16 | 70.1 | 12.2 | −7.5 | 328.5 | 14.3 | N80C | Purple-Violet |
| 1747-17 | 66.9 | 2.6 | −11.7 | 282.3 | 12.0 | 92B | Violet-Blue |
| 1747-19 | 77.0 | −0.4 | −5.4 | 274.0 | 5.4 | 92C-D | Violet-Blue |
| 1747-22 | 78.7 | 5.3 | −4.5 | 319.7 | 6.9 | 85A | Violet |
| 1747-23 | 72.1 | 3.9 | −9.0 | 293.3 | 9.8 | N88C | Violet |
| 1747-24 | 77.2 | 4.1 | −5.0 | 309.4 | 6.4 | N82D | Purple-violet |
| 1747-29 | 72.4 | 7.2 | −6.7 | 317.1 | 9.9 | N87C-D | Violet |
| 1747-34 | 68.0 | 4.6 | −9.9 | 295.2 | 10.9 | 91A-B | Violet-Blue |
| 1747-35 | 71.0 | 1.9 | −12.0 | 279.0 | 12.2 | 97A | Violet-Blue |
| 1747-43 | 67.3 | 7.0 | −10.3 | 304.2 | 12.5 | 85A | Violet |
| 1747-44 | 63.2 | 5.0 | −18.6 | 284.9 | 19.3 | 93D | Violet-Blue |
| 1747-45 | 71.1 | 3.8 | −9.3 | 292.2 | 10.0 | 85B | Violet |
| 1747-46 | 60.5 | 2.4 | −16.3 | 278.5 | 16.4 | 96C-D | Violet-Blue |
| 1747-47 | 75.4 | 3.6 | −7.3 | 295.9 | 8.1 | 85B-C | Violet |
| 1747-48 | 65.4 | 2.8 | −13.7 | 281.7 | 14.0 | 96D | Violet-Blue |
| 1747-49 | 69.5 | 4.5 | −10.1 | 294.2 | 11.1 | 91A-B | Violet-Blue |
| 1747-52 | 73.5 | 5.6 | −10.6 | 297.9 | 12.0 | 91A | Violet-Blue |
| 1747-53 | 67.5 | 3.2 | −13.0 | 283.9 | 13.4 | 96D | Violet-Blue |
| 1747-55 | 62.6 | 9.7 | −17.7 | 298.6 | 20.2 | 92A | Violet-Blue |
| 1747-56 | 73.5 | 5.0 | −7.8 | 302.7 | 9.3 | N88D | Violet |
| 1747-59 | 71.3 | 4.2 | −8.6 | 296.1 | 9.6 | 85B | Violet |
| 1747-60 | 62.4 | 2.8 | −17.8 | 278.8 | 18.0 | 96D | Violet-Blue |
| 1747-63 | 80.4 | 5.2 | −1.3 | 345.9 | 5.4 | N81D | Purple-Violet |

* Mean value (n = 23)

Example 15: Introduction of pB426 into Chrysanthemum Variety "Taihei" (Coexpression of Campanula F3'5'H Gene Under the Control of Chrysanthemum F3H Promoter 1k and Agrobacterium Nos Terminator, and Delphinium DFR Gene and Clitoria A3's'GT Gene Under the Control of Chrysanthemum F3H Promoter 1k and Arabidopsis HSP Terminator)

[1] Vector Assembly

An expression cassette obtained by digesting pMCE5-2 ADHNF-DbDFR obtained in Example 6 with FseI and PmeI was linked with a pB315 binary vector DNA fragment obtained by digestion with FseI and SwaI, to obtain pBCam2+DbDFR. A DNA fragment obtained by digesting this binary vector with FseI and SwaI was linked with a CmF3Hp1k:ADHNF-CtA3'5'GT:AtHSPt cassette obtained by digesting pMCE5-2 ADHNF-CtA3'5'GT with FseI and PmeI, to obtain pB426 (pBCam2+DbDFR+CtA3'5'GT).

[2] Obtaining Transformants and Measuring Flower Color

Plasmid pB426-transferred Agrobacterium EHA105 (provided by Dr. Elizabeth E. Hood) was used for transformation of the pink medium-sized chrysanthemum variety "Taihei" (sampled genetic resource maintained by aseptic culture at the NARO Institute of Floricultural Science), and 47 transformant lines were obtained. As a result of color measurement with a spectroscopic colorimeter (CD100, Yokogawa Electric Corp.) and an RHS color chart, alteration of flower color toward blue was found in 28 lines (60%). In 9 lines (19% of the total), blue color with a hue angle of ≤290° was exhibited, and in 10 lines (21% of the total), flower color in the Violet-Blue group of the RHS color chart was exhibited in color measurement. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 15.

TABLE 15

| | CIEL*a*b* color system | | | | | RHS color chart | |
|---|---|---|---|---|---|---|---|
| | | | | Hue angle | Chroma | Chart | Color |
| Line No. | L | A | B | (hue °) | (C) | No. | group |
| Ohira wild type * | 79.5 | 9.7 | −2.0 | 356.6 | 11.1 | 65B, N74C, 75B | Red-Purple/Purple |
| Ohira transformants | | | | | | | |
| 1742-02 | 71.2 | 2.2 | −10.1 | 282.3 | 10.3 | NA | NA |
| 1742-03 | 71.5 | 10.4 | −9.9 | 316.4 | 14.3 | N82C-D | Purple-Violet |

TABLE 15-continued

| | | | | CIEL*a*b* color system | | RHS color chart | |
|---|---|---|---|---|---|---|---|
| | | | | Hue | | | |
| Line No. | L | A | B | angle (hue °) | Chroma (C) | Chart No. | Color group |
| 1742-04 | 60.3 | 3.9 | −14.7 | 284.9 | 15.3 | 92A-B | Violet-Blue |
| 1742-05 | 74.7 | 2.5 | −10.3 | 283.9 | 10.6 | 91B | Violet-Blue |
| 1742-07 | 79.4 | 4.5 | −4.7 | 314.0 | 6.5 | 76B | Purple |
| 1742-08 | 69.7 | 3.0 | −10.7 | 285.5 | 11.1 | 92B | Violet-Blue |
| 1742-10 | 79.4 | 3.6 | −4.0 | 312.0 | 5.4 | N82D | Purple-Violet |
| 1742-13 | 54.0 | 2.8 | −19.6 | 278.2 | 19.8 | 96B | Violet Blue |
| 1742-14 | 59.6 | 12.5 | −14.4 | 310.9 | 19.0 | N87B | Violet |
| 1742-18 | 75.9 | 2.0 | −7.3 | 284.9 | 7.6 | 92B | Violet-Blue |
| 1742-20 | 68.3 | 7.5 | −9.4 | 308.4 | 12.1 | N87C-D | Violet |
| 1742-22 | 70.8 | 3.9 | −9.0 | 293.3 | 9.8 | 91B | Violet-Blue |
| 1742-23 | 60.9 | 5.3 | −21.2 | 284.0 | 21.9 | 96C-D | Violet-Blue |
| 1742-24 | 61.8 | 5.2 | −16.5 | 287.4 | 17.3 | 92B | Violet-Blue |
| 1742-25 | 73.5 | 5.5 | −9.1 | 301.2 | 10.6 | N88C | Violet |
| 1742-26 | 66.4 | 11.5 | −8.8 | 322.6 | 14.4 | N80C | Purple-Violet |
| 1742-28 | 74.9 | 8.4 | −5.7 | 326.0 | 10.1 | 84B-C | Violet |
| 1742-30 | 74.5 | 8.1 | −7.5 | 317.1 | 11.0 | N82D | Purple-Violet |
| 1742-31 | 66.7 | 6.9 | −15.6 | 293.8 | 17.1 | 92A-B | Violet-Blue |
| 1742-33 | 76.8 | 5.0 | −4.4 | 318.6 | 6.6 | 76B | Purple |
| 1742-34 | 75.7 | 2.8 | −6.6 | 293.1 | 7.1 | 85B | Violet |
| 1742-36 | 65.5 | 5.2 | −9.4 | 299.0 | 10.8 | 85B-C | Violet |
| 1742-37 | 72.5 | 5.8 | −8.9 | 303.1 | 10.6 | 85B | Violet |
| 1742-38 | 72.7 | 6.0 | −8.4 | 305.5 | 10.3 | N82D | Purple-Violet |
| 1742-39 | 66.7 | 3.1 | −15.0 | 281.9 | 15.3 | 96C-D | Violet-Blue |
| 1742-44 | 74.4 | 5.8 | −6.7 | 310.7 | 8.8 | N87C | Violet |
| 1761-07 | 74.9 | 9.1 | −9.7 | 313.1 | 13.3 | 85A | Violet |
| 1761-08 | 74.0 | 7.3 | −6.3 | 318.9 | 9.6 | 76A | Purple |

* Mean value (n = 23)
NA: Not analyzable or measurable

Example 16: Introduction of pB427 into *Chrysanthemum* Variety "Taihei" (Coexpression of *Campanula* F3'5'H Gene Under the Control of *Chrysanthemum* F3H Promoter 1k and *Agrobacterium* Nos Terminator, and the *Clitoria* DFR Gene and *Clitoria* A3'5'GT Gene Under the Control of *Chrysanthemum* F3H Promoter 1k and *Arabidopsis* HSP Terminator)

[1] Vector Assembly

An expression cassette obtained by digesting pMCE5-2 ADHNF-CtDFR obtained in Example 7 with FseI and PmeI was linked with a pB315 binary vector DNA fragment obtained by digestion with FseI and SwaI, to obtain pBCam2+CtDFR. A DNA fragment obtained by digesting this binary vector with FseI and SwaI was linked with a CmF3Hp1k:ADHNF-CtA3'5'GT:AtHSPt cassette obtained by digesting pMCE5-2 ADHNF-CtA3'5'GT with FseI and PmeI, to obtain pB427 (pBCam2+CtDFR+CtA3'5'GT).

[2] Obtaining Transformants and Measuring Flower Color

Plasmid pB427-transferred *Agrobacterium* EHA105 (provided by Dr. Elizabeth E. Hood) was used for transformation of the pink medium-sized *chrysanthemum* variety "Taihei" (sampled genetic resource maintained by aseptic culture at the NARO Institute of Floricultural Science), and 24 transformant lines were obtained. As a result of color measurement with a spectroscopic colorimeter (CD100, Yokogawa Electric Corp.) and an RHS color chart, alteration of flower color toward blue was found in 15 lines (63%). In 4 lines (17% of the total), blue with a hue angle of ≤290° was exhibited, and flower color in the Violet-Blue group of the RHS color chart was exhibited. In the lines with the blue flower trait, accumulation of the major anthocyanins delphinidin 3-(6''-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 16.

TABLE 16

| | | | | CIEL*a*b* color system | | RHS color chart | |
|---|---|---|---|---|---|---|---|
| | | | | Hue | | | |
| Line No. | L | A | B | angle (hue °) | Chroma (C) | Chart No. | Color group |
| Ohira wild type * | 79.5 | 9.7 | −2.0 | 356.6 | 11.1 | 65B, N74C, 75B | Red-Purple/ Purple |
| Ohira transformants | | | | | | | |
| 1743-10 | 74.2 | 6.2 | −6.5 | 313.6 | 9.0 | N78C | Purple |
| 1743-31 | 76.7 | 2.4 | −5.0 | 295.5 | 5.5 | 85B | Violet |
| 1743-32 | 72.8 | 3.2 | −5.8 | 299.1 | 6.6 | NA | NA |
| 1743-36 | 71.0 | 4.5 | −7.8 | 300.3 | 9.0 | 85A | Violet |

TABLE 16-continued

| | CIEL*a*b* color system | | | | | RHS color chart | |
|---|---|---|---|---|---|---|---|
| Line No. | L | A | B | Hue angle (hue °) | Chroma (C) | Chart No. | Color group |
| 1743-38 | 75.8 | 2.4 | −6.2 | 291.5 | 6.7 | 85B | Violet |
| 1743-40 | 70.9 | 9.5 | −12.7 | 307.0 | 15.9 | 85A | Violet |
| 1743-41 | 67.4 | 8.2 | −13.3 | 301.6 | 15.6 | 85A | Violet |
| 1743-43 | 60.9 | 4.0 | −18.4 | 282.4 | 18.8 | 94B | Violet-Blue |
| 1743-44 | 77.5 | 2.9 | −3.5 | 309.7 | 4.6 | N82D | Violet |
| 1743-46 | 75.2 | 7.2 | −6.7 | 317.2 | 9.8 | 76A-B | Purple |
| 1743-47 | 73.6 | 8.8 | −9.1 | 313.9 | 12.7 | 85A | Violet |
| 1743-48 | 68.5 | 6.6 | −11.4 | 300.3 | 13.2 | 85A | Violet |
| 1743-49-1 | 64.9 | 4.2 | −17.0 | 283.8 | 17.5 | 94B | Violet-Blue |
| 1743-49-2 | 62.8 | 3.5 | −15.7 | 282.5 | 16.1 | 96D | Violet-Blue |
| 1743-50 | 75.4 | −0.6 | −5.2 | 264.0 | 5.3 | 97B-C | Violet-Blue |

* Mean value (n = 23)
NA: Not analyzable or measurable

Example 17: Introduction of pB419 into Chrysanthemum Variety "Taihei" (Coexpression of Campanula F3'5'H Gene Under the Control of Chrysanthemum F3H Promoter 1k and Agrobacterium Nos Terminator, and the Clitoria AGS Gene and Clitoria A3's'GT Gene Under the Control of Chrysanthemum F3H Promoter 1k and Arabidopsis HSP Terminator)

[1] Vector Assembly

A DNA fragment obtained by digesting pBSII-ADH-CtA3'S'GT with NheI and EcoICRI was linked with a vector fragment obtained by digesting pMCE5-2 (FASS-CmF3Hp-AtHSPt) with NheI and EcoICRI, to obtain pMCE5-2 ADHNF-CtA3'5'GT. An expression cassette obtained by digesting this plasmid with FseI and PmeI was linked with a binary vector fragment of pB420 (pBCam2+CtAGS; Reference Example 4) obtained by digestion with FseI and SwaI, to obtain pB419 (pBCam2+CtAGS+CtA3'5'GT).

[2] Obtaining Transformants and Measuring Flower Color

Plasmid pB419-transferred Agrobacterium EHA105 (provided by Dr. Elizabeth E. Hood) was used for transformation of the pink medium-sized chrysanthemum variety "Taihei" (sampled genetic resource maintained by aseptic culture at the NARO Institute of Floricultural Science), and 20 transformant lines were obtained. As a result of color measurement with a spectroscopic colorimeter (CD100, Yokogawa Electric Corp.) and an RHS color chart, alteration of flower color toward blue was found in 12 lines (60%). Blue color with a hue angle of ≤290° was exhibited in 5 of the lines (25% of the total). In 3 lines (15% of the total), flower color in the Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 17.

TABLE 17

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/ Purple |
| Ohira transformants | | | | | | | |
| 1732-01 | 64.7 | 3.3 | −15.3 | 282.3 | 15.6 | 96C-D | Viole-Blue |
| 1732-04 | 75.2 | 4.2 | −6.8 | 301.9 | 8.0 | 85A | violet |
| 1732-06 | 75.5 | 3.3 | −6.4 | 297.2 | 7.2 | 85B | Violet |
| 1732-08 | 72.4 | 2.4 | −9.0 | 285.1 | 9.3 | 85B | Violet |
| 1732-11 | 74.7 | 9.3 | −6.3 | 325.6 | 11.2 | N80C-D | Purple-Violet |
| 1732-12 | 61.9 | 3.9 | −18.5 | 281.9 | 18.9 | 96C-D | Violet-Blue |
| 1732-13 | 72.7 | 6.0 | −6.5 | 312.9 | 8.9 | 85A-B | Violet |
| 1732-14 | 72.6 | 6.9 | −8.5 | 309.0 | 11.0 | 85A | Violet |
| 1732-15 | 73.4 | 2.8 | −8.9 | 287.4 | 9.3 | 91B | Violet-Blue |
| 1732-16 | 73.1 | 5.9 | −7.8 | 307.3 | 9.8 | 85A-B | Violet |
| 1732-17 | 73.6 | 3.3 | −9.9 | 288.3 | 10.4 | NA | NA |
| 1732-21 | 80.6 | 9.0 | −4.1 | 335.6 | 9.9 | N80D | Purple-Violet |

* Mean value (n = 23)
NA: Not analyzable or measurable

Example 18: Introduction of pB432 into
Chrysanthemum Variety "Taihei" (Coexpression of
Campanula F3'5'H Gene Under the Control of
Chrysanthemum F3H Promoter 1k and
Agrobacterium Nos Terminator, and the Clitoria
AGS Gene, Clitoria A3's'GT Gene and Dutch Iris
DFR Gene Under the Control of Chrysanthemum
F3H Promoter 1k and Arabidopsis HSP Terminator)

[1] Vector Assembly

An expression cassette obtained by digesting pMCE5-2-ADHNF-DbDFR with FseI and PmeI was linked with a binary vector fragment of pB419 (pBCam2+CtAGS+CtA3'S'GT) obtained by digestion with FseI and SwaI, to obtain pB432 (pBCam2+CtAGS+CtA3'5'GT+IhDFR).

[2] Obtaining Transformants and Measuring Flower Color

Plasmid pB432-transferred Agrobacterium EHA105 (provided by Dr. Elizabeth E. Hood) was used for transformation of the pink medium-sized chrysanthemum variety "Taihei" (sampled genetic resource maintained by aseptic culture at the NARO Institute of Floricultural Science), and 47 transformant lines were obtained. As a result of color measurement with a spectroscopic colorimeter (CD100, Yokogawa Electric Corp.) and an RHS color chart, alteration of flower color toward blue was found in 23 lines (49%). Blue color with a hue angle of ≤290° was exhibited in 12 of the lines (26% of the total). In 13 lines (28% of the total), flower color in the Blue group or Violet-Blue group of the RHS color chart was exhibited. In the lines with the blue flower trait, accumulation of the major anthocyanins delphinidin 3-(6"-malonyl)glucoside-3',5'-diglucoside (ternatin C5) and delphinidin 3,3',5'-triglucoside (preternatin C5) was confirmed. The measured values for the transformants confirmed to have modification of flower color toward blue are shown below in Table 18.

TABLE 18

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| Ohira wild type * | 79.5 | 9.7 | −2.0 | 356.6 | 11.1 | 65B, N74C, 75B | Red-Purple/ Purple |
| | | | | Ohira transformants | | | |
| 1740-02 | 64.8 | 3.6 | −16.5 | 282.2 | 16.9 | 96C-D | Violet-Blue |
| 1740-03 | 69.0 | 13.2 | −11.7 | 318.5 | 17.7 | N81B-C | Purple-Violet |
| 1740 05 | 68.0 | 2.3 | 12.0 | 280.9 | 12.3 | 91B-C | Violet-Blue |
| 1740-08 | 74.2 | 7.7 | −2.2 | 344.1 | 8.0 | N80C | Purple-Violet |
| 1740-09 | 66.8 | 4.8 | −14.4 | 288.4 | 15.2 | 94B | Violet-Blue |
| 1740-10 | 72.4 | 5.3 | −10.9 | 295.8 | 12.1 | 92B | Violet-Blue |
| 1740-18 | 58.9 | 5.3 | −21.0 | 284.1 | 21.7 | 96D | Violet-Blue |
| 1740-19 | 49.9 | 23.7 | −22.1 | 316.9 | 32.4 | N82A-B | Purple-Violet |
| 1740-20 | 67.4 | 11.3 | −10.7 | 316.4 | 15.6 | N82B | Purple-Violet |
| 1740-21 | 71.0 | 7.0 | 9.5 | 306.4 | 11.8 | N88C | Violet |
| 1740-22 | 70.3 | 6.3 | −12.4 | 296.8 | 13.9 | N88C-D | Violet |
| 1740-23 | 72.5 | 3.2 | −10.2 | 287.2 | 10.7 | 91A-B | Violet-Blue |
| 1740-24 | 61.9 | 13.0 | −8.1 | 328.0 | 15.4 | N80C | Purple-Violet |
| 1740-25 | 75.2 | 3.9 | −7.6 | 296.9 | 8.6 | 85B | Violet |
| 1740-26 | 67.9 | 6.0 | −6.4 | 312.9 | 8.8 | N88C | Violet |
| 1740-29 | 61.5 | 4.1 | −14.7 | 285.7 | 15.3 | 94B-C | Violet-Blue |
| 1740-35 | 64.6 | 4.2 | −16.1 | 284.6 | 16.6 | 94B-C | Violet-Blue |
| 1740-37 | 64.8 | 2.2 | −16.6 | 277.4 | 16.7 | 96D | Violet-Blue |
| 1740-38 | 72.0 | 2.8 | −11.4 | 284.0 | 11.7 | 94C-D | Violet-Blue |
| 1740-40 | 74.3 | 0.6 | −9.5 | 273.5 | 9.5 | 96D | Violet-Blue |
| 1740-43 | 50.5 | 4.2 | −24.7 | 279.7 | 25.0 | 99B-C | Blue |
| 1740-54 | 43.1 | 28.0 | −23.6 | 319.8 | 36.6 | 83B | Violet |
| 1740-57 | 63.5 | 3.7 | −18.9 | 281.1 | 19.3 | 96B-C | Violet-Blue |

* Mean value (n = 23)

Example 19: Introduction of pB423 into the Chrysanthemum Variety "Sei Shawl" (Coexpression of Clitoria A3'5'GT Gene Under the Control of Chrysanthemum F3H Promoter 1k and Agrobacterium Nos Terminator and Campanula F3'5'H Gene Under the Control of Chrysanthemum F3H Promoter 1k and Arabidopsis HSP Terminator)

[1] Vector Assembly

Plasmid pB423 (pBCtA3'5'GT+CamF3'5'H) was created according to Example 1.

[2] Obtaining Transformants and Measuring Flower Color

The pink-colored large-sized decorative chrysanthemum variety "Sei Shawl" (Inochio Seikoen) was transformed using pB423-transferred Agrobacterium EHA105 (provided by Dr. Elizabeth E. Hood), and 2 transformant lines were obtained. The results of color measurement with a spectroscopic colorimeter (CD100, Yokogawa Electric Corp.) and an RHS color chart indicated that blue chrysanthemum having a hue angle of ≤290° and exhibiting color in the Violet-Blue group according to the RHS color chart had been created in 1 line (50%). The measured values for the transformants confirmed to have modification of flower color toward blue are shown below in Table 19.

TABLE 19

| | CIEL*a*b* color system | | | | | RHS color chart | |
|---|---|---|---|---|---|---|---|
| Line No. | L | A | B | Hue angle (hue °) | Chroma (C) | RHCCC | Color group |
| Sei Shawl wild type | 80.5 | 11.4 | −1.1 | 354.5 | 11.5 | N74C | Red-Purple |
| Sei Shawl transformants | | | | | | | |
| 2022-01 | 83.0 | 0.5 | −2.2 | 282.2 | 2.3 | NA | NA |

NA: Not analyzable or measurable

Example 20: Introduction of pB423 into Chrysanthemum Variety "Candela Tierra" (Coexpression of Clitoria A3'5'GT Gene Under the Control of Chrysanthemum F3H Promoter 1k and Agrobacterium Nos Terminator and Campanula F3's'H Gene Under the Control of Chrysanthemum F3H Promoter 1k and Arabidopsis HSP Terminator)

[1] Vector Assembly

Plasmid pB423 (pBCtA3'5'GT+CamF3'S'H) was created according to Example 1.

[2] Obtaining Transformants and Measuring Flower Color

The pink-colored decorative chrysanthemum variety "Candela Tierra" (Inochio Seikoen) was transformed using pB423-transferred Agrobacterium EHA105 (provided by Dr. Elizabeth E. Hood), and 3 transformant lines were obtained. The results of color measurement with a spectroscopic colorimeter (CD100, Yokogawa Electric Corp.) and an RHS color chart indicated that blue chrysanthemum exhibiting color in the Violet-Blue group according to the RHS color chart had been created in 1 line (33%). The measured values for the transformants confirmed to have modification of flower color toward blue are shown below in Table 20.

TABLE 20

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Candela Tierra wild type | 54.7 | 30.9 | −12.0 | 338.8 | 33.1 | 71B | Red-Purple |
| Candela Tierra transformants | | | | | | | |
| 1946-03 | 56.8 | 8.3 | −21.8 | 290.8 | 23.3 | 96B | Violet-Blue |
| 1985-04 | 53.3 | 7.5 | −17.4 | 293.2 | 19.0 | NA | NA |
| 2052-07 | 54.2 | 14.4 | −19.0 | 307.1 | 23.8 | NA | NA |

NA: Not analyzable or measurable

Example 21: Introduction of pB423 into Chrysanthemum Line "T10" (Coexpression of Clitoria A3'5'GT Gene Under the Control of Chrysanthemum F3H Promoter 1k and Agrobacterium Nos Terminator and Campanula F3'5'H Gene Under the Control of Chrysanthemum F3H Promoter 1k and Arabidopsis HSP Terminator)

[1] Vector Assembly

Plasmid pB423 (pBCtA3'5'GT+CamF3'5'H) was created according to Example 1.

[2] Obtaining Transformants and Measuring Flower Color

The crimson-colored decorative chrysanthemum line "T10" (sampled breeding line provided by Inochio Seikoen) was transformed using pB423-transferred Agrobacterium EHA105 (provided by Dr. Elizabeth E. Hood), and 3 transformant lines were obtained. The results of color measurement with a spectroscopic colorimeter (CD100, Yokogawa Electric Corp.) and an RHS color chart indicated that blue chrysanthemum exhibiting color in the Violet-Blue group according to the RHS color chart had been created in 1 line (33%). The measured values for the transformants confirmed to have modification of flower color toward blue are shown below in Table 21.

TABLE 21

| | CIEL*a*b* color system | | | | | RHS color chart | |
|---|---|---|---|---|---|---|---|
| Line No. | L | A | B | Hue angle (hue °) | Chroma (C) | Chart No. | Color group |
| T10 wild type | 31.1 | 43.1 | −10.3 | 346.5 | 44.3 | 71A | Red-Purple |
| T10 transformants | | | | | | | |
| 1945-01 | 32.0 | 16.1 | 31.2 | 297.3 | 35.1 | N89B | Violet-Blue |
| 2051-01 | 21.9 | 25.5 | −16.0 | 327.9 | 30.1 | NA | NA |

NA: Not analyzable or measurable

Example 22: Introduction of pB423 into *Chrysanthemum* Line "T24" (Coexpression of *Clitoria* A3'5'GT Gene Under the Control of *Chrysanthemum* F3H Promoter 1k and *Agrobacterium* Nos Terminator and *Campanula* F3'5'H Gene Under the Control of *Chrysanthemum* F3H Promoter 1k and *Arabidopsis* HSP Terminator)

[1] Vector Assembly

Plasmid pB423 (pBCtA3'5'GT+CamF3'5'H) was created according to Example 1.

[2] Obtaining Transformants and Measuring Flower Color

The pink-colored large-sized atsumono *chrysanthemum* line "T24" (sampled breeding line provided by Inochio Seikoen) was transformed using pB423-transferred *Agrobacterium* EHA105 (provided by Dr. Elizabeth E. Hood), and 4 transformant lines were obtained. The results of color measurement with a spectroscopic colorimeter (CD100, Yokogawa Electric Corp.) and an RHS color chart indicated that blue *chrysanthemum* having a hue angle of ≤290° and exhibiting color in the Violet-Blue group according to the RHS color chart had been created in 1 line (25%). The measured values for the transformants confirmed to have modification of flower color toward blue are shown below in Table 22.

TABLE 22

| | CIEL*a*b* color system | | | | | RHS color chart | |
|---|---|---|---|---|---|---|---|
| Line No. | L | A | B | Hue angle (hue °) | Chroma (C) | Chart No. | Color group |
| T24 wild type | 44.6 | 39.3 | −14.6 | 339.6 | 41.9 | N74B-C | Red-Purple |
| T24 transformants | | | | | | | |
| 1999-01 | 65.1 | 1.5 | −17.5 | 274.9 | 17.6 | 100D | Blue |
| 2044-01 | 60.0 | 6.4 | −13.0 | 296.0 | 14.5 | NA | NA |
| 1999-02 | 68.1 | 9.6 | −6.5 | 325.9 | 11.6 | 82D | Purple-Violet |
| 2019-01 | 76.8 | 10.7 | −1.3 | 353.1 | 10.8 | NA | NA |

NA: Not analyzable or measurable

Example 23: Introduction of pB423 into *Chrysanthemum* Line "T27" (Coexpression of *Clitoria* A3'5'GT Gene Under the Control of *Chrysanthemum* F3H Promoter 1k and *Agrobacterium* Nos Terminator and *Campanula* F3'5'H Gene Under the Control of *Chrysanthemum* F3H Promoter 1k and *Arabidopsis* HSP Terminator)

[1] Vector Assembly

Plasmid pB423 (pBCtA3'5'GT+CamF3'5'H) was created according to Example 1.

[2] Obtaining Transformants and Measuring Flower Color

A pink-colored pompon *chrysanthemum* line "T27" (sampled breeding line provided by Inochio Seikoen) was transformed using pB423-transferred *Agrobacterium* EHA105 (provided by Dr. Elizabeth E. Hood), and 21 transformant lines were obtained. The results of color measurement with a spectroscopic colorimeter (CD100, Yokogawa Electric Corp.) and an RHS color chart indicated that blue *chrysanthemum* had been created having a hue angle of ≤290° in 11 lines (52%), and exhibiting color in the Violet-Blue group according to the RHS color chart in 17 lines (81%). The measured values for the transformants confirmed to have modification of flower color toward blue are shown below in Table 23.

TABLE 23

| | CIEL*a*b* color system | | | | | RHS color chart | |
|---|---|---|---|---|---|---|---|
| Line No. | L | A | B | Hue angle (hue °) | Chroma (C) | Chart No. | Color group |
| T27 wild type | 75.1 | 16.9 | −4.6 | 344.8 | 17.5 | 73B | Red-Purple |
| T27 transformants | | | | | | | |
| 1964-01 | 60.3 | 3.8 | −16.4 | 283.2 | 16.3 | 96C | Violet-Blue |
| 1964-04 | 72.9 | 6.3 | −4.8 | 323.0 | 7.9 | 84A-B | Violet |

TABLE 23-continued

| | | | | CIEL*a*b* color system | | RHS color chart | |
|---|---|---|---|---|---|---|---|
| | | | | | Hue | | |
| Line No. | L | A | B | angle (hue °) | Chroma (C) | Chart No. | Color group |
| 1964-05 | 62.9 | 4.3 | −16.2 | 284.9 | 16.7 | 96C-D | Violet-Blue |
| 1964-06 | 62.0 | 6.2 | −16.3 | 290.6 | 17.5 | 94B | Violet-Blue |
| 1964-07 | 62.0 | 6.7 | −15.7 | 293.2 | 17.1 | 92A | Violet-Blue |
| 1964-08 | 65.5 | 4.9 | −12.0 | 292.2 | 12.9 | 96C-D | Violet-Blue |
| 1964-09 | 57.4 | 3.7 | −14.8 | 284.1 | 15.3 | 96C-D | Violet-Blue |
| 1964-10 | 66.5 | 2.9 | −4.6 | 301.8 | 5.5 | 96C-D | Violet-Blue |
| 1964-11 | 55.2 | 4.4 | −17.3 | 284.4 | 17.8 | 96O | Violet-Blue |
| 1964-12 | 61.9 | 7.5 | −11.1 | 304.0 | 13.4 | 91A | Violet-Blue |
| 1964-13 | 62.1 | 4.5 | −11.7 | 290.8 | 12.5 | 85B-C | Violet |
| 1974-01 | 55.9 | 2.0 | −11.4 | 279.9 | 11.6 | 97A | Violet-Blue |
| 1974-02 | 61.9 | 4.0 | −16.2 | 283.8 | 16.7 | 97A | Violet-Blue |
| 1974-03 | 62.2 | 4.2 | −13.1 | 287.8 | 13.81 | 93C-D | Violet-Blue |
| 1974-04 | 71.4 | 2.4 | −5.6 | 293.7 | 6.1 | 94B-C | Violet-Blue |
| 1974-06 | 63.0 | 0.8 | −8.5 | 275.0 | 8.6 | 94B | Violet-Blue |
| 1974-07 | 59.2 | 3.5 | −15.7 | 282.5 | 16.1 | 94C | Violet-Blue |
| 1974-08 | 68.8 | 4.1 | −6.9 | 300.9 | 8.0 | 85B-C | Violet |
| 1974-09 | 72.3 | 12.4 | −9.2 | 323.3 | 15.4 | N81C-D | Purple-Violet |
| 1974-12 | 59.9 | 2.0 | −8.4 | 283.4 | 8.6 | 91B | Violet-Blue |
| 2006-03 | 69.1 | 2.5 | −10.6 | 283.3 | 10.9 | 96D | Violet-Blue |

Example 24: Introduction of pB423 into *Chrysanthemum* Line "T44" (Coexpression of *Clitoria* A3'5'GT Gene Under the Control of *Chrysanthemum* F3H Promoter 1k and *Agrobacterium* Nos Terminator and *Campanula* F3'5'H Gene Under the Control of *Chrysanthemum* F3H Promoter 1k and *Arabidopsis* HSP Terminator)

[1] Vector Assembly

Plasmid pB423 (pBCtA3'5'GT+CamF3'5'H) was created according to Example 1.

[2] Obtaining Transformants and Measuring Flower Color

A pink-colored pompon *chrysanthemum* line "T44" (sampled breeding line provided by Inochio Seikoen) was transformed using pB423-transferred *Agrobacterium* EHA105 (provided by Dr. Elizabeth E. Hood), and 12 transformant lines were obtained. The results of color measurement with a spectroscopic colorimeter (CD100, Yokogawa Electric Corp.) and an RHS color chart indicated that blue *chrysanthemum* had been created having a hue angle of ≤290° in 4 lines (33%), and exhibiting color in the Violet-Blue group according to the RHS color chart in 3 lines (25%). The measured values for the transformants confirmed to have modification of flower color toward blue are shown below in Table 24.

TABLE 24

| | | | | CIEL*a*b* color system | | RHS color chart | |
|---|---|---|---|---|---|---|---|
| | | | | | Hue | | |
| Line No. | L | A | B | angle (hue °) | Chroma (C) | Chart No. | Color group |
| T44 wild type | 74.2 | 12.5 | −2.7 | 347.8 | 12.8 | 74D-75A | Red-Purple |
| T44 transformants | | | | | | | |
| 2032-02 | 70.1 | 2.8 | −3.5 | 309.1 | 4.5 | 85B-C | Violet |
| 2032-04 | 65.1 | 4.8 | −10.5 | 294.9 | 11.5 | 93CD | Violet-Blue |
| 2032-05 | 72.7 | 2.5 | −6.1 | 292.4 | 6.6 | 92B-C | Violet-Blue |
| 2032-06 | 71.3 | 5.1 | −3.4 | 326.7 | 6.1 | 85B-C | Violet |
| 2050-01 | 73.2 | 1.9 | −4.9 | 290.6 | 5.3 | NA | NA |
| 2050-04 | 78.1 | 0.5 | −4.0 | 276.7 | 4.1 | 95C-D | Violet-Blue |
| 2067-05 | 49.2 | 5.6 | −11.4 | 296.1 | 12.7 | NA | NA |
| 2067-01 | 68.2 | 1.6 | −7.1 | 282.3 | 7.3 | NA | NA |
| 2067-02 | 60.0 | 3.9 | −11.9 | 288.3 | 12.5 | NA | NA |
| 2050-06 | 43.6 | 6.3 | −12.5 | 296.6 | 14.0 | NA | NA |
| 2067-06 | 57.2 | 6.1 | −7.7 | 308.5 | 9.8 | NA | NA |
| 2067-07 | 69.1 | 3.5 | −11.6 | 286.9 | 12.1 | NA | NA |

NA: Not analyzable or measurable

Example 25: Introduction of pB423 into *Chrysanthemum* Line "T57" (Coexpression of *Clitoria* A3'5'GT Gene Under the Control of *Chrysanthemum* F3H Promoter 1k and *Agrobacterium* Nos Terminator and *Campanula* F3'5'H Gene Under the Control of *Chrysanthemum* F3H Promoter 1k and *Arabidopsis* HSP Terminator)

[1] Vector Assembly

Plasmid pB423 (pBCtA3'5'GT+CamF3'5'H) was created according to Example 1.

[2] Obtaining Transformants and Measuring Flower Color

The pink-colored decorative *chrysanthemum* line "T57" (sampled breeding line provided by Inochio Seikoen) was transformed using pB423-transferred *Agrobacterium* EHA105 (provided by Dr. Elizabeth E. Hood), and 2 transformant lines were obtained. The results of color measurement with a spectroscopic colorimeter (CD100, Yokogawa Electric Corp.) and an RHS color chart indicated that blue *chrysanthemum* exhibiting a hue angle of ≤290° and exhibiting color in the Violet-Blue group according to the RHS color chart had been created in 2 lines (100%). The measured values for the transformants confirmed to have modification of flower color toward blue are shown below in Table 25.

TABLE 25

| | CIEL*a*b* color system | | | | | RHS color chart | |
|---|---|---|---|---|---|---|---|
| Line No. | L | A | B | Hue angle (hue °) | Chroma (C) | Chart No. | Color group |
| T57 wild type | 74.4 | 16.9 | −5.5 | 341.9 | 17.8 | N74C | Red-Purple |
| T57 transformants | | | | | | | |
| 2037-01 | 58.8 | 6.0 | −20.2 | 286.4 | 21.1 | 94B | Violet-Blue |
| 2037-02 | 60.4 | 5.8 | −19.2 | 286.9 | 20.0 | 94A | Violet-Blue |

Reference Example 1: Introduction of pB248 into *Chrysanthemum* Line "94-765" (Expression of *Clitoria*-Derived A3'5'GT Gene Under the Control of *Chrysanthemum* F3H Promoter 500 and *Agrobacterium* Nos Terminator)

[1] Vector Assembly

A DNA fragment amplified by PCR using pBSCtBGT1DB24 plasmid, described in Japanese Patent No. 4418865 and containing the *Clitoria* A3'5'GT gene, as template, and ADH-3'5'GT-Fd (5'-CAAGAAAAATAAATGGAAAACAATAAGCATGTC-3';

underline indicates sequence annealing with Ct3'5'GT-coding region; SEQ ID NO: 26) and Hind-Ct3'5'GT-Rv (5'-AAGCTTGCGTTTTTAGCATCATTC-3'; SEQ ID NO: 27) as primers, and a DNA fragment amplified by PCR using pBI221 ADH-221 as template and XbaI-ADH-Fd (5'-ACGCGTTCTAGAGTCTATTTAACTCAGTATTC-3';

underline indicates sequence annealing with NtADH-5'UTR 94 bp; SEQ ID NO: 14) and Ct3'5'GT-ADH-Rv (5'-ATTGTTTTCCATTTATTTTTCTTGATTTCCTTCAC-3';

underline indicates sequence annealing with NtADH-5'UTR 94 bp; SEQ ID NO: 28) as primers, were combined and used as template for PCR using XbaI-ADH-Fd and Hind-Ct3'S'GT-Rv as primers, to obtain a DNA fragment having tobacco ADH-5'UTR 94 bp directly linked to the start codon of the *Clitoria* A3'5'GT gene. An approximately 600 bp DNA fragment, obtained by TA cloning of this DNA fragment in pCR2.1 followed by digestion with XbaI and HindIII, was linked with a vector DNA fragment obtained by digesting pBlueScript II SK(+) with XbaI and HindIII, to obtain pBSII-ADH-5'-CtBGT1-HindIII. A plasmid DNA fragment obtained by digesting this plasmid with HindIII and XhoI was linked with a DNA fragment obtained by digesting pBSCtBGT1DB24 with HindIII and XhoI, to obtain pBSII-ADH-CtA3'5'GT. A blunt-end DNA product, which had been amplified by PCR using the aforementioned plasmid as template and NheI-ADH-Fd2

(5'-GCTAGCGTCTATTTAACTCAGTATTCAGAAAC-3';

underline indicates sequence annealing with NtADH-5'UTR 94 bp; SEQ ID NO: 29) and Ct3'5'GT-SacI-Rv (5'-GAGCTCTTAGCTAGAGGAAATCATTTCCAC-3';

underline indicates sequence annealing with the Ct3'5'GT-coding region; SEQ ID NO: 30) as primers, was cloned in pCR-Blunt II-TOPO (Invitrogen) to obtain pCR ADHNF-CtA3'5'GT. An approximately 1450 bp ADHNF-CtA3'5'GT DNA fragment obtained by digesting this plasmid with NheI and EcoICRI was linked with a binary vector DNA fragment obtained by digesting pBI121 HANS-CmF3Hp500-X (Japanese Patent No. 5697040) with XbaI and EcoICRI, to obtain pB248 (pBI121 CmF3Hp500:ADHNF-*Clitoria* A3'5'GT: NOSt).

[2] Obtaining Transformants and Measuring Flower Color

Figure 6:
FIG. 6 is a set of photographs showing the flower colors of chrysanthemums into which CtA3'5'GT was transformed.

The dark red-colored medium-sized *chrysanthemum* line "94-765" (sampled breeding line provided by Inochio Seikoen) was transformed using pB248-transferred *Agrobacterium* EHA105 (provided by Dr. Elizabeth E. Hood), and 23 transformant lines were obtained. Of these, the anthocyanin pigments in the ligulate petals of 15 lines were analyzed by high-performance liquid chromatography under the following conditions. Isocratic elution was performed using Inertsil ODS-2 (particle diameter: 5 μm, 4.6×250 mm, GL Sciences Inc.) as the column, with a flow rate of 0.8 ml/min and a mobile phase containing 1.5% phosphoric acid, for 20 minutes with a linear concentration gradient from 5% acetic acid, 6.25% acetonitrile to 20% acetic acid, 25% acetonitrile, followed by 5 minutes with 25% acetonitrile containing 1.5% phosphoric acid and 20% acetic acid. Detection was performed using an Agilent 1100 Series diode array detector (GL Sciences Inc.) in a wavelength range from 250 nm to 600 nm. As a result of the analysis, 12 lines were confirmed to have two major pigments, cyanidin 3-(6-malonyl)glucoside-3'-glucoside and cyanidin 3-(3",6"-dimalonyl)glucoside-3'-glucoside (HPLC elution times (tR): 9.4 minutes and 7.2 min, respectively), which are thought to be the major anthocyanins of the host petals, cyanidin 3-(6"-malonyl)glucoside and cyanidin 3-(3",6"-dimalonyl) glucoside, with one glucosyl group bonded to each. However, no lines were obtained with any major flower color change from the original 94-765, and all of the transformed lines exhibited flower colors in the Red-Purple group according to the RHS color chart (Table 26). Blue chrysanthemum could not be obtained by expressing only the Clitoria A3'5'GT gene with Chrysanthemum F3H promoter 500 (length: ~500b) (FIG. 6).

Reference Example 2: Introduction of pB249 into Chrysanthemum Line "94-765" (Expression of Clitoria-Derived A3'5'GT Gene Under the Control of Chrysanthemum F3H Promoter 1k and Agrobacterium Nos Terminator)

[1] Vector Assembly

A binary vector DNA fragment obtained by digesting pBI121 HANS-CmF3Hp1k-S (Japanese Patent No. 5697040) with SpeI and EcoICRI was linked with a DNA fragment of ADHNF-Clitoria A3'5'GT obtained by digesting pCR ADHNF-CtA3'S'GT with NheI and EcoICRI, to obtain pB249 (pBI121 CmF3Hp1k:ADHNF-Clitoria A3'5'GT:NOSt).

[2] Obtaining Transformants and Measuring Flower Color

The dark red-colored medium-sized chrysanthemum line "94-765" (sampled breeding line provided by Inochio Seikoen) was transformed using pB249-transferred Agrobacterium EHA105 (provided by Dr. Elizabeth E. Hood), and 25 transformant lines were obtained. As a result of analyzing the anthocyanin pigments in the ligulate petals of 18 lines by the method of Reference Example 1, 17 lines were confirmed to have two major pigments thought to be cyanidin 3-(6"-malonyl)glucoside and cyanidin 3-(3",6"-dimalonyl) glucoside with one glucosyl group bonded to each. Moreover, no lines were obtained with any major flower color change from the original 94-765, and all of them exhibited flower colors in the Red-Purple group (Table 27). Blue chrysanthemum could not be obtained by expressing only the Clitoria A3'5'GT gene with Chrysanthemum F3H promoter 1k (length: ~1 kb) (FIG. 6).

TABLE 26

| Line No. | | | | RHS color chart | | CIEL*a*b* color system | | | | |
|---|---|---|---|---|---|---|---|---|---|---|
| Infection No. | Individual No. | HPLC* | | Chart | Color | | | | Hue angle | Chroma |
| | | 9.4 tR | 7.2 tR | No. | group | L | A | B | (hue °) | (C) |
| 94-765 Wild type ** | – | – | – | 64A-B 71A-B | Red-Purple | 34.5 | 38.0 | −7.0 | 350.1 | 38.7 |
| | | | | 94-765 transformants | | | | | | |
| 1355- | 1 | + | + | 71A | Red-Purple | 32.6 | 38.1 | −8.8 | 347.0 | 39.1 |
| 1355- | 3 | + | + | NA | NA | NA | NA | NA | NA | NA |
| 1355- | 4 | + | + | NA | NA | NA | NA | NA | NA | NA |
| 1355- | 6 | + | + | 72B | Red-Purple | 45.2 | 33.9 | −15.0 | 336.1 | 37.1 |
| 1355- | 7 | + | + | 72B | Red-Purple | 44.1 | 37.3 | −13.6 | 340.0 | 39.7 |
| 1355- | 9 | – | – | NA | NA | NA | NA | NA | NA | NA |
| 1355- | 11 | – | – | NA | NA | NA | NA | NA | NA | NA |
| 1355- | 12 | + | + | 70A-B | Red-Purple | 50.7 | 31.7 | −12.8 | 338.0 | 34.2 |
| 1355- | 13 | + | + | NA | NA | NA | NA | NA | NA | NA |
| 1355- | 14 | + | + | NA | NA | NA | NA | NA | NA | NA |
| 1355- | 17 | – | – | 71A | Red-Purple | NA | NA | NA | NA | NA |
| 1355- | 18 | + | + | NA | NA | NA | NA | NA | NA | NA |
| 1355- | 19 | + | + | NA | NA | NA | NA | NA | NA | NA |
| 1355- | 20 | + | + | NA | NA | NA | NA | NA | NA | NA |
| 1355- | 23 | + | + | 72A-B | Red-Purple | 33.9 | 37.4 | −15.8 | 337.1 | 40.5 |

*+: Detected, trace: trace amount or not detected, 9.4 tR: Cyanidin 3-(3,6-dimalonyl)glucoside-3'-glucoside, 7.2 tR: Cyanidin 3-(3-malonyl)glucoside-3'-glucoside
** Mean value (n = 14)
NA: Not analyzed or measured

TABLE 27

| Line No. | | RHS color chart | | | CIEL*a*b* color system | | | | |
| --- | --- | --- | --- | --- | --- | --- | --- | --- | --- |
| Infection No. | Individual No. | HPLC* | | Chart No. | Color group | L | A | B | Hue angle (hue °) | Chroma (C) |
| | | 9.4 tR | 7.2 tR | | | | | | | |
| 94-765 Wild type ** | | – | – | 64A4B 71A-B | Red-Purple | 34.5 | 38.0 | −7.0 | 350.1 | 38.7 |
| | | | | 94-765 transformants | | | | | | |
| 1356- | 1 | + | + | NA | NA | NA | NA | NA | NA | NA |
| 1356- | 2 | + | + | NA | NA | NA | NA | NA | NA | NA |
| 1356- | 4 | + | trace | NA | NA | NA | NA | NA | NA | NA |
| 1356- | 6 | – | – | NA | NA | NA | NA | NA | NA | NA |
| 1356- | 8 | trace | trace | NA | NA | NA | NA | NA | NA | NA |
| 1356- | 9 | + | + | NA | NA | NA | NA | NA | NA | NA |
| 1356- | 10 | + | + | NA | NA | NA | NA | NA | NA | NA |
| 1356- | 12 | + | + | NA | NA | NA | NA | NA | NA | NA |
| 1356- | 15 | + | + | NA | NA | NA | NA | NA | NA | NA |
| 1356- | 17 | + | + | NA | NA | NA | NA | NA | NA | NA |
| 1356- | 18 | + | trace | NA | NA | NA | NA | NA | NA | NA |
| 1356- | 19 | + | + | NA | NA | NA | NA | NA | NA | NA |
| 1356- | 20 | + | + | NA | NA | NA | NA | NA | NA | NA |
| 1356- | 21 | + | + | NA | NA | NA | NA | NA | NA | NA |
| 1356- | 22 | + | + | NA | NA | NA | NA | NA | NA | NA |
| 1356- | 23 | + | + | 72B/74C-D | Red-Purple | 42.5 | 35.8 | −15.7 | 336.3 | 39.1 |
| 1356- | 24 | + | + | 70A-B | Red-Purple | 42.7 | 37.5 | −14.8 | 338.5 | 40.3 |
| 1356- | 25 | + | + | NA | NA | NA | NA | NA | NA | NA |

*+: Detected, trace: trace amount or not detected, 9.4 tR: Cyanidin 3-(3,6-dimalonyl)glucoside-3'-glucoside, 7.2 tR: Cyanidin 3-(3-malonyl)glucoside-3'-glucoside
** Mean value (n = 14)
NA: Not analyzed or measured Reference Example 3: Introduction of pB250 into *Chrysanthemum* Line "94-765" (Coexpression of *Clitoria*-Derived A3'5'GT Gene, *Clitoria*-Derived AGS Gene and *Clitoria*-Derived A3'AT Gene Under the Control of *Chrysanthemum* F3H Promoter 1k and *Agrobacterium* Nos Terminator)

[1] Vector Assembly

Figure 2:
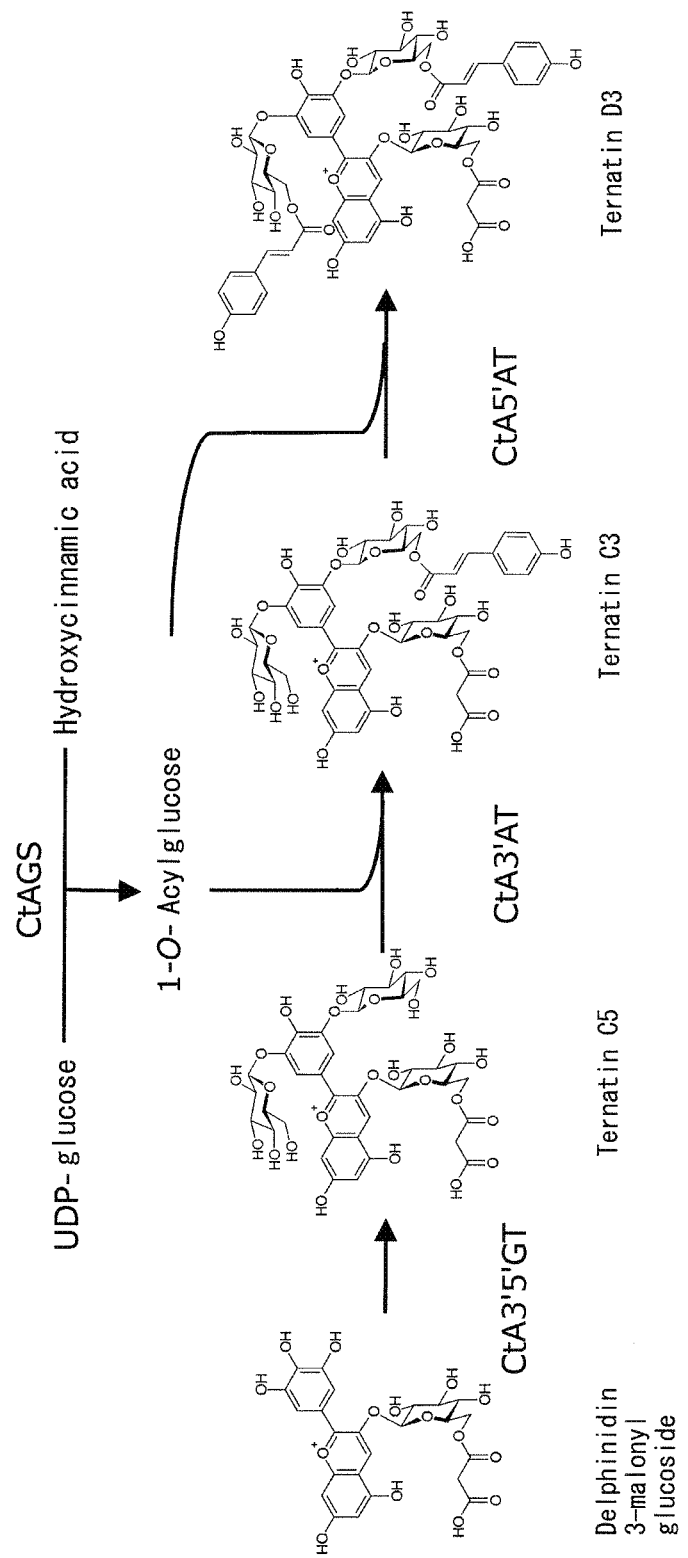
FIG. 2 shows polyacylation of anthocyanins by aromatic organic acids that promote intramolecular association (an example of ternatin biosynthesis in *Clitoria*).

A DNA fragment amplified by PCR using pBSII-CtGT11-4-14, described in Japanese Patent No. 4418865 and containing the CtAGS gene encoding *Clitoria* 1-O-acylglucose synthase (CtAGS, UDP-glucose: hydroxycinnamate 1-O-glucosyltransferase, FIG. 2) as template, and ADH-CtH-CAGT-Fd (5'-CAAGAAAAATAA<u>ATGGGGTCTGAAGCTTCGTTTC</u>-3';

underline indicates sequence annealing with CtAGS genetic code region; SEQ ID NO: 31) and StuI-CtHCAGT-Rv (5'-AGGCCTCATGTTCACAAACTTC-3'; SEQ ID NO: 32) as primers, and a DNA fragment amplified by PCR using pBI221 ADH-221 as template and XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and CtHCAGT-ADH-Rv (5'-TTCAGACCCCAT<u>TTATTTTTCTTGATTTCCTTCAC</u>-3';

underline indicates sequence annealing with NtADH-5'UTR 94 bp; SEQ ID NO: 33) as primers, were combined and used as template for PCR using XbaI-ADH-Fd (SEQ ID NO: 14) and StuI-CtHCAGT-Rv (SEQ ID NO: 32) as primers, to obtain a DNA fragment having tobacco ADH-5'UTR 94 bp directly linked to the start codon of the CtAGS gene. An approximately 850 bp DNA fragment obtained by TA cloning of this DNA fragment in pCR2.1 (Invitrogen) followed by digestion with XbaI and StuI was linked with a vector fragment obtained by digesting pBSII-CtGT11-4-14 with XbaI and StuI, to obtain pBSII-ADH-CtAGS. A DNA fragment obtained by blunting the ends of the XhoI digestion product of this plasmid and then digesting with XbaI was linked with vector fragment obtained by digesting pMCE5 with NheI and EcoICRI, to obtain pMCE5-ADH-AGS. A DNA fragment of the gene expression cassette AscI-CmF3Hp1k:NtADH-5'UTR:CtAGS:nost-PmeI, obtained by digesting this plasmid with AscI and PmeI, was linked with a binary vector DNA fragment pMCE5-ADH-CtAGS obtained by digesting pB249 (pBI121 CmF3Hp1k:ADHNF-*Clitoria* A3'5'GT:NOSt) with SwaI and AscI, to obtain pBI121-CtBGT+AGS.

A DNA fragment amplified by PCR using pBSII-CtAT1-19, which is one of the CtSCPL1 cDNA clones described in Japanese Patent No. 4418865, containing the *Clitoria* A3'AT gene thought to have 3'AT activity and 5'AT activity (FIG. 2), as template and ADH-CtAT1-Fd (5'-CAAGAAAAATAA<u>ATGGCAGCCTTCAGTTCAAC</u>-3';

underline indicates region annealing with CtAT1; SEQ ID NO: 34) and Pst-CtAT1-Rv (5'-CTGCAG-CATCTGTTCTAGCATAA-3'; SEQ ID NO: 35) as primers, and a DNA fragment amplified by PCR using pBI221 ADH-221 as template and XbaI-ADH-Fd (5'-ACGCGTTCTAGA<u>GTCTATTTAACTCAGTATTC</u>-3';

underline indicates sequence annealing with NtADH-5'UTR 94 bp; SEQ ID NO: 14) and CtAT1-ADH-Rv (5'-GAAGGCTGCCAT<u>TTATTTTTCTTGATTTCCTTCAC</u>-3';

underline indicates sequence annealing with NtADH-5'UTR 94 bp; SEQ ID NO: 36) as primers, were combined and used as template for PCR using XbaI-ADH-Fd (SEQ ID NO: 14) and Pst-CtAT1-Rv (SEQ ID NO: 35) as primers, to amplify a DNA fragment having NtADH-5'UTR 94 bp directly linked to the start codon of the CtAT gene. This DNA fragment was digested with XbaI and PstI and linked with a DNA fragment obtained by digesting pBSII-CtAT1-19 with SpeI and PstI, to obtain pBSII-ADHNF-CtAT1-19. An approximately 1.6 kb DNA fragment obtained by digesting this plasmid with NotI and XhoI was linked with a plasmid fragment obtained by NotI and XhoI digestion of pCR2.1, which had been circularized due to self-ligation after digestion with EcoRI, to obtain pCR-ADHNF-CtAT1-19. Also, an approximately 1.6 kb DNA fragment obtained by digesting pBSII-ADHNF-CtAT1-19 with EcoICRI and SalI was linked with a pMCE5 plasmid DNA fragment obtained by digestion with SmaI and SalI, to obtain pMCE5-ADH-CtAT1.

A binary vector DNA fragment obtained by digesting pBI121-CtBGT+AGS with SwaI and AscI was linked with an expression cassette (AscI-CmF3Hp1k:NtADH-5'UTR:Ct3'AT:nost-PmeI) DNA fragment obtained by digesting pMCE5-ADH-CtAT1 with AscI and PmeI, to obtain binary vector pB250 for coexpression of *Clitoria* A3'5'GT, *Clitoria* AGS and *Clitoria* 3'AT under the control of *Chrysanthemum* F3H promoter 1k and *Agrobacterium* nos terminator.

[2] Obtaining Transformants and Measuring Flower Color

The dark red-colored medium-sized *chrysanthemum* line "94-765" (sampled breeding line provided by Inochio Seikoen) was transformed using pB250-transferred *Agrobacterium* EHA105 (provided by Dr. Elizabeth E. Hood), and 11 transformant lines were obtained. Using the same analysis method as in Reference Example 1, it was confirmed that the ligulate petals of 9 of these lines had two major pigments which are thought to be the original anthocyanin pigments in the ligulate petals, i.e. cyanidin 3-(6"-malonyl)glucoside and cyanidin 3-(3",6"-dimalonyl)glucoside, with one glucosyl group bonded to each, but no lines were obtained with petal accumulation of cyanidin glycoside modified by aromatic acyl groups by the function of the *Clitoria*-derived AGS and *Clitoria*-derived A3'AT gene products. Moreover, no lines were obtained with any major flower color change from the original 94-765, and all of them exhibited flower colors in the Red-Purple group (Table 28). Blue *chrysanthemum* was not obtained by the method of expressing the *Clitoria* A3'5'GT gene, acylglucose synthase gene and A3'AT gene with *Chrysanthemum* F3H promoter (FIG. 6).

TABLE 28

| Line No. | | | RHS color chart | | CIEL*a*b* color system | | | | |
|---|---|---|---|---|---|---|---|---|---|
| Infection No. | Individual No. | HPLC* | Chart | Color | | | | Hue angle | Chroma |
| | | 9.4 tR | 7.2 tR | No. | group | L | A | B | (hue °) | (C) |
| 94-765 Wild type ** | | − | − | 64A-B 71A-B | Red-Purple | 34.5 | 38.0 | −7.0 | 350.1 | 38.7 |
| 94-765 transformants | | | | | | | | | | |
| 1357- | 1 | − | − | 71A-B | Red-Purple | 22.5 | 38.6 | −1.2 | 358.2 | 38.7 |
| 1357- | 2 | − | − | NA | NA | NA | NA | NA | NA | NA |
| 1357- | 3 | + | trace | NA | NA | NA | NA | NA | NA | NA |
| 1357- | 4 | + | + | NA | NA | NA | NA | NA | NA | NA |
| 1357- | 5 | + | trace | NA | NA | NA | NA | NA | NA | NA |
| 1357- | 6 | + | + | 72B | Red-Purple | 33.1 | 39.2 | −13.6 | 340.8 | 41.5 |
| 1357- | 7 | + | + | NA | NA | NA | NA | NA | NA | NA |
| 1357- | 8 | + | + | NA | NA | NA | NA | NA | NA | NA |
| 1357- | 9 | + | + | 70A-B | Red-Purple | 40.7 | 38.2 | −14.7 | 338.9 | 40.9 |
| 1357- | 10 | + | + | NA | NA | NA | NA | NA | NA | NA |
| 1357- | 11 | + | + | NA | NA | NA | NA | NA | NA | NA |

*+: Detected, trace: trace amount or not detected, 9.4 tR: Cyanidin 3-(3,6-dimalonyl)glucoside-3'-glucoside, 7.2 tR: Cyanidin 3-(3-malonyl)glucoside-3'-glucoside
** Mean value (n = 14)
NA: Not analyzed or measured Reference Example 4: Introduction of pB420 into *Chrysanthemum* Variety "Taihei" (Coexpression of *Campanula*-Derived F3'5'H Gene and *Clitoria*-Derived AGS Gene Under the Control of *Chrysanthemum* F3H Promoter 1k and *Agrobacterium* Nos Terminator)

[1] Vector Assembly

A DNA fragment obtained by digesting pBSII-ADH-CtAGS obtained in Reference Example 3 with XhoI and blunting the ends, and then digesting with XbaI, was linked with a vector fragment obtained by digesting pMCE5-2 (FASS-CmF3Hp-AtHSPt) with NheI and EcoICRI, to obtain pMCE5-2 ADHNF-CtAGS. An expression cassette obtained by digesting this plasmid with FseI and PmeI was linked with a binary vector fragment of pB315 (pBCam2) obtained by digestion with FseI and SwaI, to obtain pB420 (pB-Cam2+CtAGS).

[2] Obtaining Transformants and Measuring Flower Color

Plasmid pB420-transferred *Agrobacterium* EHA105 (provided by Dr. Elizabeth E. Hood) was used for transformation of the pink medium-sized *chrysanthemum* variety "Taihei" (sampled genetic resource maintained by aseptic culture at the NARO Institute of Floricultural Science), and 40 transformant lines were obtained. As a result of color measurement with a spectroscopic colorimeter (CD100, Yokogawa Electric Corp.) and an RHS color chart, alteration of flower color toward blue was found in 17 lines. However, even in the lines with the most intense blueness, the flower color exhibited had a hue angle of 317° and was in the Purple-Violet group of the RHS color chart, or approximately the same level as with expression of the F3'5'H gene alone (Table 29). In the transfer gene construct for coexpression of the *Clitoria*-derived acylglucose synthase gene (CtAGS) with the F3'5'H gene, no blue *chrysanthemum* was obtained exhibiting a flower color with a hue angle of 230° to 290° and/or in the Violet-Blue group/Blue group.

TABLE 29

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/Purple |
| Ohira transformants | | | | | | | |
| 1731-03 | 60.5 | 18.2 | 17.0 | 317.0 | 24.9 | N82C | Purple-Violet |
| 1731-06 | 66.3 | 12.9 | −12.0 | 317.1 | 17.7 | N82B | Purple-Violet |
| 1731-07 | 57.6 | 21.5 | −18.4 | 319.6 | 28.3 | N81B | Purple-Violet |
| 1731-10 | 56.8 | 20.2 | −18.3 | 317.7 | 27.2 | N82B | Purple-Violet |
| 1731-12 | 75.8 | 8.4 | −4.2 | 333.6 | 9.4 | N80D | Purple-Violet |
| 1731-13 | 73.5 | 9.4 | −8.3 | 318.6 | 12.6 | N81C-D | Purple-Violet |
| 1731-20 | 62.8 | 17.9 | −13.1 | 323.8 | 22.1 | N81B-C | Purple-Violet |
| 1731-21 | 58.8 | 17.8 | −14.9 | 320.0 | 23.2 | N81A-B | Purple-Violet |
| 1731-24 | 68.9 | 20.0 | −6.2 | 342.8 | 20.9 | N81B-C | Purple-Violet |
| 1731-26 | 68.3 | 11.9 | −11.2 | 316.9 | 16.4 | N80C | Purple-Violet |
| 1731-27 | 75.3 | 9.5 | −3.8 | 338.2 | 10.3 | N81C-D | Purple-Violet |
| 1731-28 | 72.4 | 12.1 | −10.2 | 319.9 | 15.8 | N80C | Purple-Violet |
| 1731-30 | 54.8 | 23.1 | −21.0 | 317.8 | 31.2 | N82B | Purple-Violet |
| 1731 33 | 55.8 | 21.7 | −19.4 | 318.2 | 29.1 | N81B | Purple-Violet |
| 1731-35 | 60.0 | 19.2 | −15.8 | 320.5 | 24.9 | N81B-C | Purple-Violet |
| 1731-38 | 66.0 | 18.3 | −14.2 | 322.3 | 23.2 | N81B-C | Purple-Violet |
| 1731-40 | 60.4 | 15.5 | −13.8 | 318.3 | 20.7 | NA | NA |

NA: Not analyzed or measured
* Mean value (n = 23)

Reference Example 5: Introduction of pB430 into *Chrysanthemum* Variety "Taihei" (Coexpression of *Campanula*-Derived F3'5'H Gene, *Clitoria*-Derived AGS Gene and Dutch Iris-Derived DFR Gene Under the Control of *Chrysanthemum* F3H Promoter 1k and *Agrobacterium* Nos Terminator)

[1] Vector Assembly

An expression cassette obtained by digesting pMCE5-2-ADHNF-DbDFR with FseI and PmeI was linked with a binary vector fragment of pB420 (pBCam2+CtAGS) obtained by digestion with FseI and SwaI, to obtain pB430 (pBCam2+CtAGS+IhDFR).

[2] Obtaining Transformants and Measuring Flower Color

Plasmid pB430-transferred *Agrobacterium* EHA105 (provided by Dr. Elizabeth E. Hood) was used for transformation of the pink medium-sized *chrysanthemum* variety "Taipei" (sampled genetic resource maintained by aseptic culture at the NARO Institute of Floricultural Science), and 54 transformant lines were obtained. As a result of color measurement with a spectroscopic colorimeter (CD100, Yokogawa Electric Corp.) and an RHS color chart, alteration of flower color toward blue was found in 33 lines (63%). However, the hue angle of the line with the most intense blue color was 315°, while only lines with colors in the Violet group or Purple-Violet group in measurement by RHSCC were obtained, and there was no significant alteration in flower color compared to expression of the F3'5'H gene alone (Table 30). In the transfer gene construct for coexpression of the *Clitoria*-derived acylglucose synthase gene (CtAGS) and Dutch iris-derived DFR gene with the F3'5'H gene, no blue *chrysanthemum* was obtained exhibiting a flower color with a hue angle of 230° to 290° and/or in the Violet-Blue group/Blue group.

TABLE 30

| | CIEL*a*b* color system | | | | | RHS color chart | |
|---|---|---|---|---|---|---|---|
| Line No. | L | A | B | Hue angle (hue °) | Chroma (C) | Chart No. | Color group |
| Ohira wild type * | 79.5 | 9.7 | −2.0 | 356.6 | 11.1 | 65B, N74C, 75B | Red-Purple/Purple |
| Ohira transformants | | | | | | | |
| 1739-01 | NA | NA | NA | NA | NA | N82C | Purple-Violet |
| 1739-06 | 53.4 | 18.3 | −17.1 | 316.8 | 25.0 | N87B | Violet |
| 1739-07 | 53.2 | 17.2 | −16.5 | 316.2 | 23.9 | N87B | Violet |
| 1739-08 | 50.8 | 23.1 | −20.5 | 318.3 | 30.9 | N82A | Purple-Violet |
| 1739-10 | 63.4 | 17.7 | −13.1 | 323.5 | 22.0 | N82B-C | Purple-Violet |
| 1739-11 | 50.1 | 22.8 | −22.4 | 315.5 | 31.9 | NA | NA |
| 1739-12 | 59.5 | 19.5 | −17.6 | 318.0 | 26.3 | N82A-B | Purple-Violet |
| 1739-15 | NA | NA | NA | NA | NA | N87A-B | Violet |
| 1739-17 | 47.2 | 20.8 | −18.5 | 318.3 | 27.8 | N87A | Violet |
| 1739-18 | 60.0 | 21.1 | −16.3 | 322.4 | 26.6 | 83C-D | Violet |
| 1739-21 | 63.3 | 12.6 | −5.3 | 337.1 | 13.7 | 83C-D | Violet |
| 1739-22 | 55.3 | 18.9 | −18.5 | 315.6 | 26.5 | N82A-B | Purple-Violet |

TABLE 30-continued

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| 1739-25 | 79.0 | 6.6 | -4.5 | 326.0 | 8.0 | N81C | Purple-Violet |
| 1739-26 | 54.5 | 18.5 | -16.4 | 318.5 | 24.8 | N83C-D | Violet |
| 1739-28 | 36.3 | 30.1 | -26.0 | 319.2 | 39.7 | N87A-B | Violet |
| 1739-30 | 63.9 | 17.4 | -10.8 | 328.2 | 20.4 | N81C-D | Purple-Violet |
| 1739-32 | 56.1 | 25.6 | -16.9 | 326.5 | 30.7 | N81B | Purple-Violet |
| 1739-33 | 56.3 | 18.0 | -16.2 | 318.1 | 24.2 | N82B | Purple-Violet |
| 1739-42 | 69.3 | 13.0 | -11.5 | 318.4 | 17.3 | N82B | Purple-Violet |
| 1739-44 | 55.7 | 23.1 | -20.2 | 318.9 | 30.7 | N82A | Purple-Violet |
| 1739-46 | 61.2 | 18.8 | -15.1 | 321.4 | 24.1 | N81B C | Purple-Violet |
| 1739-47 | 47.2 | 22.5 | -20.3 | 317.9 | 30.3 | N87B | Violet |
| 1739-48 | 71.4 | 13.5 | -11.3 | 320.2 | 17.6 | N80C | Purple-Violet |
| 1739-50 | 49.3 | 21.0 | -20.6 | 315.4 | 29.4 | 83B-C | Violet |
| 1739-54 | 50.2 | 21.3 | -21.1 | 315.3 | 29.9 | N87A | Violet |
| 1739-56 | 66.9 | 15.7 | -10.2 | 327.1 | 18.7 | N81B-C | Purple-Violet |
| 1739-60 | 70.6 | 12.6 | -11.3 | 318.0 | 16.9 | 84A-B | Violet |
| 1739-65 | 70.3 | 16.0 | -8.1 | 333.1 | 18.0 | N81B-C | Purple Violet |
| 1739-67 | 67.7 | 14.7 | -11.7 | 321.4 | 18.8 | N81B | Purple-Violet |
| 1739-68 | 66.8 | 14.3 | -9.7 | 326.0 | 17.3 | N80B-C | Purple-Violet |
| 1739-69 | 71.6 | 14.7 | -9.8 | 326.3 | 17.7 | N81C | Purple-Violet |
| 1739-72 | 60.0 | 20.8 | -17.7 | 319.7 | 27.3 | 83C-D | Violet |
| 1739-80 | 60.7 | 20.3 | -15.4 | 322.8 | 25.5 | N81B | Purple-Violet |

NA: Not analyzed or measured
* Mean value (n = 23)

Reference Example 6: Introduction of pB249 into Chrysanthemum Variety "Taihei" (Expression of Clitoria-Derived A3'5'GT Gene Under the Control of Chrysanthemum F3H Promoter 1k and Agrobacterium Nos Terminator)

[1] Vector Assembly

Plasmid pB249 (pBI121 CmF3Hp1k:ADHNF-Clitoria A3'5'GT:NOSt) was obtained according to the method of Reference Example 2.

[2] Obtaining Transformants and Measuring Flower Color

Plasmid pB249-transferred Agrobacterium EHA105 (provided by Dr. Elizabeth E. Hood) was used for transformation of the pink medium-sized chrysanthemum variety "Taihei", and 26 transformant lines were obtained. No lines were obtained with any major flower color change from the original "Taihei", and even the lines that showed some alteration of flower color exhibited a flower color of Purple group 75 (Table 31). As in the case of "94-765" of Reference Example 2, blue chrysanthemum could not be obtained simply by expressing the Clitoria A3'S'GT gene with Chrysanthemum F3H promoter 1k (length: ~1 kb).

TABLE 31

| | CIEL*a*b* color system | | | | | RHS color chart | |
|---|---|---|---|---|---|---|---|
| | | | | Hue | | | |
| Line No. | L | A | B | angle (hue °) | Chroma (C) | Chart No. | Color group |
| Ohira wild type * | 73.1 | 16.4 | -5.1 | 342.9 | 17.2 | 74C | Red-Purple |
| Ohira transformants | | | | | | | |
| 1979-01 | 84.4 | 5.6 | 1.0 | 370.3 | 5.7 | NA | NA |
| 1979-02 | 79.4 | 8.0 | -0.6 | 355.7 | 8.0 | NA | NA |
| 1979-03 | 82.9 | 5.2 | 1.6 | 377.4 | 5.4 | NA | NA |
| 1979-04 | 79.0 | 7.6 | 0.2 | 361.6 | 7.6 | NA | NA |
| 1979-05 | 82.0 | 7.1 | -1.2 | 350.5 | 7.2 | NA | NA |
| 1979-06 | 79.6 | 9.4 | -1.8 | 349.2 | 9.5 | NA | NA |
| 1979-07 | 79.5 | 7.7 | -0.8 | 353.9 | 7.7 | NA | NA |
| 1979 08 | 79.5 | 6.9 | -0.1 | 358.8 | 6.9 | NA | NA |
| 1979-09 | 82.8 | 6.4 | -0.2 | 358.6 | 6.4 | NA | NA |
| 1979-11 | 77.2 | 10.7 | -0.7 | 356.3 | 10.7 | NA | NA |
| 1979-12 | 85.8 | 2.2 | 2.9 | 412.0 | 3.6 | NA | NA |
| 1979-13 | 78.9 | 6.7 | 0.3 | 362.8 | 6.7 | 75A-C | Purple |
| 1979-15 | 78.1 | 7.9 | -0.6 | 355.4 | 7.9 | NA | NA |
| 1979 16 | 78.3 | 7.1 | -0.2 | 358.4 | 7.1 | 75A-B | Purple |
| 1979-18 | 83.5 | 3.8 | 1.1 | 376.4 | 4.0 | 75C | Purple |
| 1979-19 | 78.6 | 10.7 | -1.6 | 351.8 | 10.8 | NA | NA |
| 1979-20 | 74.3 | 11.8 | -3.0 | 345.7 | 12.2 | 77D/75A | Purple |
| 1979-21 | 81.2 | 6.7 | 0.3 | 362.2 | 6.8 | NA | NA |
| 1979-22 | 75.3 | 10.2 | -2.0 | 348.9 | 10.4 | NA | NA |

TABLE 31-continued

| | | | | CIEL*a*b* color system | | RHS color chart | |
|---|---|---|---|---|---|---|---|
| Line No. | L | A | B | Hue angle (hue °) | Chroma (C) | Chart No. | Color group |
| 1979-23 | 81.0 | 7.9 | -1.4 | 350.2 | 8.0 | NA | NA |
| 1979-24 | 77.9 | 7.6 | -1.2 | 351.2 | 7.7 | NA | NA |
| 1979-25 | 84.0 | 5.1 | 0.8 | 368.9 | 5.1 | NA | NA |
| 1979-26 | 79.8 | 4.3 | 1.1 | 374.2 | 4.4 | 75B-C | Purple |
| 1979-27 | 86.4 | 3.6 | 1.8 | 386.8 | 4.1 | 75C | Purple |
| 1979-28 | 79.7 | 6.0 | 1.8 | 376.4 | 6.2 | 75C-D | Purple |
| 1979-29 | 82.4 | 4.9 | 2.2 | 384.6 | 5.3 | NA | NA |

NA: Not analyzed or measured

---

The invention claimed is:

1. An expression cassette comprising:
a first promoter functionally linked to a first polynucleotide encoding an anthocyanin 3',5'-O-glucosyltransferase (A3' 5'GT), wherein the first polynucleotide is selected from the group consisting of the following (a) to (d):
(a) a polynucleotide comprising the nucleotide sequence of SEQ ID NO: 1;
(b) a polynucleotide encoding a protein comprising the amino acid sequence of SEQ ID NO: 2;
(c) a polynucleotide encoding a protein having one to five amino acids deleted, substituted, or inserted in the amino acid sequence of SEQ ID NO: 2; and
(d) a polynucleotide encoding a protein having an amino acid sequence identity of 95% or greater with SEQ ID NO: 2, and
a second promoter functionally linked to a second polynucleotide encoding a flavonoid 3',5'-hydroxylase (F3'5'H), wherein the second polynucleotide is selected from the group consisting of the following (e) to (h):
(e) a polynucleotide comprising the nucleotide sequence of SEQ ID NO: 3;
(f) a polynucleotide encoding a protein comprising the amino acid sequence of SEQ ID NO: 4;
(g) a polynucleotide encoding a protein having one to five amino acids deleted, substituted, or inserted in the amino acid sequence of SEQ ID NO: 4; and
(h) a polynucleotide encoding a protein having an amino acid sequence identity of 95% or greater with SEQ ID NO: 4,
such that introduction of the expression cassette into a chrysanthemum plant results in blue chrysanthemum flower petals arising from delphinidin 3-(6"-malonyl)glucoside-3',5'-diglucoside (ternatin C5) and/or delphinidin 3,3',5'-triglucoside (preternatin C5) production by F3'5'H and A3'5'GT.

2. The expression cassette according to claim 1, further comprising (i) a first terminator functionally linked to the first polynucleotide, and (ii) a second terminator functionally linked to the second polynucleotide.

3. The expression cassette according to claim 2, wherein the first promoter is a Chrysanthemum F3H promoter, and the first terminator is an Arabidopsis HSP terminator or an Agrobacterium nos terminator.

4. The expression cassette according to claim 2, wherein the second promoter is a Chrysanthemum F3H promoter, and the second terminator is an Arabidopsis HSP terminator or an Agrobacterium nos terminator.

5. A recombinant vector comprising the expression cassette according to claim 1.

6. A transformed chrysanthemum plant comprising the expression cassette according to claim 1, or its inbred or outbred progenies, or their propagules, partial plant bodies, tissue or cells, wherein each of the plant, the progeny, the propagule, the partial plant body, the tissue, and the cells comprises the expression cassette.

7. The transformed chrysanthemum plant, or its inbred or outbred progenies, or their propagules, partial plant bodies, tissue or cells according to claim 6, wherein the Clitoria-derived anthocyanin 3',5'-O-glucosyltransferase (CtA3'5'GT) gene and the Campanula-derived flavonoid 3',5'-hydroxylase (CamF3'S'H) gene are co-expressed in the chrysanthemum petals.

8. The transformed chrysanthemum plant, or its inbred or outbred progenies, or their propagules, partial plant bodies, tissue or cells according to claim 6, comprising delphinidin 3-(6"-malonyl)glucoside-3',5'-diglucoside (ternatin C5) and/or delphinidin 3,3',5'-triglucoside (preternatin C5).

9. A cut flower of the transformed chrysanthemum plant or its inbred or outbred progenies according to claim 6, or a processed form created from the cut flower, wherein each of the cut flower and the processed form comprises the expression cassette.

10. A method for creating a transformed chrysanthemum plant with a blue flower color, the method comprising a step of transferring:
a first polynucleotide encoding an anthocyanin 3',5'-O-glucosyltransferase (A3'5'GT) and a second polynucleotide encoding a flavonoid 3',5'-hydroxylase (F3'5'H) into a host chrysanthemum plant,
wherein the first polynucleotide is selected from the group consisting of the following (a) to (d):
(a) a polynucleotide comprising the nucleotide sequence of SEQ ID NO: 1;
(b) a polynucleotide encoding a protein comprising the amino acid sequence of SEQ ID NO: 2;
(c) a polynucleotide encoding a protein having one to five amino acids deleted, substituted, or inserted in the amino acid sequence of SEQ ID NO: 2; and (d) a polynucleotide encoding a protein having an amino acid sequence identity of 95% or greater with SEQ ID NO: 2, and wherein the second polynucleotide is selected from the group consisting of the following (e) to (h):

(e) a polynucleotide comprising the nucleotide sequence of SEQ ID NO: 3;
(f) a polynucleotide encoding a protein comprising the amino acid sequence of SEQ ID NO: 4;
(g) a polynucleotide encoding a protein having one to five amino acids deleted, substituted, or inserted in the amino acid sequence of SEQ ID NO: 4; and
(h) a polynucleotide encoding a protein having an amino acid sequence identity of 95% or greater with SEQ ID NO: 4.

11. A method for creating a transformed *chrysanthemum* plant with a blue flower color, the method comprising a step of transferring the expression cassette according to claim 1 or a recombinant vector comprising the expression cassette according to claim 1 in a host *chrysanthemum* plant.

12. The method according to claim 10, wherein the blue flower color is in the Blue group or Violet-Blue group of the RHS color chart, and/or has a hue angle of 230° to 290° in the CIEL*a*b* color system.

13. A transformed *chrysanthemum* plant created by the method according to claim 10, or its inbred or outbred progenies, or their propagules, partial plant bodies, tissue or cells, wherein each of the plant, the progeny, the propagule, the partial plant body, the tissue, and the cells comprises the first polynucleotide and the second polynucleotide.

14. A cut flower of the transformed *chrysanthemum* plants or its inbred or outbred progenies according to claim 13, or a processed form created from the cut flower, wherein each of the cut flower and the processed form comprises the first polynucleotide and the second polynucleotide.

* * * * *